(12) United States Patent
Kim et al.

(10) Patent No.: US 9,246,109 B2
(45) Date of Patent: *Jan. 26, 2016

(54) COMPOUND AND ORGANIC LIGHT EMITTING DEVICE INCLUDING THE SAME

(71) Applicants: Young-Kook Kim, Yongin (KR); Seok-Hwan Hwang, Yongin (KR); Hye-Jin Jung, Yongin (KR); Jun-Ha Park, Yongin (KR); Eun-Young Lee, Yongin (KR); Jin-O Lim, Yongin (KR); Sang-Hyun Han, Yongin (KR); Eun-Jae Jeong, Yongin (KR); Soo-Yon Kim, Yongin (KR); Dae-Yup Shin, Yongin (KR); Jong-Hyuk Lee, Yongin (KR)

(72) Inventors: Young-Kook Kim, Yongin (KR); Seok-Hwan Hwang, Yongin (KR); Hye-Jin Jung, Yongin (KR); Jun-Ha Park, Yongin (KR); Eun-Young Lee, Yongin (KR); Jin-O Lim, Yongin (KR); Sang-Hyun Han, Yongin (KR); Eun-Jae Jeong, Yongin (KR); Soo-Yon Kim, Yongin (KR); Dae-Yup Shin, Yongin (KR); Jong-Hyuk Lee, Yongin (KR)

(73) Assignee: SAMSUNG DISPLAY CO., LTD., Yongin, Gyeonggi-Do (KR)

( * ) Notice: Subject to any disclaimer, the term of this patent is extended or adjusted under 35 U.S.C. 154(b) by 262 days.

This patent is subject to a terminal disclaimer.

(21) Appl. No.: 13/800,962

(22) Filed: Mar. 13, 2013

(65) Prior Publication Data

US 2014/0110676 A1 Apr. 24, 2014

(30) Foreign Application Priority Data

Oct. 19, 2012 (KR) .......................... 10-2012-0116743

(51) Int. Cl.
*H01L 51/50* (2006.01)
*H01L 51/00* (2006.01)
(Continued)

(52) U.S. Cl.
CPC .......... *H01L 51/0072* (2013.01); *C07D 209/82* (2013.01); *C07D 209/86* (2013.01);
(Continued)

(58) Field of Classification Search
None
See application file for complete search history.

(56) References Cited

U.S. PATENT DOCUMENTS 3,968,051 A 7/1976 Stamm et al.
4,521,605 A 6/1985 Okazaki et al.
(Continued)

FOREIGN PATENT DOCUMENTS

JP 1996-012600 A 1/1996
JP 2000-003782 A 1/2000
(Continued)

OTHER PUBLICATIONS

"A novel conjugated polymer based on 4H-benzo[def]carbazole backbone for OLED;" Oct. 8, 2009-Oct. 9, 2009, 2009 Fall Assembly and Symposium; vol. 34, No. 2; Gwangju Institute of Science and Technology.

*Primary Examiner* — Gregory Clark
(74) *Attorney, Agent, or Firm* — Lee & Morse, P.C.

(57) ABSTRACT

A compound represented by Formula 1, below, and an organic light-emitting device including the compound represented by Formula 1:

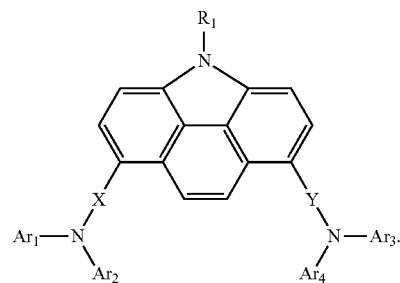

20 Claims, 1 Drawing Sheet

(51) Int. Cl.

| | | |
|---|---|---|
| *C07D 403/04* | (2006.01) | |
| *C07D 405/04* | (2006.01) | |
| *C07D 409/14* | (2006.01) | |
| *C07D 209/82* | (2006.01) | |
| *C07D 401/14* | (2006.01) | |
| *C07D 403/14* | (2006.01) | |
| *C07D 209/86* | (2006.01) | |
| *C07D 209/88* | (2006.01) | |

(52) U.S. Cl.
CPC ............ C07D209/88 (2013.01); C07D 401/14 (2013.01); C07D 403/04 (2013.01); C07D 403/14 (2013.01); C07D 405/04 (2013.01); C07D 409/14 (2013.01); H01L 51/006 (2013.01); H01L 51/0061 (2013.01); H01L 51/5088 (2013.01)

(56) References Cited

U.S. PATENT DOCUMENTS

| | | |
|---|---|---|
| 5,635,308 A | 6/1997 | Inoue et al. |
| 5,972,247 A | 10/1999 | Shi et al. |
| 6,465,115 B2 | 10/2002 | Shi et al. |
| 6,596,415 B2 | 7/2003 | Shi et al. |
| 6,660,410 B2 | 12/2003 | Hosokawa |
| 6,670,054 B1 | 12/2003 | Hu et al. |
| 6,979,414 B2 | 12/2005 | Hosokawa |
| 2001/0046612 A1 | 11/2001 | Lee et al. |
| 2003/0186077 A1* | 10/2003 | Chen ................... C07D 209/80 428/690 |
| 2007/0290610 A1 | 12/2007 | Park et al. |
| 2012/0292603 A1* | 11/2012 | Kwak et al. ..................... 257/40 |
| 2013/0168646 A1* | 7/2013 | Kim ................................ 257/40 |
| 2013/0207082 A1* | 8/2013 | Cho et al. ....................... 257/40 |

FOREIGN PATENT DOCUMENTS

| | | |
|---|---|---|
| KR | 10-0346984 B1 | 7/2002 |
| KR | 10 2007-0119470 A | 12/2007 |

\* cited by examiner

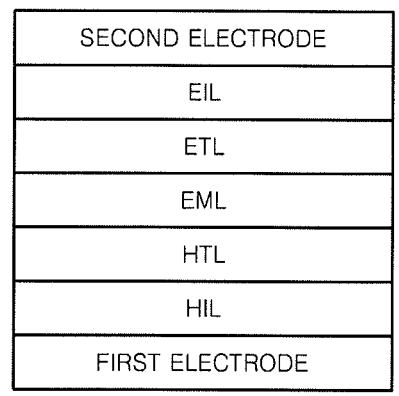

COMPOUND AND ORGANIC LIGHT EMITTING DEVICE INCLUDING THE SAME

CROSS-REFERENCE TO RELATED PATENT APPLICATION

This application claims the benefit of Korean Patent Application No. 10-2012-0116743, filed on Oct. 19, 2012, in the Korean Intellectual Property Office, the disclosure of which is incorporated herein in its entirety by reference.

BACKGROUND

1. Field of the Invention

The embodiments relate to a compound and an organic light-emitting device including the same.

2. Description of the Related Art

Organic light-emitting devices (OLEDs), which are self-emitting devices, have advantages such as wide viewing angles, excellent contrast, quick response, high brightness, excellent driving voltage characteristics, and can provide multicolored images. An OLED may have a structure including a substrate, and an anode, a hole transport layer (HTL), an emission layer (EML), an electron transport layer (ETL), and a cathode, which are sequentially stacked on the substrate. In this regard, the HTL, the EML, and the ETL are organic thin films formed of organic compounds.

An operating principle of an OLED having the above-described structure is as follows. When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

SUMMARY

The embodiments provide a compound with improved characteristics, and a high-efficiency, low-voltage, high-luminance, and long-lifetime organic light-emitting device including the compound. The compound has improved electrical characteristics, good charge transporting capabilities, improved emission capability, a high glass transition temperatures (Tg) enough to prevent crystallization. The compound is suitable as an electron transporting material for fluorescent or phosphorescent device of any color, or as a red green, blue, or white light-emitting material with higher emission efficiency and longer lifetime, and appropriate color coordinates, as compared with existing host materials.

According to an embodiment, there is provided a compound represented by Formula 1 below:

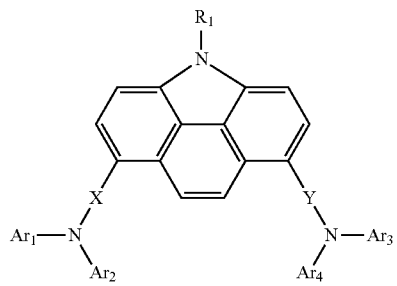

<Formula 1> wherein, in Formula 1, $R_1$ is a substituted or unsubstituted C1-C60 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C3-C60 cycloalkenyl group, a substituted or unsubstituted C5-C60 aryl group, a substituted or unsubstituted C2-C60 heteroaryl group, a substituted or unsubstituted C5-C60 aryloxy group, a substituted or unsubstituted C5-C60 arylthio group; or a substituted or unsubstituted C6-C60 condensed polycyclic group, $Ar_1$ to $Ar_4$ are each independently a substituted or unsubstituted C6-C60 aryl group, a substituted or unsubstituted C2-C60 heteroaryl group, or a substituted or unsubstituted C6-C60 condensed polycyclic group, and X and Y are each independently a single bond, a substituted or unsubstituted C6-C60 arylene group, a substituted or unsubstituted C2-C60 heteroarylene group, a substituted or unsubstituted C6-C60 condensed polycyclic group, or a divalent linking group formed by linking at least two of the arylene group, the heteroarylene group, and the condensed polycyclic groups.

According to another embodiment, there is provided an organic light-emitting device including a first electrode, a second electrode, and an organic layer disposed between the first electrode and the second electrode, wherein the organic layer includes the compound of Formula 1 described above.

According to another embodiment, there is provided a flat panel display device including the above-described organic light-emitting device, wherein the first electrode of the organic light-emitting device is electrically connected to a source electrode or a drain electrode of a thin-film transistor.

BRIEF DESCRIPTION OF THE DRAWING

Features will become apparent to those of skill in the art by describing in detail exemplary embodiments with reference to the attached drawing in which:

FIG. 1 illustrates a schematic view of a structure of an organic light-emitting device according to an embodiment.

DETAILED DESCRIPTION

As used herein, the term "and/or" includes any and all combinations of one or more of the associated listed items. Expressions such as "at least one of," when preceding a list of elements, modify the entire list of elements and do not modify the individual elements of the list.

According to an embodiment, there is provided a compound represented by Formula 1 below.

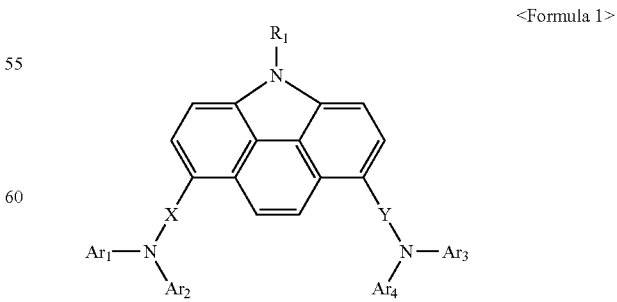

<Formula 1>

In Formula 1, $R_1$ may be a substituted or unsubstituted C1-C60 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C3-C60 cycloalkenyl group, a substituted or unsubstituted C5-C60 aryl group, a substituted or unsubstituted C2-C60 heteroaryl group, a substituted or unsubstituted C5-C60 aryloxy group, a substituted or unsubstituted C5-C60 arylthio group; or a substituted or unsubstituted C6-C60 condensed polycyclic group.

$Ar_1$ to $Ar_4$ may be each independently a substituted or unsubstituted C6-C60 aryl group, a substituted or unsubstituted C2-C60 heteroaryl group, or a substituted or unsubstituted C6-C60 condensed polycyclic group.

X and Y may be each independently a single bond, a substituted or unsubstituted C6-C60 arylene group, a substituted or unsubstituted C2-C60 heteroarylene group, a substituted or unsubstituted C6-C60 condensed polycyclic group, or a divalent linking group formed by linking at least two of the arylene group, the heteroarylene group, and the condensed polycyclic groups.

The compound represented by Formula 1 above may serve as a light-emitting material and/or a hole transporting material or a hole injecting material for organic light-emitting devices. The compound represented by Formula 1 having a condensed ring in molecules has a high glass transition temperature (Tg) or a high melting point due to the inclusion of the condensed ring. Thus, the compound of Formula 1 may have improved heat resistance against Joule heat generated in an organic layer, between organic layers, or between an organic layer and a metal electrode when light emission occurs, and have high durability in high-temperature environments. An organic light-emitting device manufactured using the condensed ring compound of Formula 1 may have improved durability when stored or operated.

Substituents in the compound of Formula 1 will now be described in detail.

In an implementation, in Formula 1, $Ar_1$, $Ar_2$, or X may be linked to one another to form a ring, and/or $Ar_3$, $Ar_4$, or Y may be linked to one another form a ring.

In some embodiments, in Formula 1, $R_1$ may be one of the groups represented by Formulae 2a to 2d.

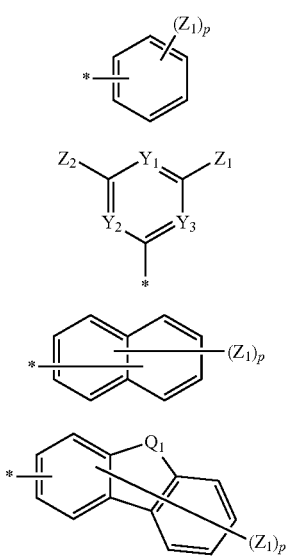

In Formulae 2a-2d, $Y_1$, $Y_2$, and $Y_3$ may be each independently C, or N; $Q_1$ may be a linking group represented by —$C(R_{30})(R_{31})$—, or —$N(R_{32})$—; and $Z_1$, $Z_2$, $R_{30}$, $R_{31}$, and $R_{32}$ may each independently a hydrogen atom, a deuterium atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, —Si$(R_{40})_3$, a halogen group, a cyano group, a nitro group, a hydroxy group, or a carboxy group.

$R_{40}$ may be a substituted or unsubstituted C1-C20 alkyl group, a substituted or unsubstituted C5-C20 aryl group, a substituted or unsubstituted C3-C20 heteroaryl group, or a substituted or unsubstituted C6-C20 condensed polycyclic group;

p may be an integer from 1 to 7; and * indicates a binding site to a nitrogen atom.

In some other embodiments, in Formula 1, $Ar_1$ to $Ar_4$ may be each independently one of the group represented by Formulae 3a to 3d below.

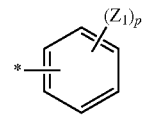

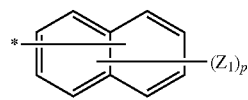

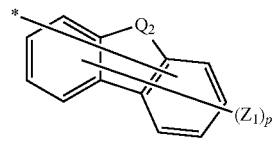

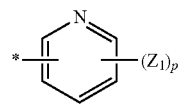

In Formula 3a to 3d, $Q_2$ may be a linking group represented by —$C(R_{30})(R_{31})$—, —$N(R_{32})$—, —S—, or —O—.

$Z_1$, $R_{30}$, $R_{31}$, and $R_{32}$ may be each independently, a hydrogen atom, a deuterium atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, —Si$(R_{40})_3$, a halogen group, a cyano group, a nitro group, a hydroxy group or a carboxy group.

$R_{40}$ may be a substituted or unsubstituted C1-C20 alkyl group, a substituted or unsubstituted C5-C20 aryl group, a substituted or unsubstituted C3-C20 heteroaryl group, or a substituted or unsubstituted C6-C20 condensed polycyclic group;

p is an integer from 1 to 7; and * indicates a binding site to a nitrogen atom.

In some other embodiments, in Formula 1, X and Y may be each independently one of the groups represented by Formulae 4a to 4f below.

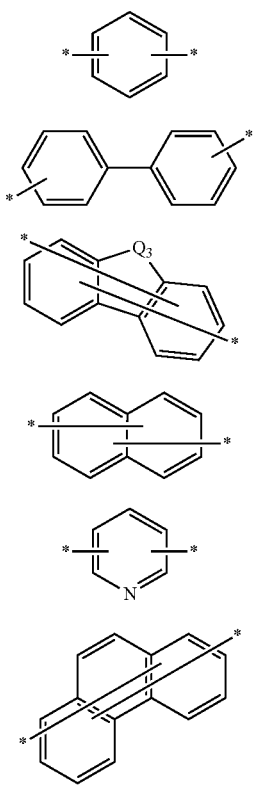

In Formulae 4a to 4f, $Q_3$ may be a linking group represented by —C($R_{30}$)($R_{31}$)—, —N($R_{32}$)—, or —O—.

$R_{30}$, $R_{31}$, and $R_{32}$ may be each independently a hydrogen atom, a deuterium atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen group, a cyano group, a nitro group, a hydroxy group, or a carboxy group.

$R_{30}$ and $R_{31}$ may be optionally linked to form a ring, for example, a linking group as a spiro compound; and * indicates a binding site to a nitrogen atom or a carbon atom.

Hereinafter, substituents described with reference to the formulae will now be described in detail. In this regard, the numbers of carbons in substituents are presented only for illustrative purposes and do not limit the characteristics of the substituents.

The unsubstituted C1-C60 alkyl group may be linear or branched. Non-limiting examples of the unsubstituted C1-C60 alkyl group may include methyl, ethyl, propyl, isobutyl, sec-butyl, pentyl, iso-amyl, hexyl, heptyl, octyl, nonanyl, and dodecyl. At least one hydrogen atom of the C1-C60 alkyl group may be substituted with a deuterium atom, a halogen atom, a hydroxy group, a nitro group, a cyano group, an amino group, an amidino group, a hydroxyrazine, a hydroxyrazone, a carboxyl group or a salt thereof, a sulfonic acid group or a salt thereof, a phosphoric acid group or a salt thereof, or a C1 to 10 alkyl group, a C1 to 10 alkoxy group, a C2 to 10 alkenyl group, a C2 to 10 alkynyl group, a C6 to 16 aryl group, a C4 to 16 heteroaryl group, or an organosilyl group.

The unsubstituted C2-C60 alkenyl group indicates an unsaturated alkyl group having at least one carbon-carbon double bond in a center or at a terminal of the alkyl group. Examples of the alkenyl group may include an ethenyl group, a propenyl group, a butenyl group, and the like. At least one hydrogen atom in the alkenyl group may be substituted with a substituent described above in conjunction with the alkyl group.

The unsubstituted C2-C60 alkynyl group indicates an alkyl group having at least one carbon-carbon triple bond in a center or at a terminal of the alkyl group. Non-limiting examples of the unsubstituted C2-C20 alkynyl group may include acetylene, propylene, phenylacetylene, naphthylacetylene, isopropylacetylene, t-butylacetylene, and diphenylacetylene. At least one hydrogen atom in the alkynyl group may be substituted with a substituent described above in conjunction with the alkyl group.

The unsubstituted C3-C60 cycloalkyl group indicates a C3-C60 cyclic alkyl group wherein at least one hydrogen atom in the cycloalkyl group may be substituted with a substituent described above in conduction with the C1-C60 alkyl group.

The unsubstituted C1-C60 alkoxy group indicates a group having a structure of —OA wherein A is an unsubstituted C1-C60 alkyl group as described above. Non-limiting examples of the unsubstituted C1-C60 alkoxy group may include a methoxy group, an ethoxy group, a propoxy group, an isopropyloxy group, a butoxy group, and a pentoxy group. At least one hydrogen atom of the alkoxy group may be substituted with a substituent such as those described above in conjunction with the alkyl group.

The unsubstituted C5-C60 aryl group indicates a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with a substituent described above in conjunction with the unsubstituted C1-C60 alkyl group.

Non-limiting examples of the a substituted or unsubstituted C5-C60 aryl group may include a phenyl group, a C1-C10 alkylphenyl group (for example, ethylphenyl group), a halophenyl group (for example, o-, m-, and p-fluorophenyl group, dichlorophenyl group), a cyanophenyl group, dicyanophenyl group, a trifluoromethoxyphenyl group, a biphenyl group, a halobiphenyl group, a cyanobiphenyl group, a C1-C10 alkyl biphenyl group, a C1-C10 alkoxybiphenyl group, a o-, m-, and p-toryl group, an o-, m-, and p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (for example, fluoronaphthyl group), a C1-C10 alkylnaphthyl group (for example, methylnaphthyl group), a C1-C10 alkoxynaphthyl group (for example, methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted C3-C60 heteroaryl group used herein may include one, two or three hetero atoms selected from N, O, P and S. At least two rings may be fused to each other or linked to each other by a single bond. Non-limiting examples of the unsubstituted C4-C60 heteroaryl group may include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazol group, an indol group, a quinolyl group, an isoquinolyl group, and a dibenzothiophene group. In addition, at least one hydrogen atom in the heteroaryl group may be substituted with a substituent described above in conjunction with the unsubstituted C1-C60 alkyl group.

The unsubstituted C5-C60 aryloxy group is a group represented by —$OA_1$ wherein $A_1$ may be a C5-C60 aryl group. An example of the aryloxy group may include a phenoxy group. At least one hydrogen atom in the aryloxy group may be substituted with a substituent described above in conjunction with the unsubstituted C1-C60 alkyl group.

The unsubstituted C5-C60 arylthio group is a group represented by —$SA_1$ wherein $A_1$ may be a C5-C60 aryl group. Non-limiting examples of the arylthio group may include a benzenethio group and a naphthylthio group. At least one hydrogen atom in the arylthio group may be substituted with a substituent described above in conjunction with the unsubstituted C1-C60 alkyl group.

The unsubstituted C6-C60 condensed polycyclic group used herein refers to a substituent including at least two rings wherein at least one aromatic ring and/or at least one non-aromatic ring are fused to each other, or refers to a substituent having an unsaturated group in a ring that may not form a conjugate structure. The unsubstituted C6-C60 condensed polycyclic group is distinct from an aryl group or a heteroaryl group in terms of being non-aromatic.

Non-limiting examples of the compound represented by Formula 1 may include Compounds 1 to 60, below.

1

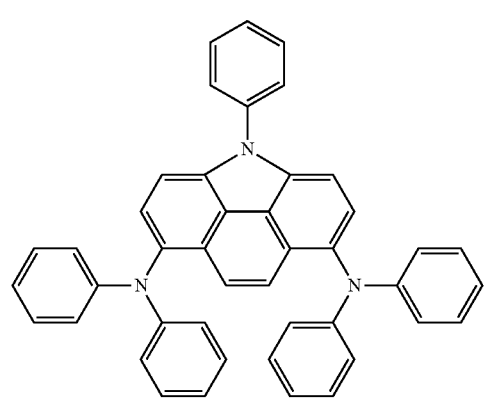

2

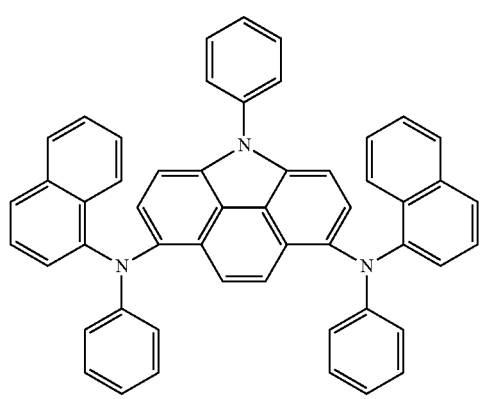

3

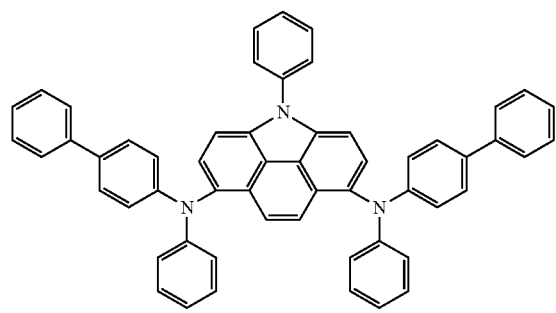

4

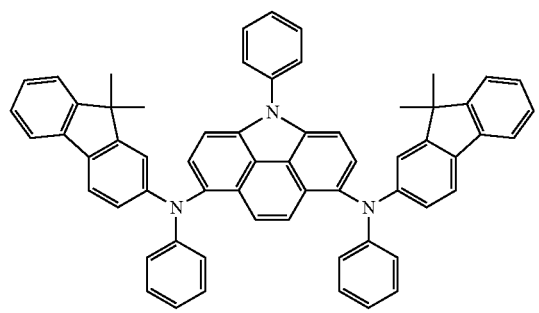

5

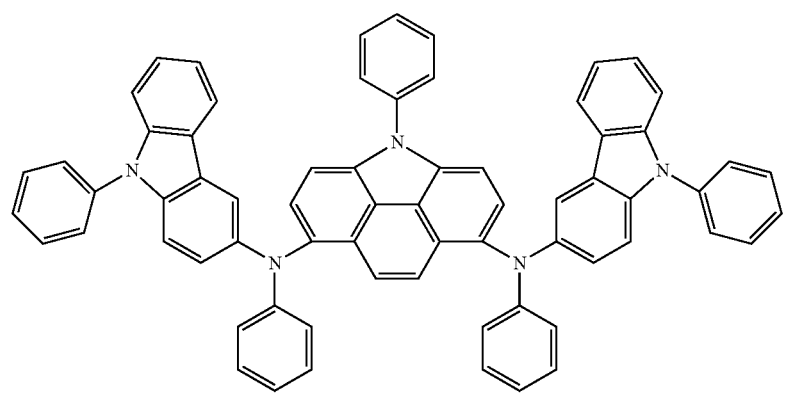

-continued
6
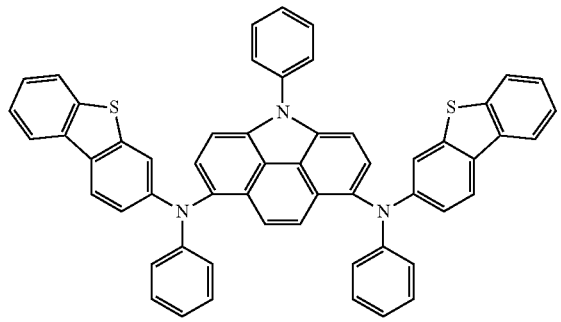
7
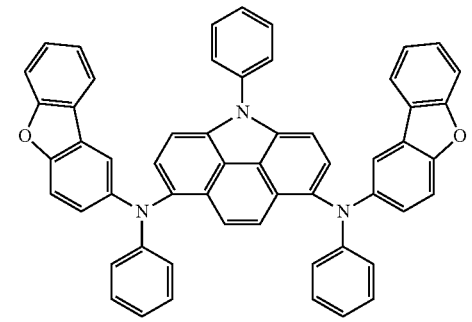
8
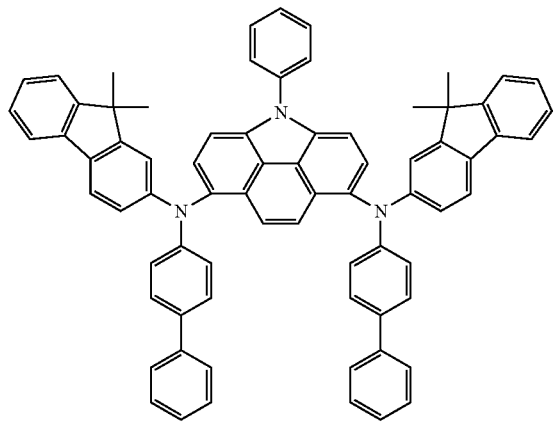
9
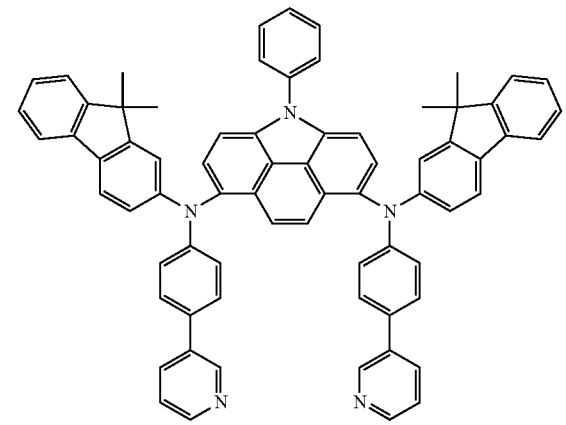
10
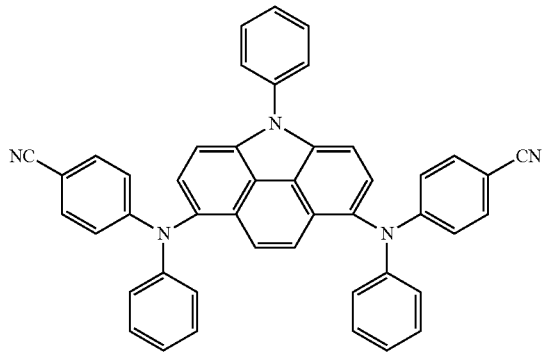
11
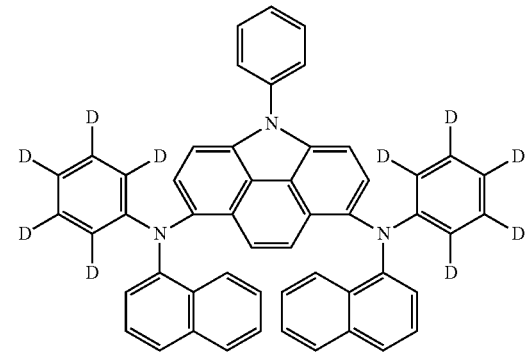
12
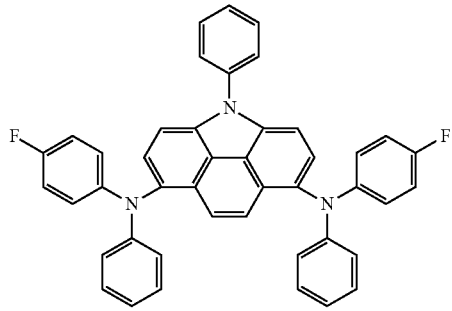
13
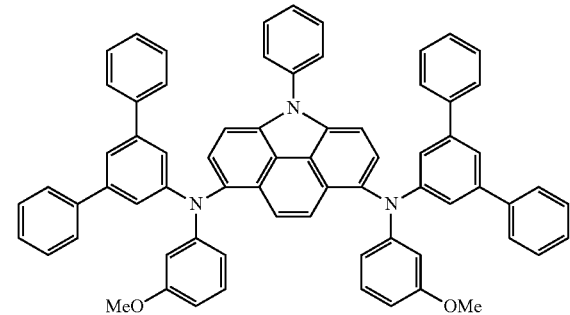

14
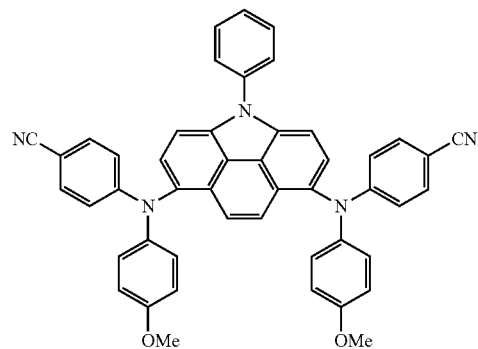
15
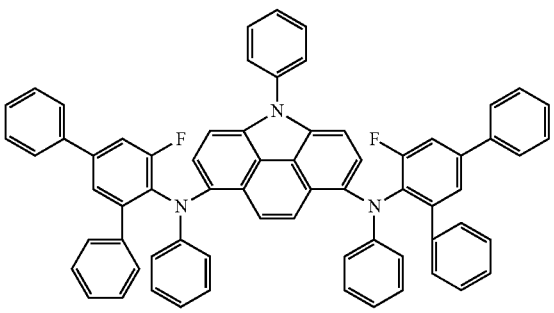
16
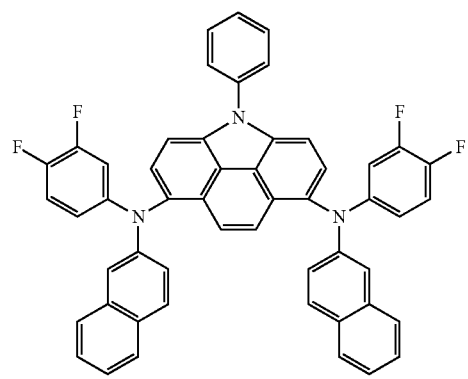
17
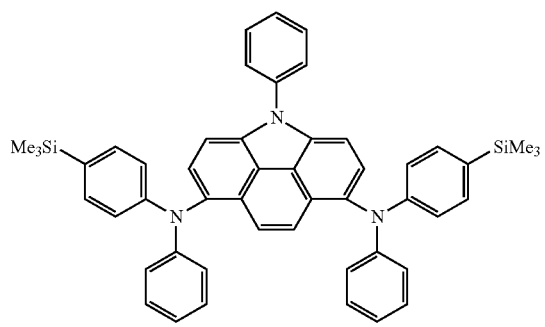
18
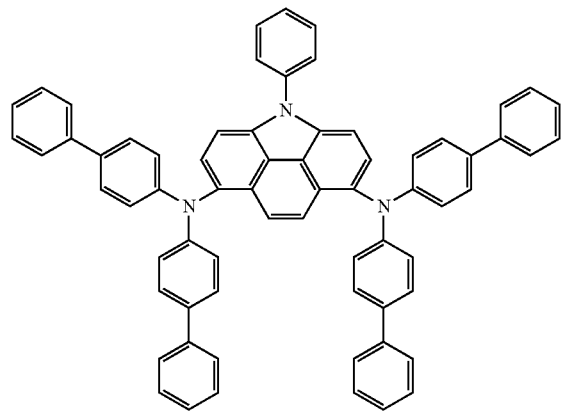
19
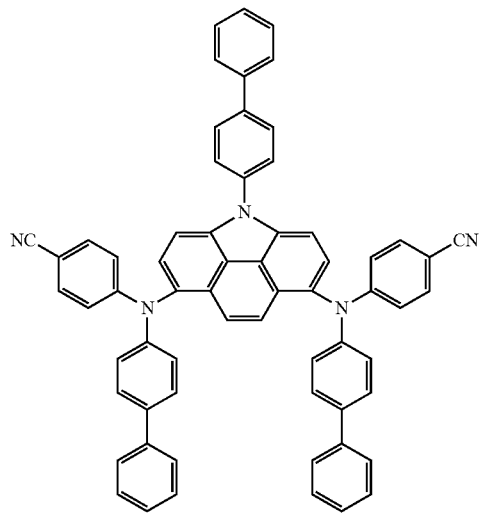

-continued
20
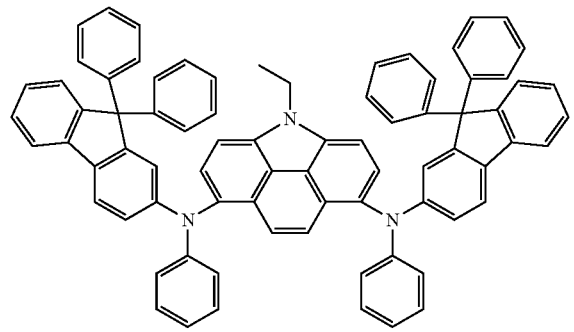
21
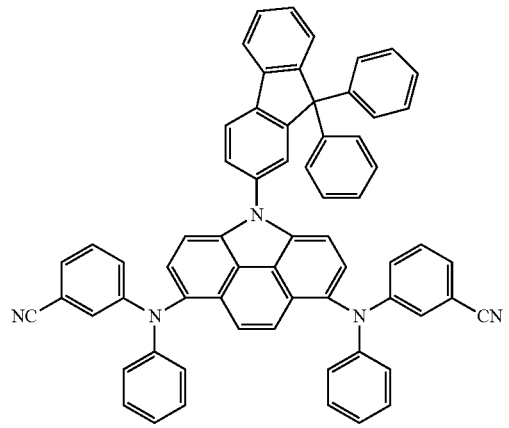
22
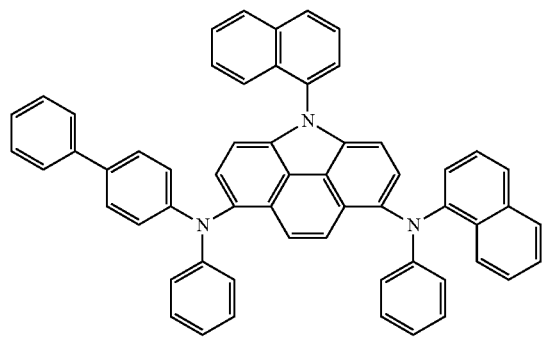
23
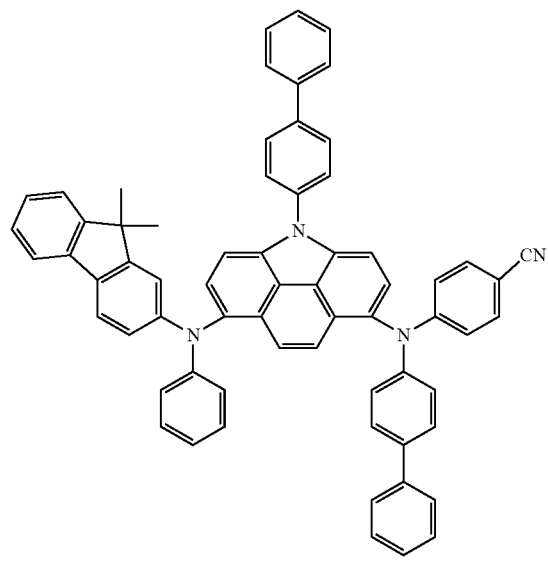
24
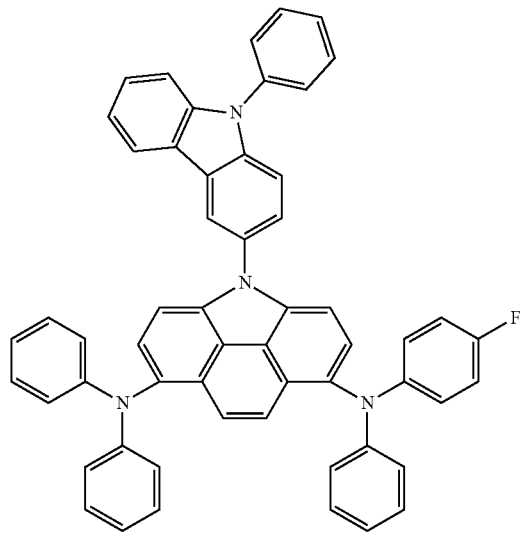
25
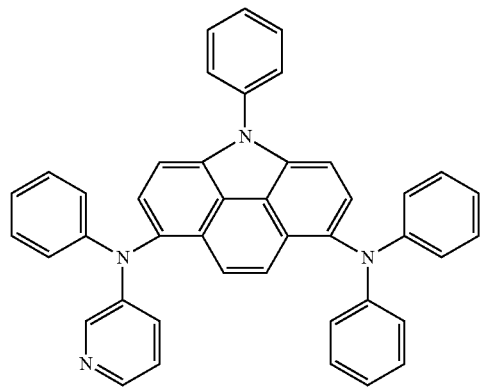

-continued
26
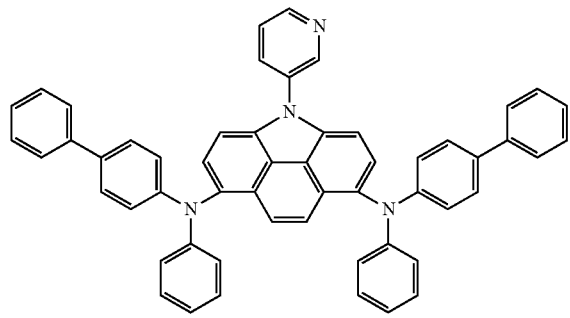
27
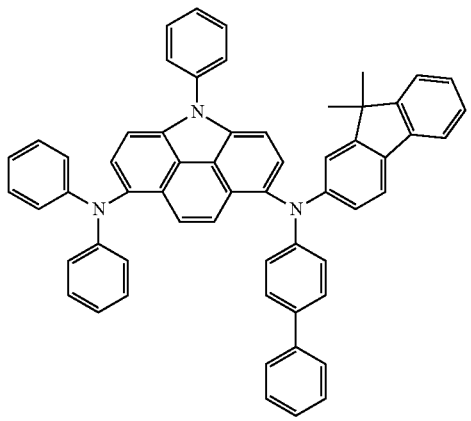
28
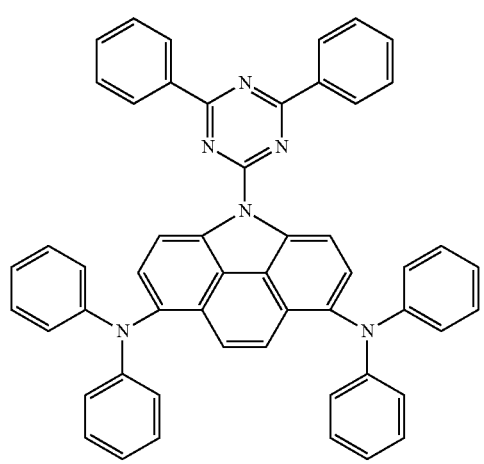
29
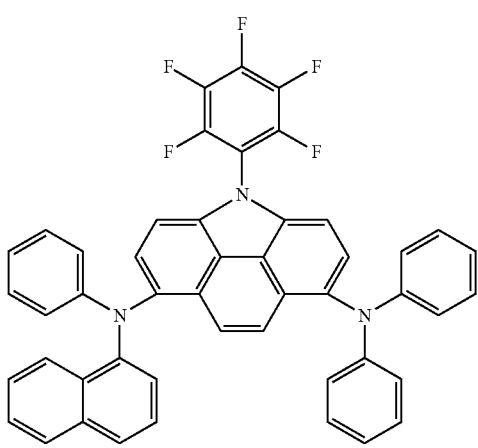
30
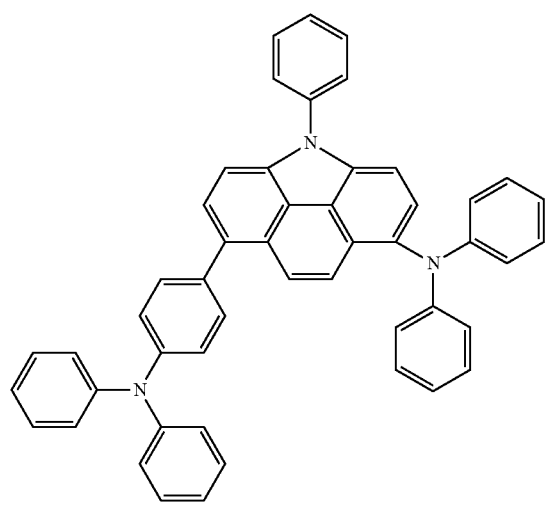
31
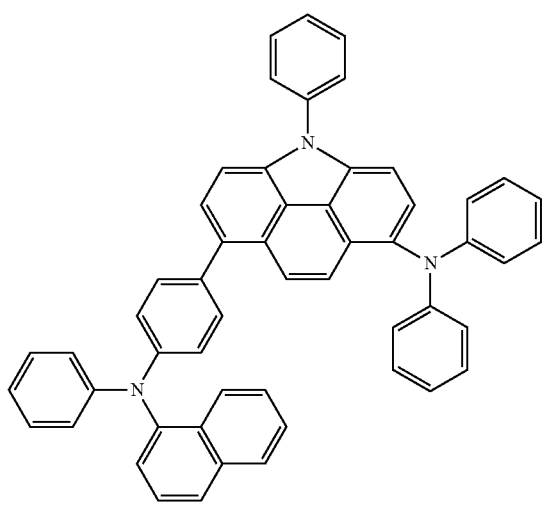

32
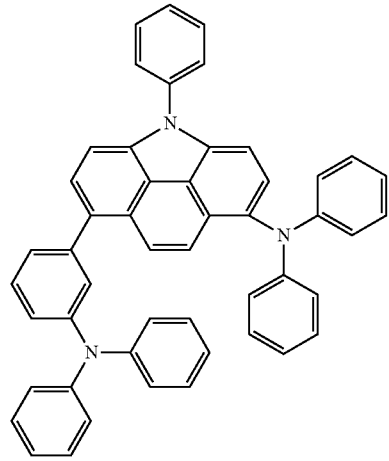
33
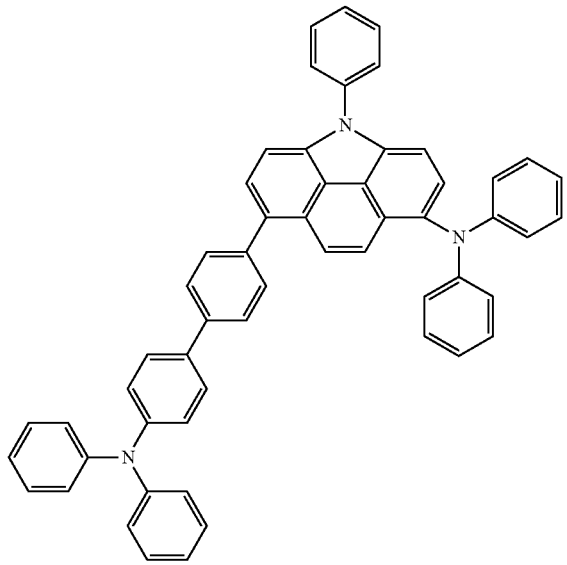
34
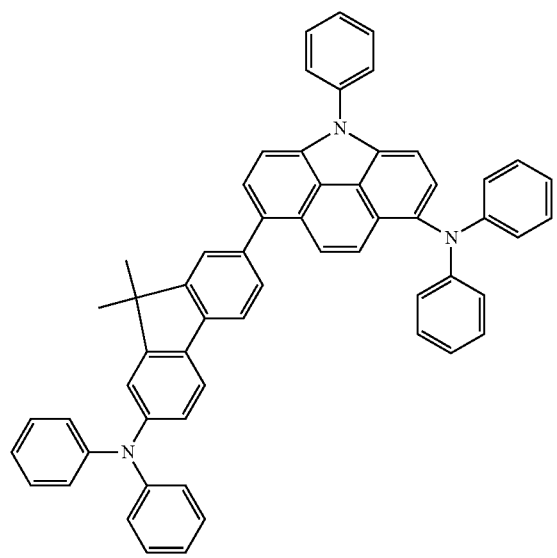
35
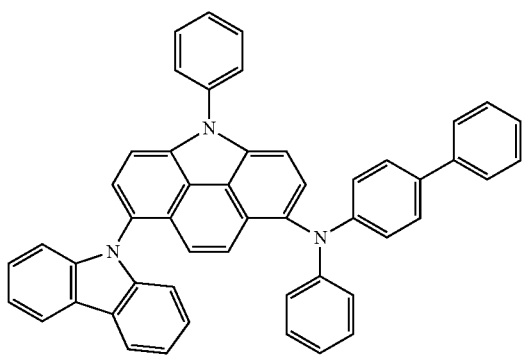
36
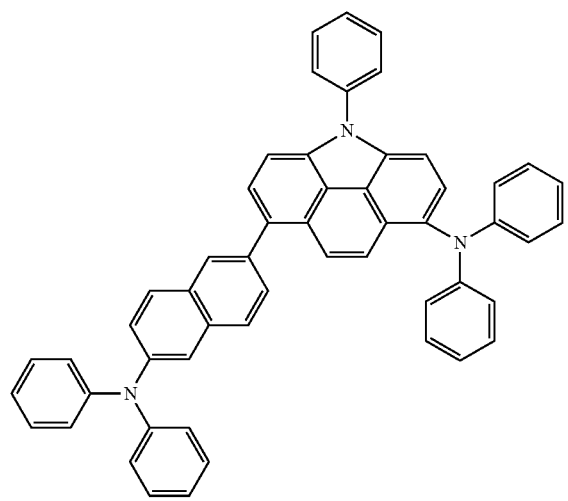
37
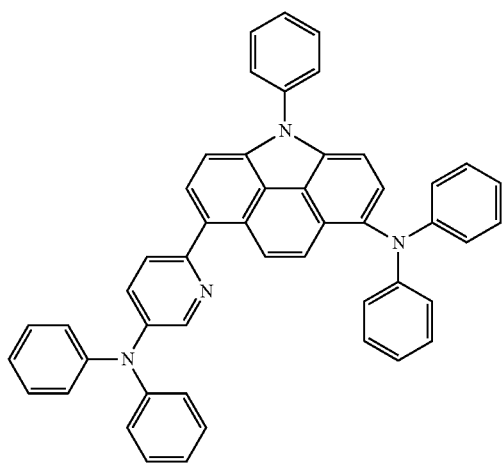

-continued
38
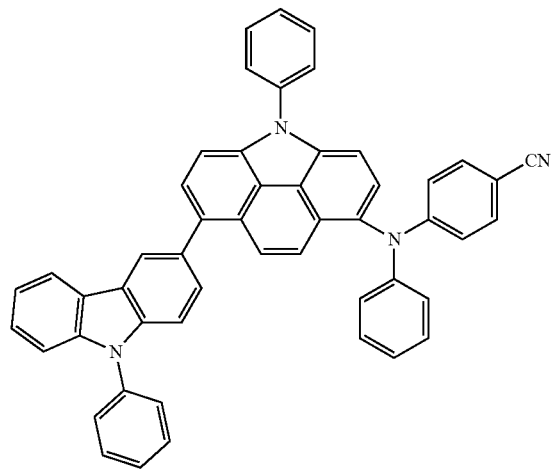
39
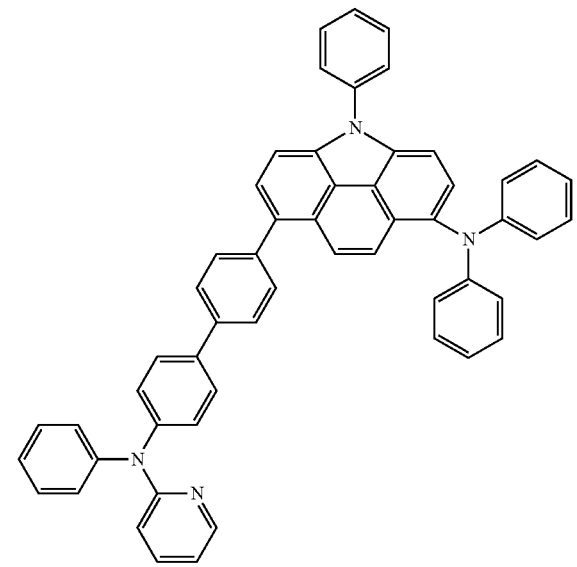
40
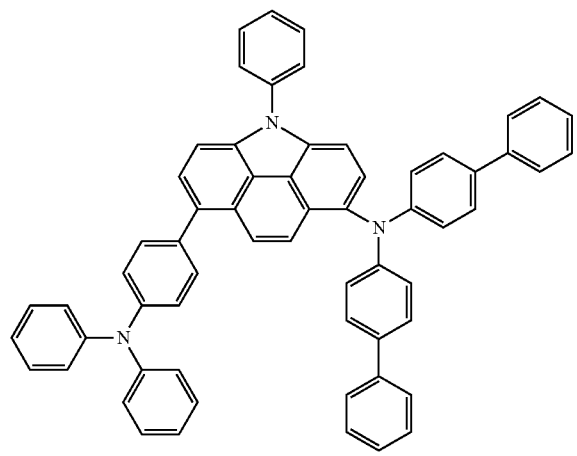
41
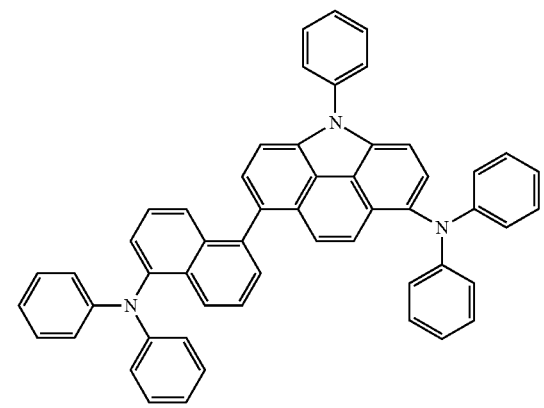
42
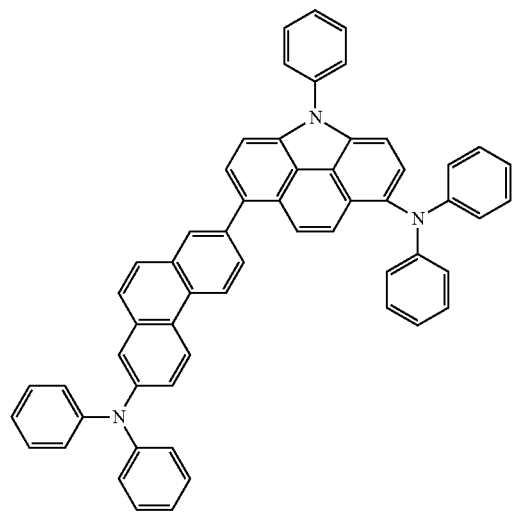
43
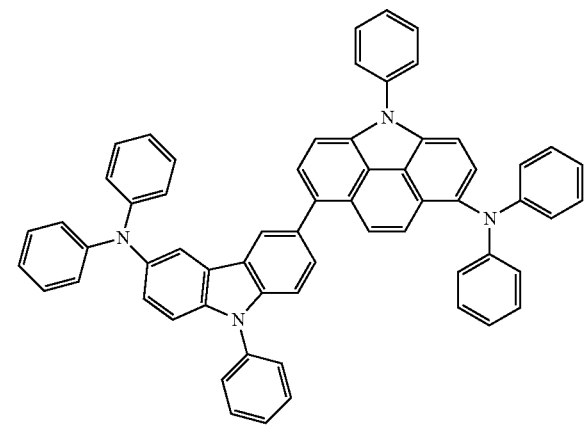

-continued
44
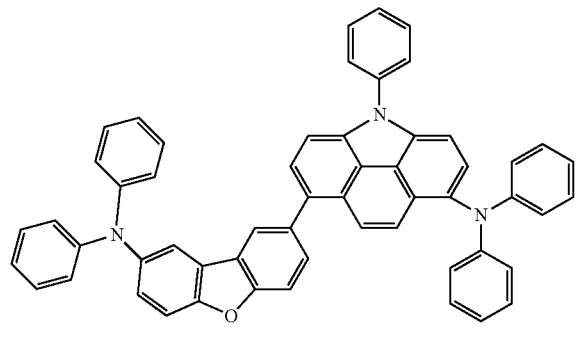
45
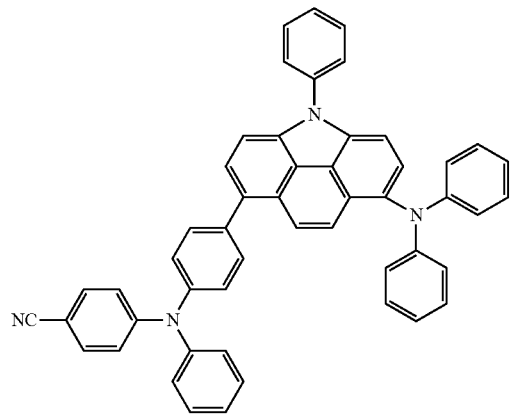
46
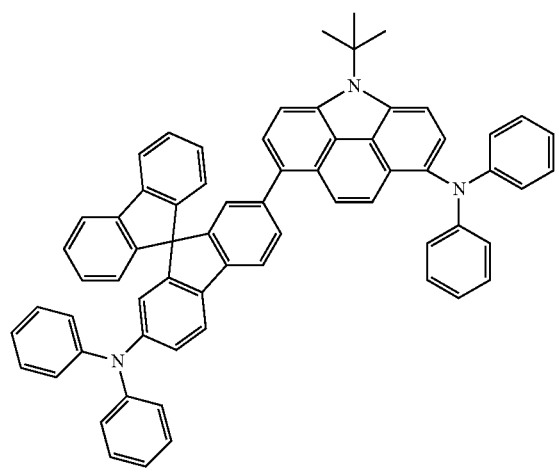
47
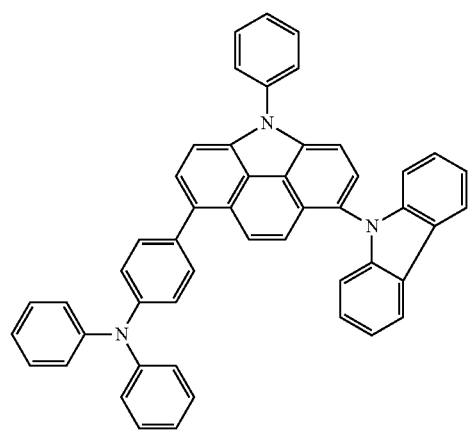
48
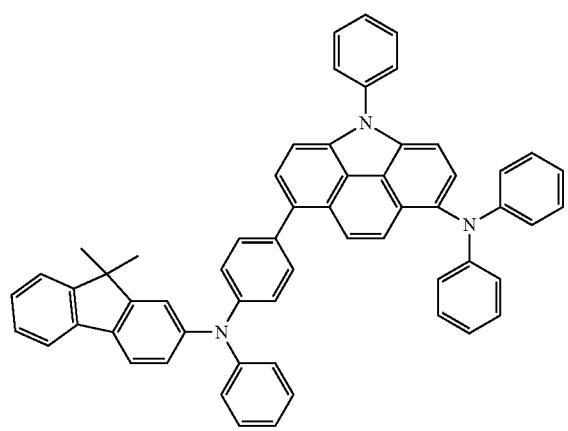
49
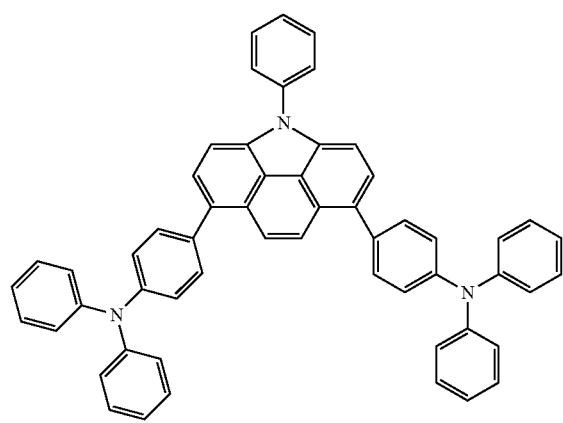

-continued
50
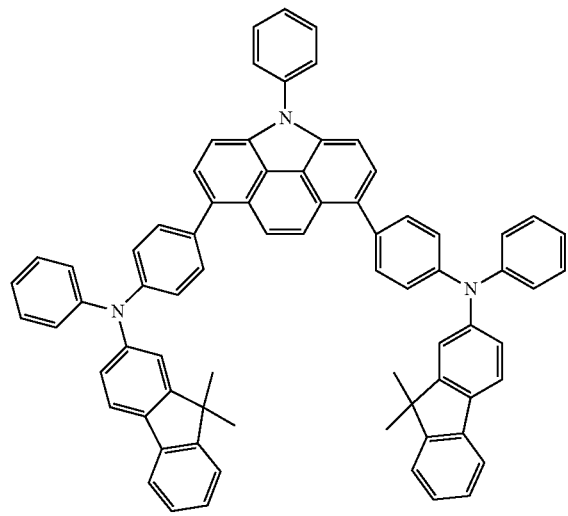
51
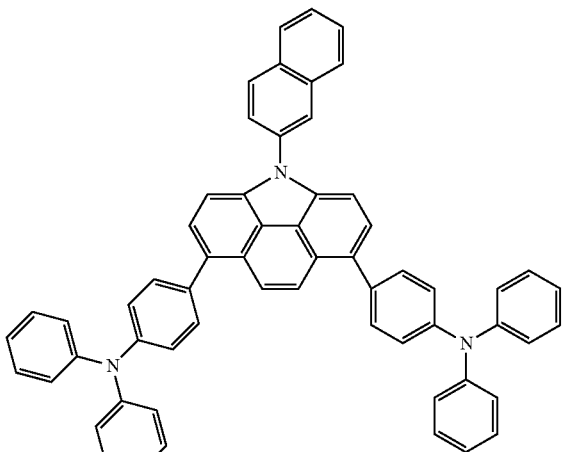
52
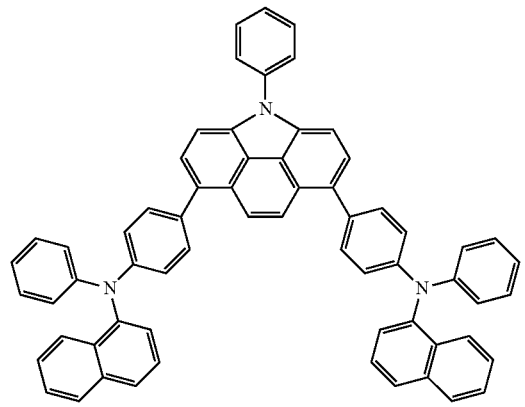
53
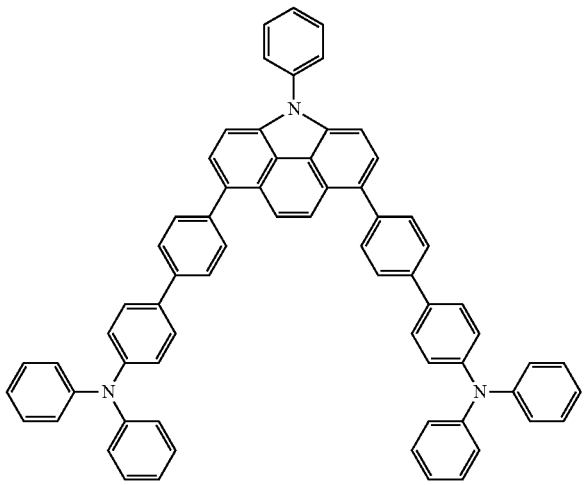
54
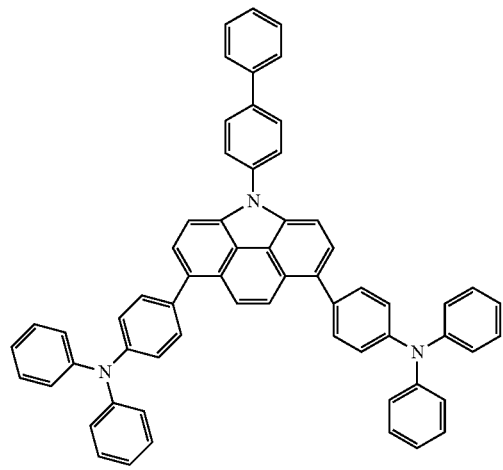
55
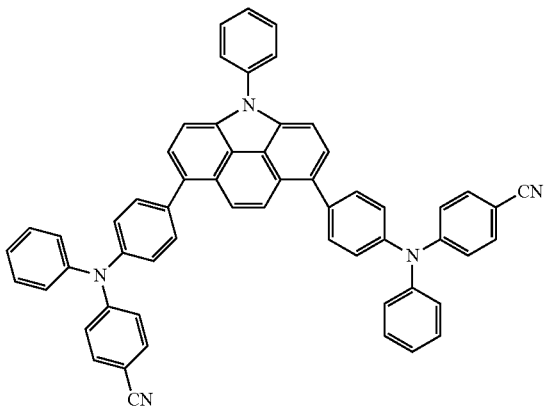

-continued
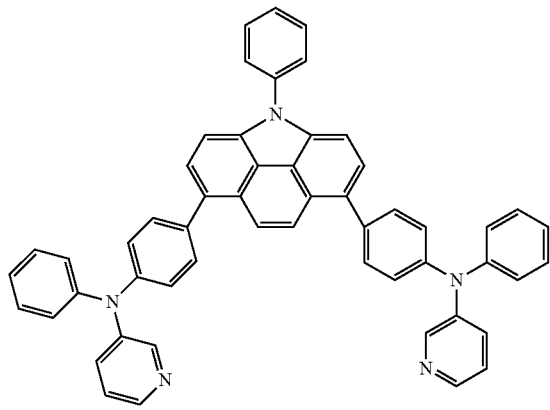
56
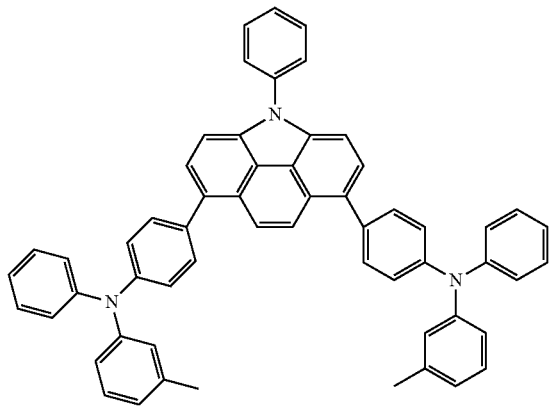
57
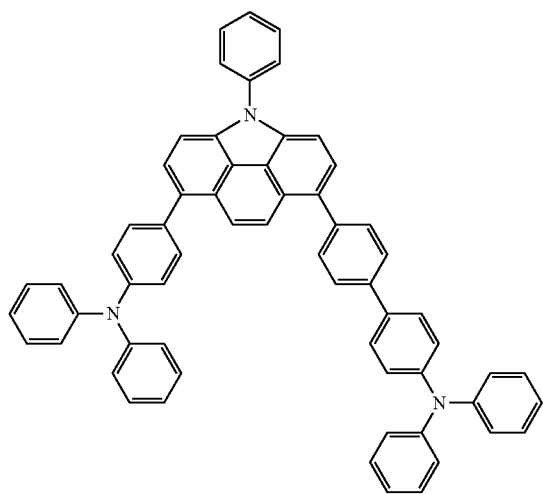
58
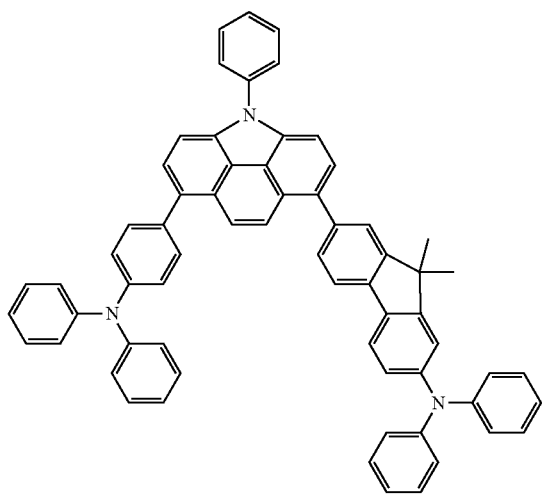
59
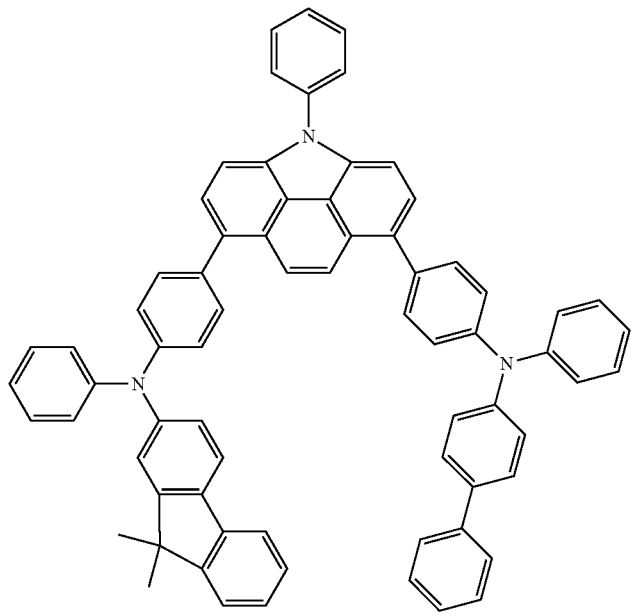
60

Another embodiment provides an organic light-emitting device including a first electrode, a second electrode, and an organic layer disposed between the first electrode and the second electrode, wherein the organic layer includes the compound represented by Formula 1 described above.

The organic layer may include at least one layer selected from among a hole injection layer, a hole transport layer, a functional layer having both hole injection and hole transport capabilities (hereinafter, "H-functional layer"), a buffer layer, an electron blocking layer, an emission layer, a hole blocking layer, an electron transport layer, an electron injection layer, and a functional layer having both electron injection and electron transport capabilities (hereinafter, "E-functional layer").

In an implementation, the organic layer may be an emission layer, and the compound may used as a host in a fluorescent or phosphorescent device).

In an implementation, the organic light-emitting device may include an electron injection layer, an electron transport layer, an emission layer, a hole injection layer, a hole transport layer, or a functional layer having both hole injection and transport capabilities; and the emission layer may include the compound represented by Formula 1 above, and an anthracene-based compound, an arylamine-based compound or a styryl-based compound.

In an implementation, the organic light-emitting device may include an electron injection layer, an electron transport layer, an emission layer, a hole injection layer, a hole transport layer, or a functional layer having both hole injection and transport capabilities; at least one of a red emission layer, a green emission layer, a blue emission layer, and a white emission layer of the emission layer may include a phosphorescent compound; and at least one of the hole injection layer, the hole transport layer, and the functional layer having both hole injection and hole transport capabilities may further include a charge-generating material, in addition to the compound according to an embodiment. In an implementation, the charge-generating material may be a p-dopant, and the p-dopant may be a quinine derivative, a metal oxide, or a cyano group-containing compound.

In some embodiments, the organic layer may include an electron transport layer, and the electron transport layer may include an electron-transporting organic compound and a meta complex. The metal complex may be a lithium (Li) complex.

The term "organic layer" as used herein refers to a single layer and/or a plurality of layers disposed between the first and second electrodes of the organic light-emitting device.

The organic layer may include an emission layer, and the emission layer may include the compound represented by Formula 1 described above. The organic layer may include at least one of a hole injection layer, a hole transport layer, and a functional layer having both hole injection and hole transport capabilities (hereinafter, "H-functional layer"); and at least one of the hole injection layer, the hole transport layer, and the functional layer having both hole injection and hole transport capabilities may include the compound represented by Formula 1.

The compound in the emission layer (EML) may serve as a host. For example, the compound represented by Formula 1 may serve as a blue fluorescent host emitting blue light. The compound represented by Formula 1 in the emission layer may serve as a fluorescent or phosphorescent dopant emitting red light, green light, or blue light.

FIG. 1 illustrates a schematic sectional view of an organic light-emitting device according to an embodiment. Hereinafter, a structure of an organic light-emitting device according to an embodiment and a method of manufacturing the same will now be described with reference to FIG. 1.

A substrate (not shown) may be a suitable substrate that is used in organic light emitting devices. In some embodiments the substrate may be a glass substrate or a transparent plastic substrate with strong mechanical strength, thermal stability, transparency, surface smoothness, ease of handling, and water resistance.

The first electrode may be formed by depositing or sputtering a first electrode-forming material on the substrate. When the first electrode is an anode, a material having a high work function may be used as the first electrode-forming material to facilitate hole injection. The first electrode may be a reflective electrode or a transmission electrode. Transparent and conductive materials such as ITO, IZO, $SnO_2$, and ZnO may be used to form the first electrode. The first electrode may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode may have a single-layer structure or a multi-layer structure including at least two layers. For example, the first electrode may have a three-layered structure of ITO/Ag/ITO, but is not limited thereto.

An organic layer is disposed on the first electrode.

The organic layer may include at least one of a hole injection layer (HIL), a hole transport layer (HTL), a buffer layer (not shown), an emission layer (EML), an electron transport layer (ETL), or an electron injection layer (EIL).

The HIL may be formed on the first electrode by vacuum deposition, spin coating, casting, Langmuir-Blodgett (LB) deposition, or the like.

When the HIL is formed using vacuum deposition, vacuum deposition conditions may vary according to the material that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using spin coating, the coating conditions may vary according to the compound that is used to form the HIL, and the desired structure and thermal properties of the HIL to be formed. For example, the coating rate may be in the range of about 2,000 rpm to about 5,000 rpm, and a temperature at which heat treatment is performed to remove a solvent after coating may be in the range of about 80° C. to about 200° C. However, the coating conditions are not limited thereto.

The HIL may be formed of the compound represented by Formula 1, or a suitable material to form a HIL. Non-limiting examples of the material that can be used to form the HIL may include N,N'-diphenyl-N,N'-bis-[4-(phenyl-m-tolyl-amino)-phenyl]-biphenyl-4,4'-diamine, (DNTPD), a phthalocyanine compound such as copperphthalocyanine, 4,4',4"-tris (3-methylphenylphenylamino)triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly (4-styrenesulfonate) (PEDOT/PSS), polyaniline/camphor sulfonicacid (Pani/CSA), and polyaniline/poly(4-styrene-sulfonate (PANI/PSS).

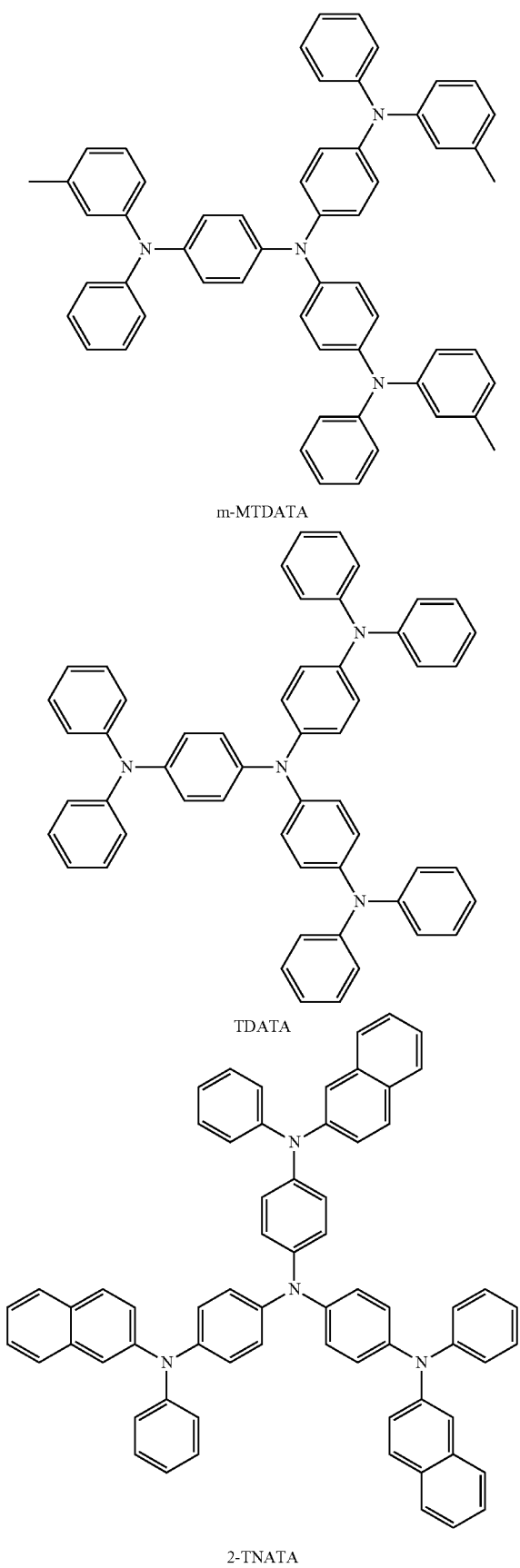

m-MTDATA

TDATA

2-TNATA

The thickness of the HIL may be from about 100 Å to about 10,000 Å, and in some embodiments, from about 100 Å to about 1,000 Å. When the thickness of the HIL is within these ranges, the HIL may have good hole injecting ability without a substantial increase in driving voltage.

Then, a HTL may be formed on the HIL by using vacuum deposition, spin coating, casting, Langmuir-Blodgett (LB) deposition, or the like. When the HTL is formed using vacuum deposition or spin coating, the conditions for deposition and coating may be similar to those for the formation of the HIL, though the conditions for the deposition and coating may vary according to the material that is used to form the HTL.

The HTL may be formed of the compound represented by Formula 1, or suitable hole transporting materials. Non-limiting examples of suitable HTL forming materials may include carbazole derivatives, such as N-phenylcarbazole or polyvinylcarbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), and N,N'-di(1-naphthyl)-N,N'-diphenylbenzidine) (NPB).

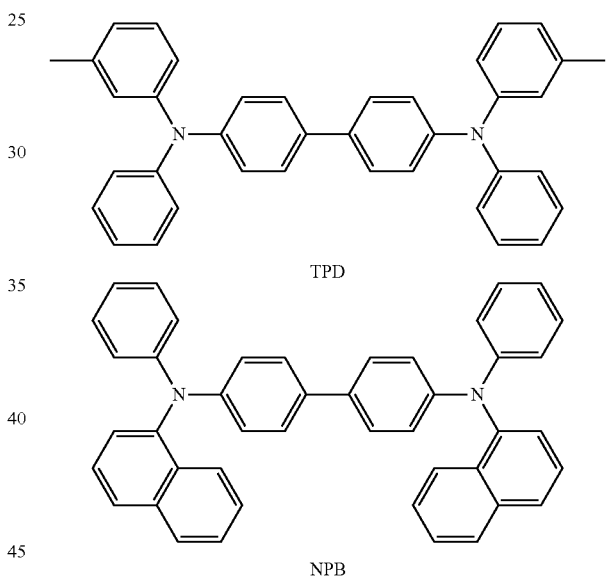

TPD

NPB

The thickness of the HTL may be from about 50 Å to about 2,000 Å, and in some embodiments, from about 100 Å to about 1,500 Å. When the thickness of the HTL is within these ranges, the HTL may have good hole transporting ability without a substantial increase in driving voltage.

The H-functional layer (having both hole injection and hole transport capabilities) may contain at least one material from each group of the hole injection layer materials and hole transport layer materials. The thickness of the H-functional layer may be from about 500 Å to about 10,000 Å, and in some embodiments, may be from about 100 Å to about 1,000 Å. When the thickness of the H-functional layer is within these ranges, the H-functional layer may have good hole injection and transport capabilities without a substantial increase in driving voltage.

In some embodiments, at least one of the HIL, HTL, and H-functional layer may include at least one of a compound represented by Formula 300, below, or a compound represented by Formula 350, below:

<Formula 300>

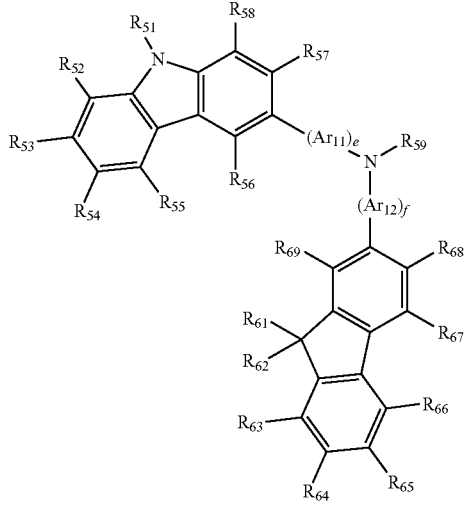

<Formula 350>

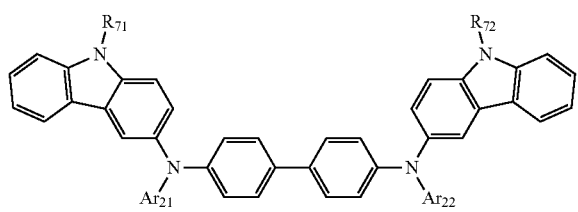

In Formulae 300 and 350, $Ar_{11}$, $Ar_{12}$, $Ar_{21}$, and $Ar_{22}$ may be each independently a substituted or unsubstituted $C_5$-$C_{60}$ arylene group.

In Formula 300, e and f may be each independently an integer from 0 to 5, for example, may be 0, 1, or 2. In a non-limiting embodiment, e may be 1, and f may be 0.

In Formulae 300 and 350 above, $R_{51}$ to $R_{58}$, $R_{61}$ to $R_{69}$, and $R_{71}$ to $R_{72}$ may be each independently a hydrogen atom, a deuterium atom, a halogen atom, a hydroxyl group, a cyano group, a nitro group, an amino group, an amidino group, a hydrazine group, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group. In some embodiments, $R_{51}$ to $R_{58}$, $R_{61}$ to $R_{69}$, $R_{71}$, and $R_{72}$ may be each independently one of a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like); a $C_1$-$C_{10}$ alkyl group and a $C_1$-$C_{10}$ alkoxy group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof; a phenyl group; a naphthyl group; an anthryl group; a fluorenyl group; a pyrenyl group; and a phenyl group, a naphthyl group, an anthryl group, a fluorenyl group, and a pyrenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group.

In Formula 300, $R_{59}$ may be one of a phenyl group, a naphthyl group, an anthryl group, a biphenyl group, a pyridyl group; and a phenyl group, a naphthyl group, an anthryl group, a biphenyl group, and a pyridyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{20}$ alkyl group, and a substituted or unsubstituted $C_1$-$C_{20}$ alkoxy group.

In an embodiment the compound represented by Formula 300 may be a compound represented by Formula 300A below:

<Formula 300A>

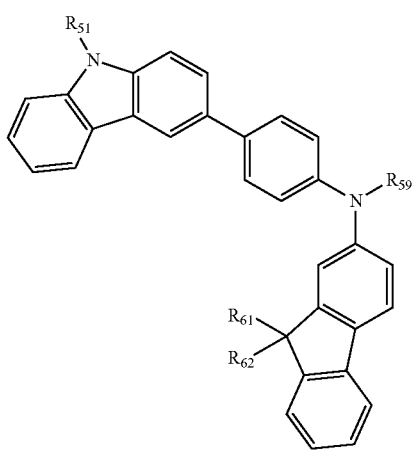

In Formula 300A, $R_{51}$, $R_{60}$, $R_{61}$, and $R_{59}$ may be as defined above.

In some non-limiting embodiments, at least one of the HIL, HTL, and H-functional layer may include at least one of compounds represented by Formulae 301 to 320 below:

33    34
301
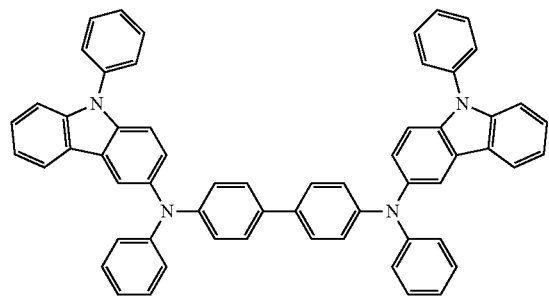
302
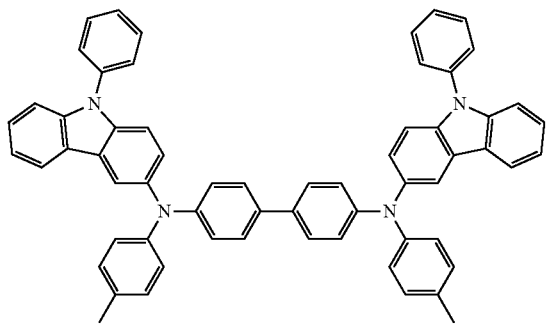
303
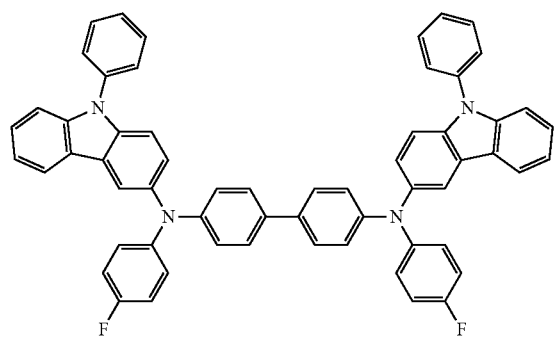
304
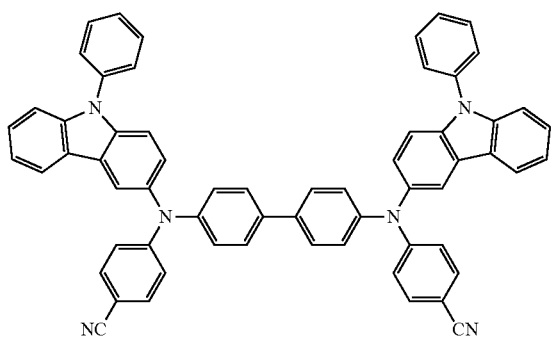
305
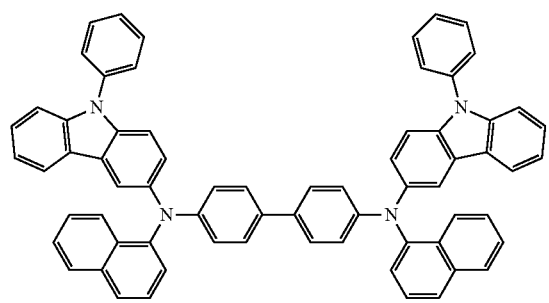
306
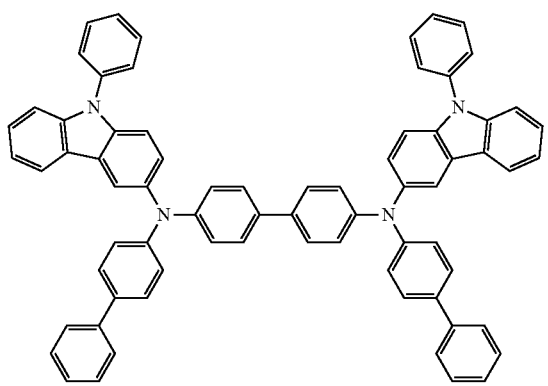
307
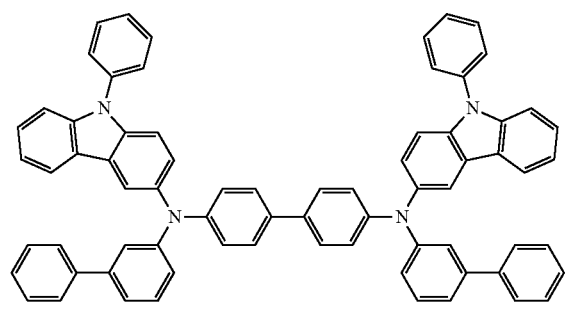
308
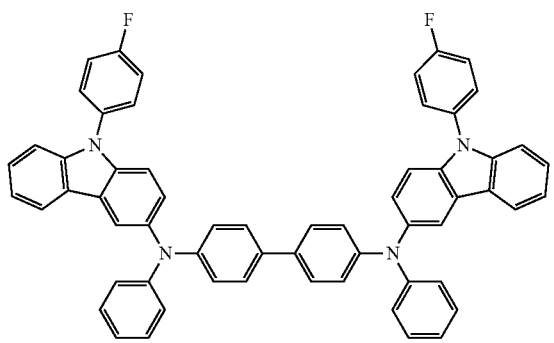

309
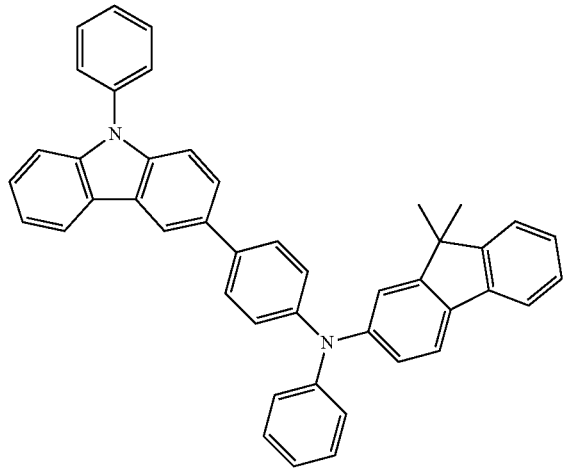
310
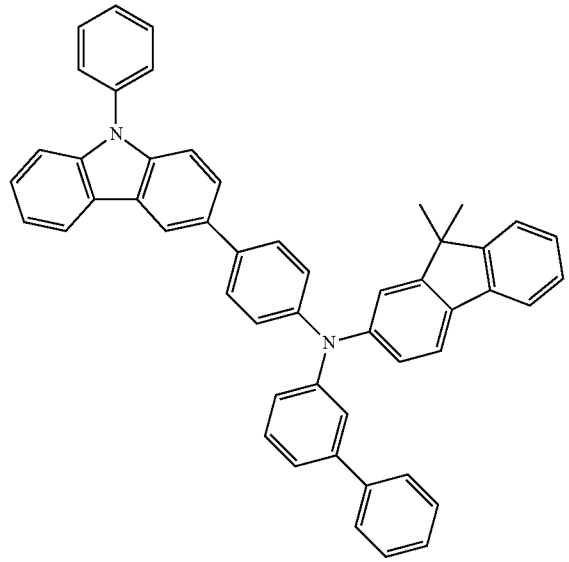
311
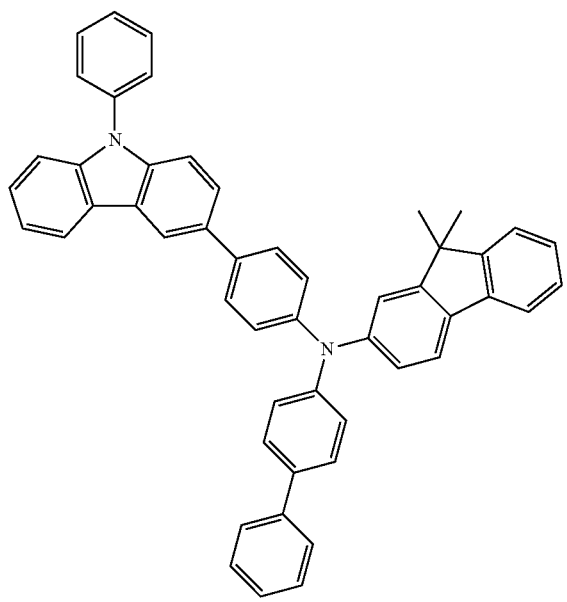
312
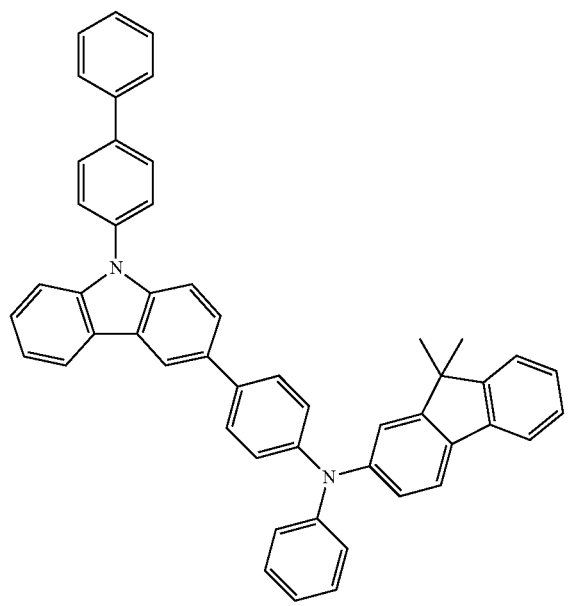

313
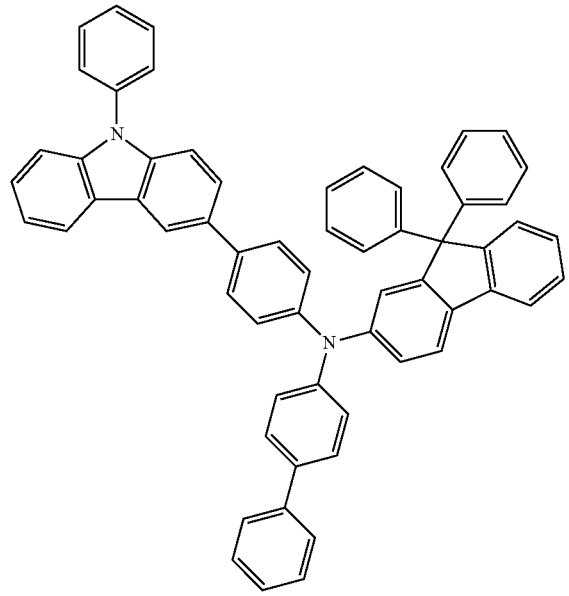
314
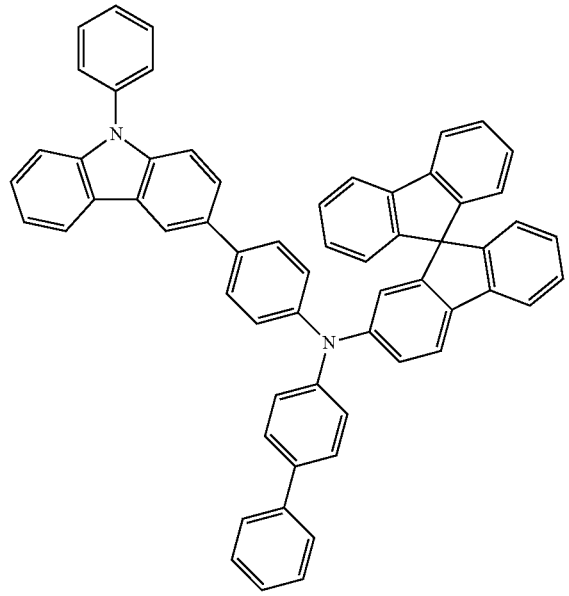
315
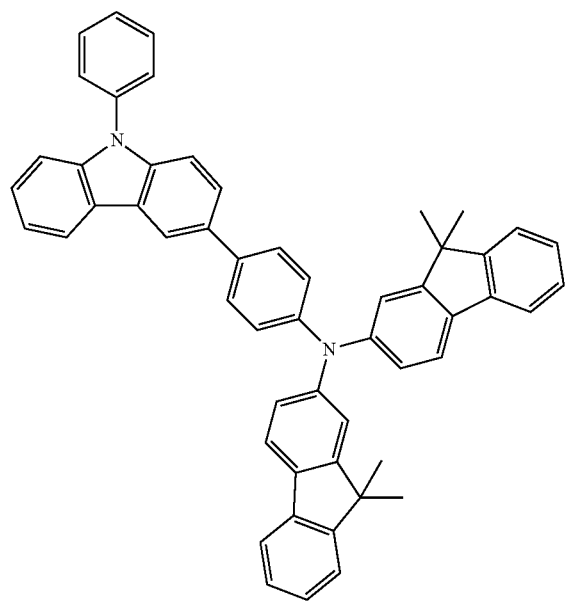
316
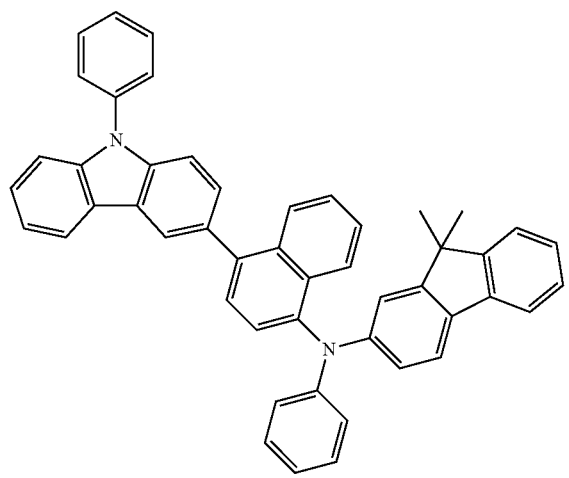

-continued

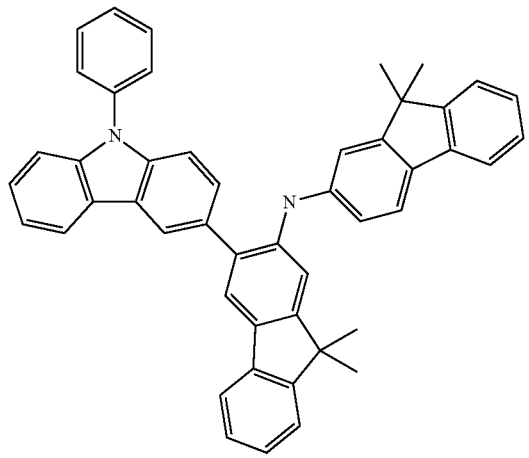
317

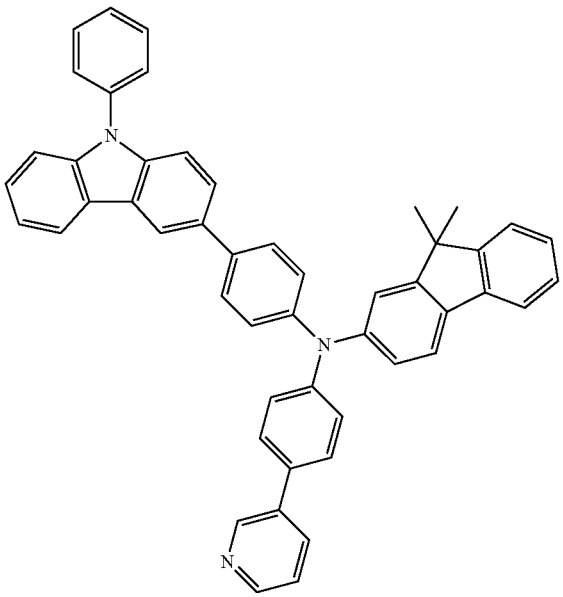
318

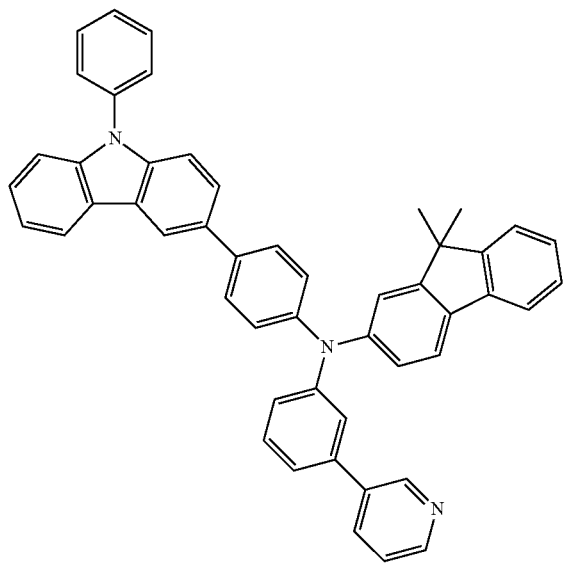
319

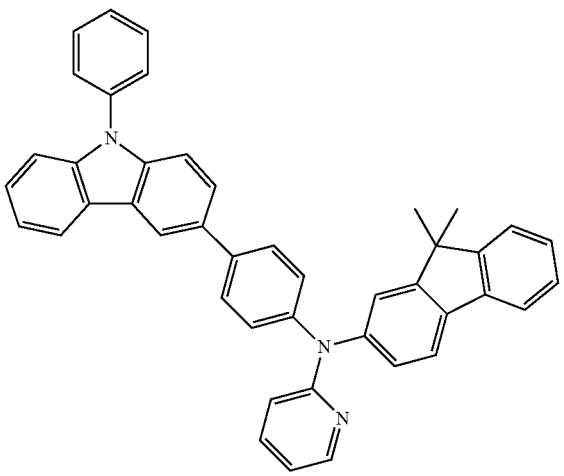
320

At least one of the HIL, HTL, and H-functional layer may further include a charge-generating material for improved layer conductivity, in addition to a suitable hole injecting material, hole transport material, and/or material having both hole injection and hole transport capabilities as described above.

The charge-generating material may be, for example, a p-dopant. The p-dopant may be one of quinine derivatives, metal oxides, and compounds with a cyano group, but are not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-CTNQ), and the like; metal oxides such as tungsten oxide, molybdenum oxide, and the like; and cyano-containing compounds such as Compound 200 below.

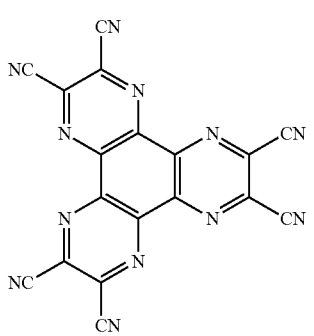

<Compound 200>

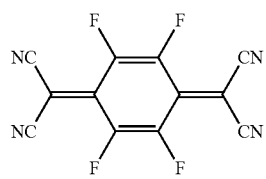

<F4-CTNQ>

When the hole injection layer, hole transport layer, or H-functional layer further includes a charge-generating material, the charge-generating material may be homogeneously dispersed or heterogeneously distributed in the layer.

A buffer layer may be disposed between at least one of the HIL, HTL, and H-functional layer, and the EML. The buffer layer may compensate for an optical resonance distance of light according to a wavelength of the light emitted from the EML, and thus may increase efficiency. The buffer layer may include a suitable hole injecting material or hole transporting material. In some other embodiments, the buffer layer may include the same material as one of the materials included in the HIL, HTL, and H-functional layer that underlie the buffer layer.

Then, an EML may be formed on the HTL, H-functional layer, or buffer layer by vacuum deposition, spin coating, casting, Langmuir-Blodget (LB) deposition, or the like. When the EML is formed using vacuum deposition or spin coating, the deposition and coating conditions may be similar to those for the formation of the HIL, though the conditions for deposition and coating may vary according to the material that is used to form the EML.

The EML may include the compound represented by Formula 1. For example, the compound represented by Formula 1 may be used as a host or a dopant. The EML may be formed using a variety of suitable light-emitting materials, in addition to the compound represented by Formula 1. In some embodiments, the EML may also be formed using a suitable host and a dopant. Dopants that may be used to form the EML may include a suitable fluorescent dopant or a suitable phosphorescent dopant.

Non-limiting examples of the host may include Alq$_3$, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di-2-naphthylanthracene (TBADN), E3, distyrylarylene (DSA), dmCBP (see a formula below), and Compounds 501 to 509 below.

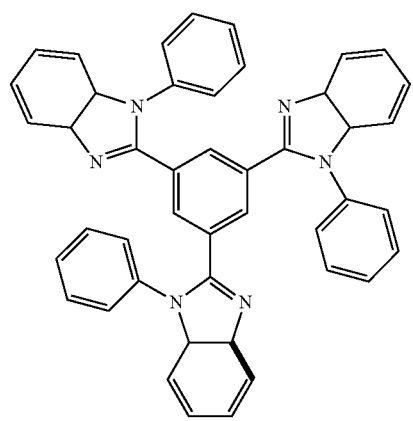

TPBI

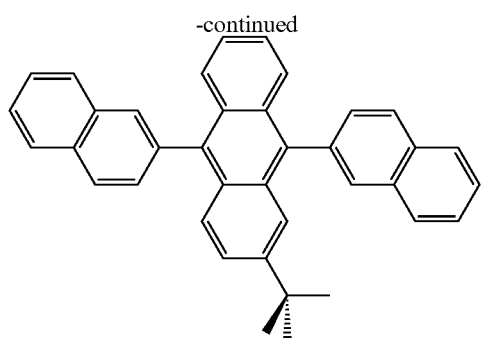

TBADN

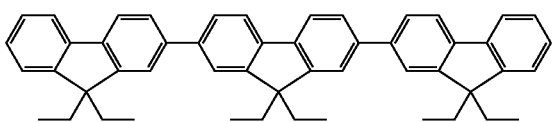

E3

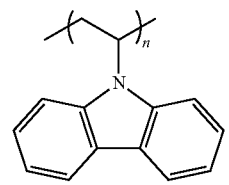

PVK

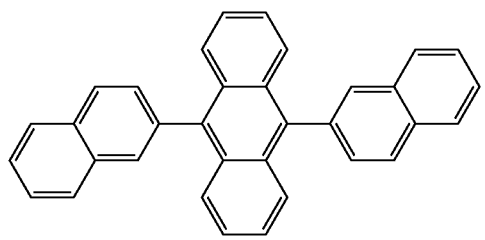

ADN

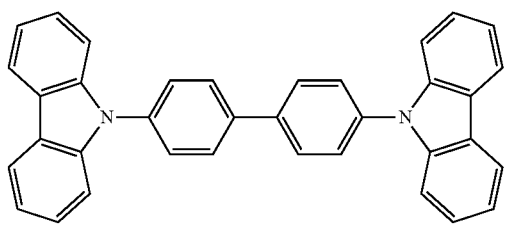

CBP

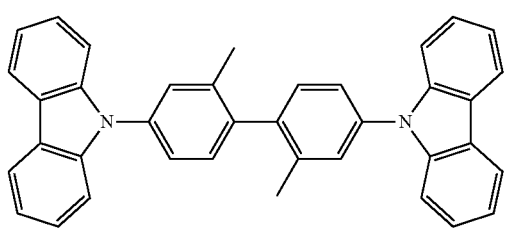

dmCBP

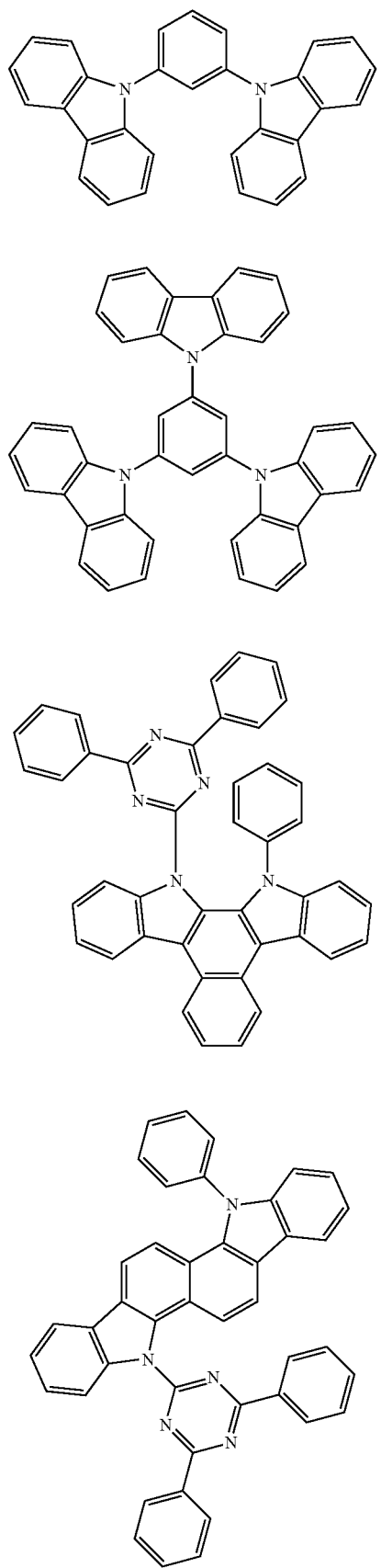
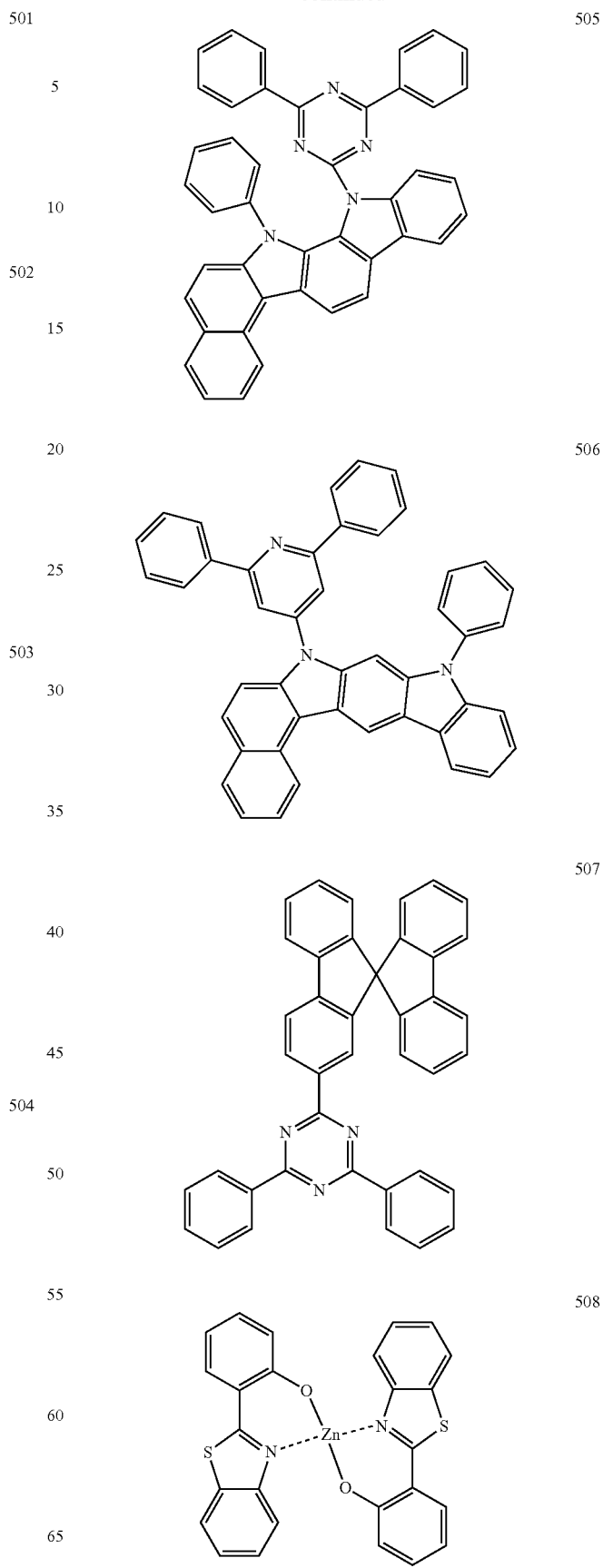

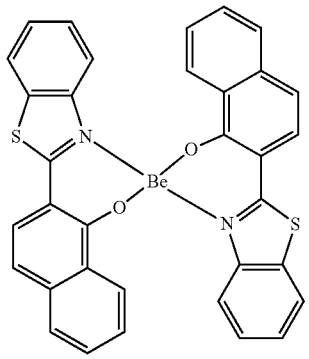

In some embodiments, an anthracene-based compound represented by Formula 400 below may be used as the host.

<Formula 400>

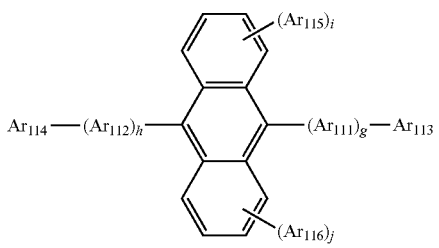

In Formula 400, $Ar_{111}$ and $Ar_{112}$ may be each independently a substituted or unsubstituted $C_5$-$C_{60}$arylene group; $Ar_{113}$ to $Ar_{116}$ may be each independently a substituted or unsubstituted $C_1$-$C_{10}$alkyl group, or a substituted or unsubstituted C5-$C_{60}$aryl group; and g, h, i, and j may be each independently an integer from 0 to 4.

In some non-limiting embodiments, $Ar_{111}$ and $Ar_{112}$ in Formula 400 may be each independently a phenylene group, a naphthylene group, a phenanthrenylene group, or a pyrenylene group; or a phenylene group, a naphthylene group, a phenanthrenylene group, a fluorenyl group, or a pyrenylene group that are substituted with at least one of a phenyl group, a naphthyl group, and an anthryl group.

In Formula 400 above, g, h, I, and j may be each independently 0, 1, or 2.

In Formula 400, $Ar_{113}$ to $Ar_{116}$ may be each independently one of a $C_1$-$C_{10}$alkyl group that is substituted with at least one of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, and a fluorenyl group that are substituted with at least one of a deuterium atom, a halogen atom, a hydroxyl group, a cyano group, a nitro group, an amino group, an amidino group, a hydroxyrazine, a hydroxyrazone, a carboxyl group or a salt thereof, a sulfonic acid group or a salt thereof, a phosphoric acid group or a salt thereof, a $C_1$-$C_{60}$alkyl group, a $C_2$-$C_{60}$alkenyl group, a $C_2$-$C_{60}$alkynyl group, a $C_1$-$C_{60}$alkoxy group, a phenyl group, a naphthyl group, an anthryl group, a pyrenyl group, a phenanthrenyl group, and a fluorenyl group; and

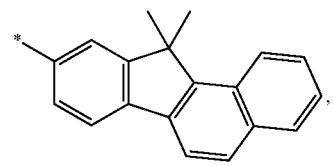 [SMILES: *c1ccc2c(c1)C(C)(C)c1c-2ccc2ccccc12]

but are not limited thereto.

For example, the anthracene-based compound represented by Formula 400 above may be one of the compounds represented by the following formulae, but is not limited thereto.

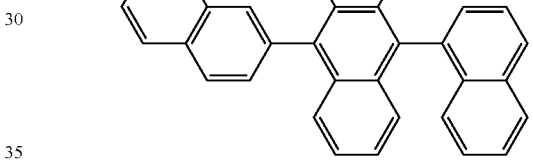

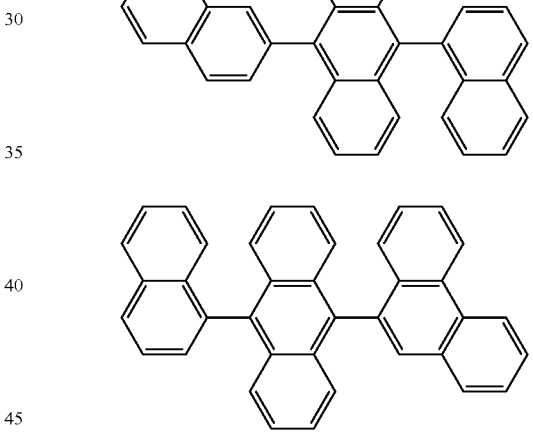

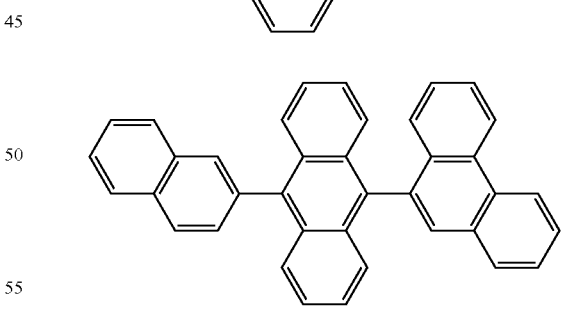

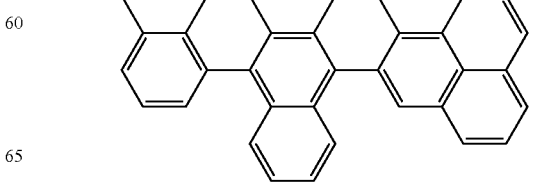

-continued

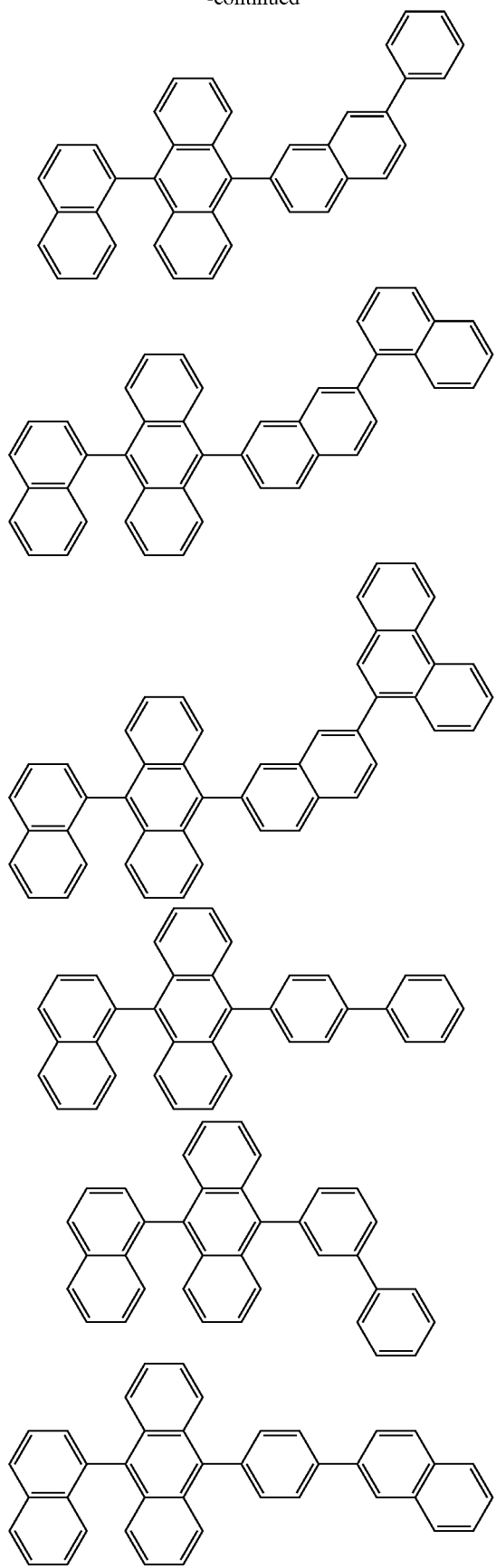
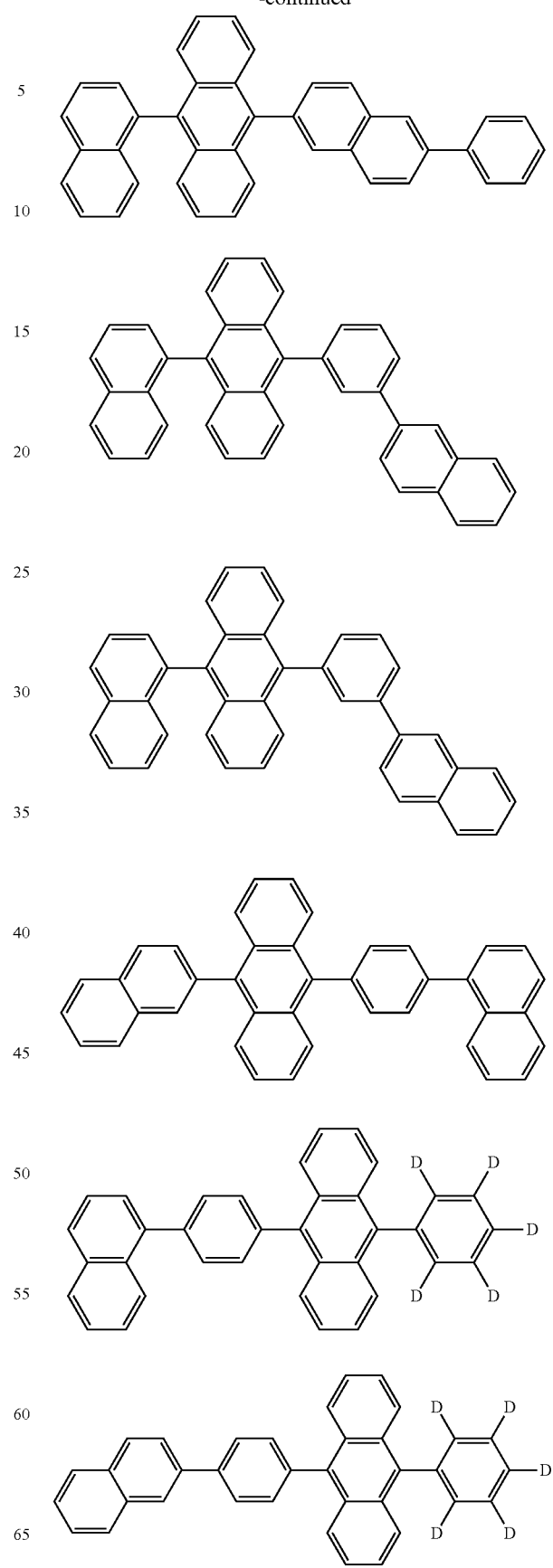

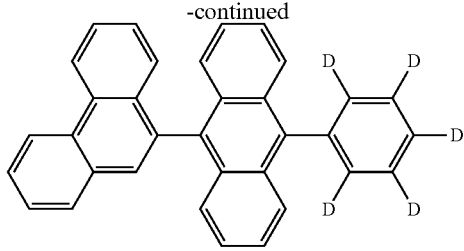
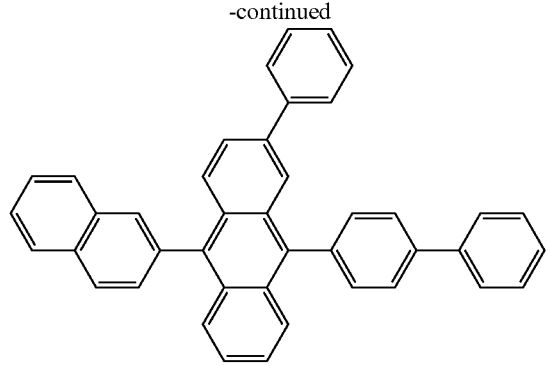
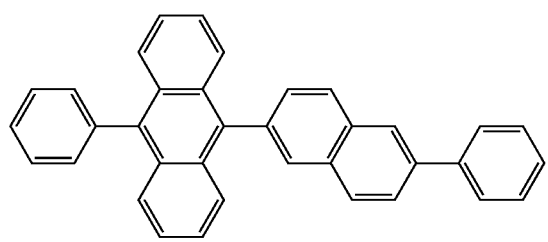
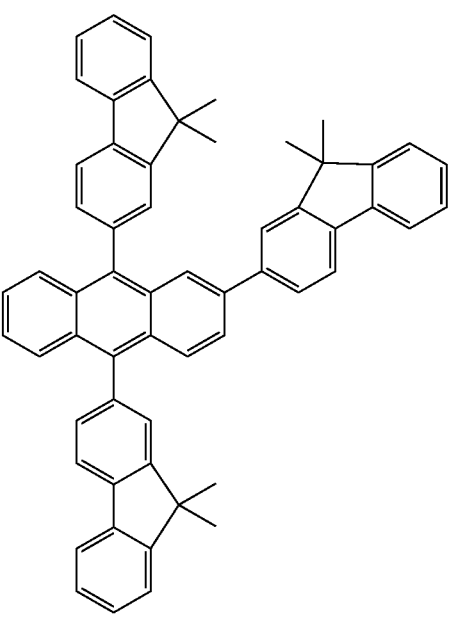
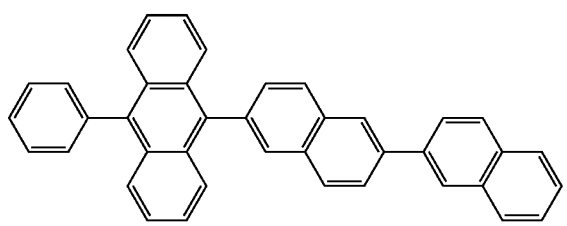
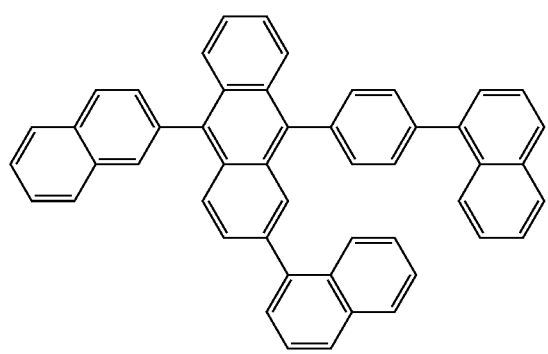
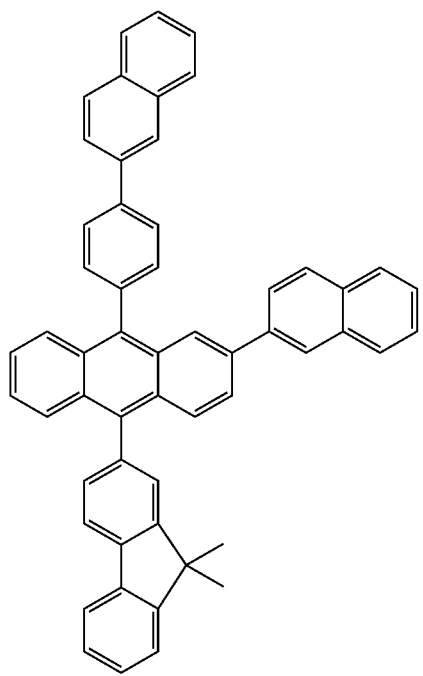
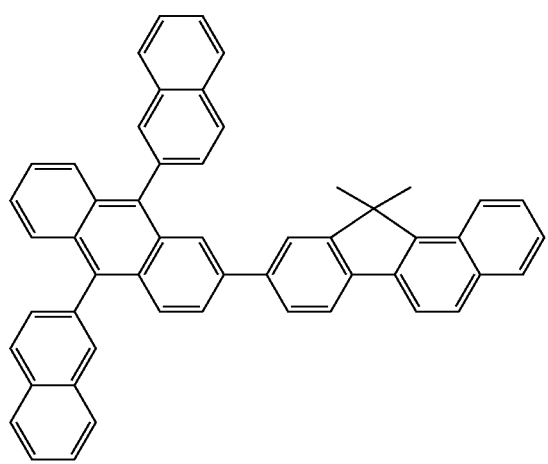

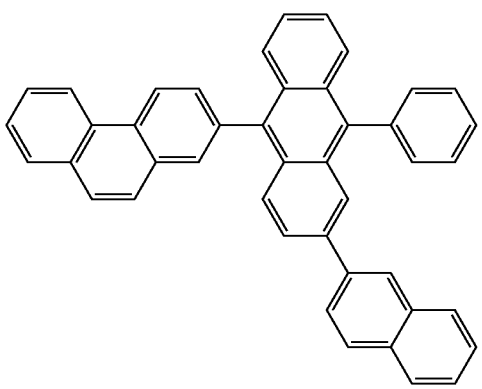

In some embodiments, an anthracene-based compound represented by Formula 401 below may be used as the host.

<Formula 401>

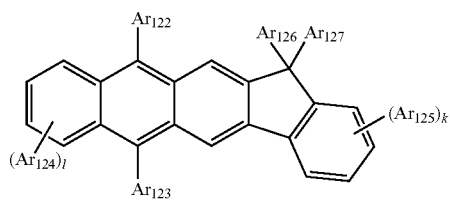

$Ar_{122}$ to $Ar_{125}$ in Formula 401 above may be defined as described above in conjunction with $Ar_m$ of Formula 400, and thus repeated detailed descriptions thereof are omitted.

$Ar_{126}$ and $Ar_{127}$ in Formula 401 above may be each independently a $C_1$-$C_{10}$ alkyl group, for example, a methyl group, an ethyl group, or a propyl group.

In Formula 401, k and l may be each independently an integer from 0 to 4, for example, 0, 1, or 2.

For example, the anthracene-based compound represented by Formula 401 above may be one of the compounds represented by the following formulae, but is not limited thereto:

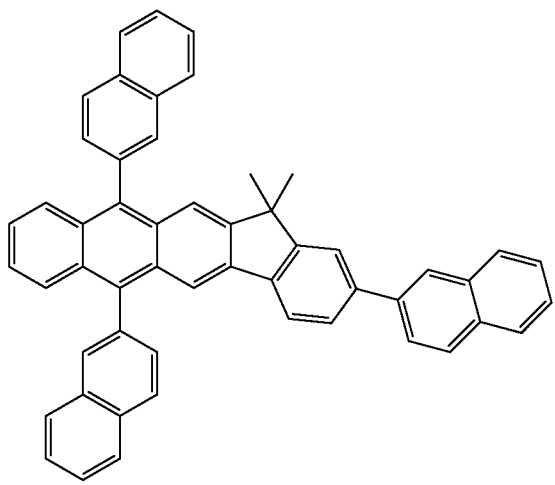

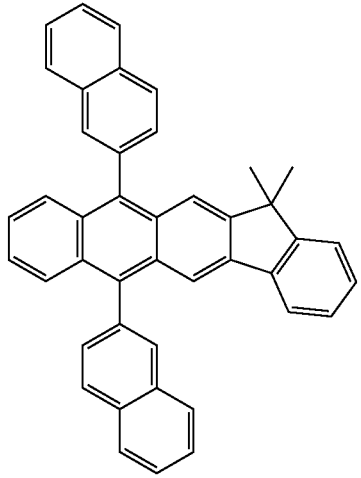

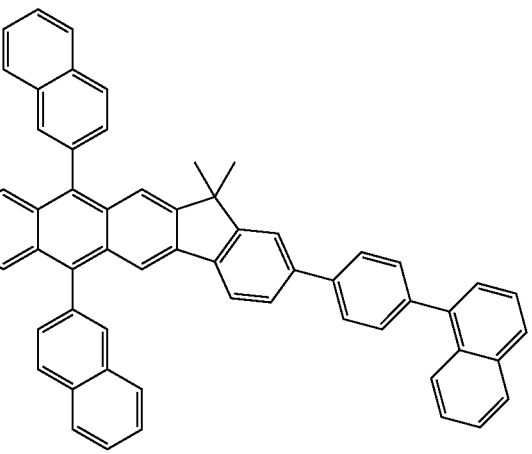

When the organic light-emitting device is a full color organic light-emitting device, the emission layer may be patterned into a red emission layer, a green emission layer, and a blue emission layer.

At least one of the red EML, the green EML, and the blue EML may include a dopant below (ppy=phenylpyridine).

Non-limiting examples of the blue dopant may include compounds represented by the following formulae.

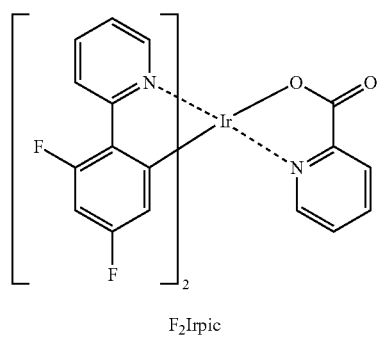
F₂Irpic
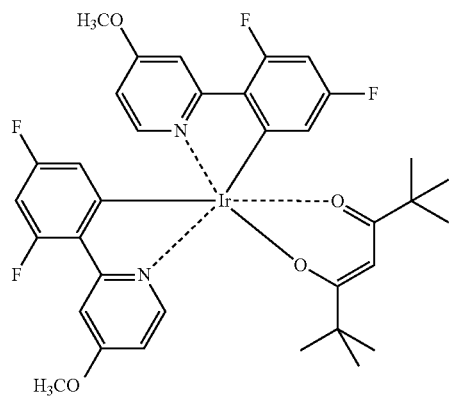
(F2ppy)2Ir(tmd)
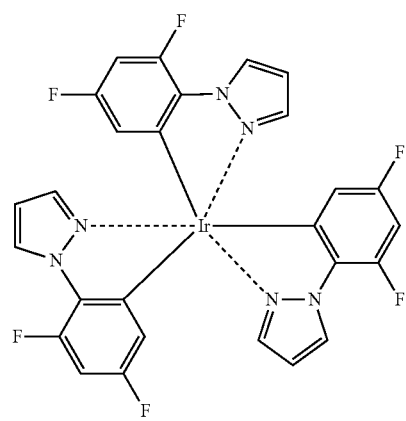
Ir(dfppz)₃
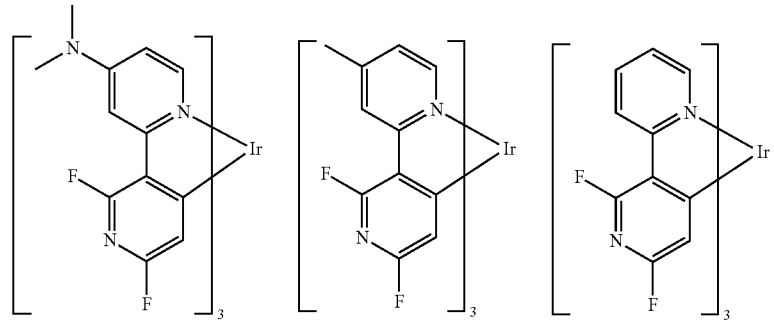
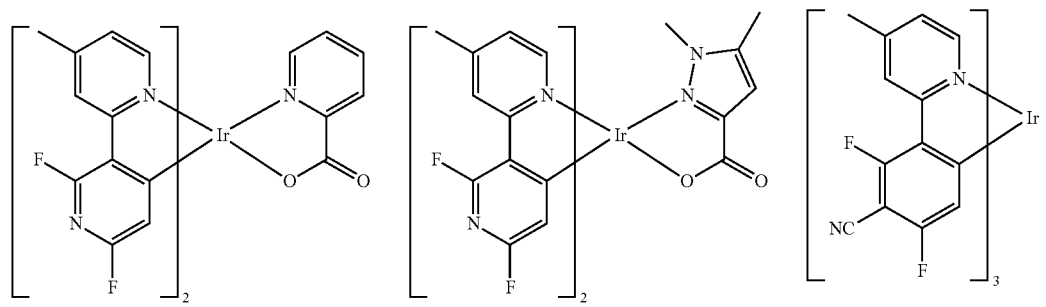
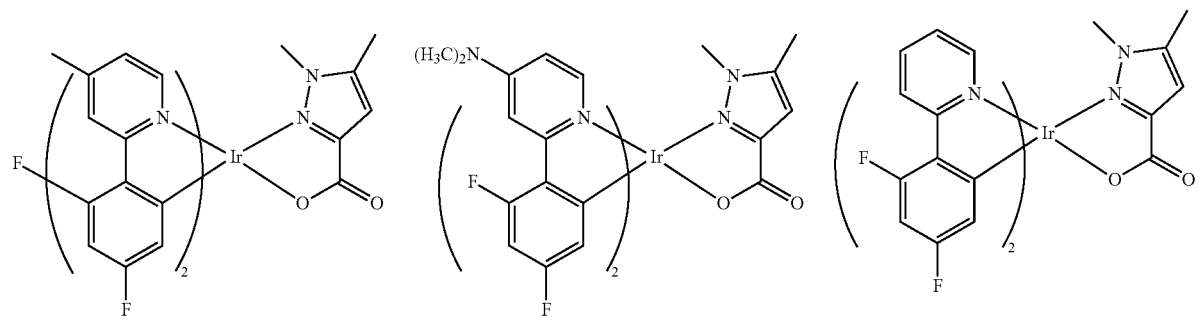

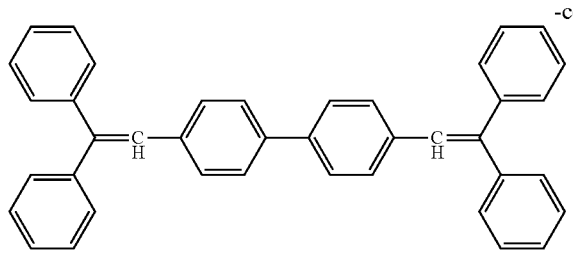
DPVBi
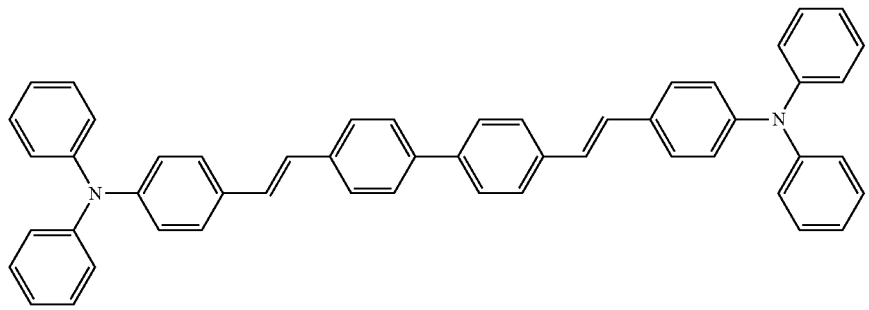
DPAVBi
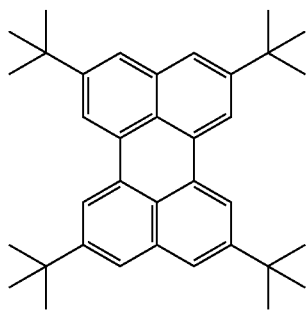
TBPe
Non-limiting examples of the red dopant may include compounds represented by the following formulae.
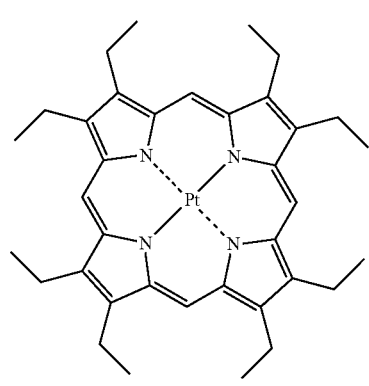
PtOEP
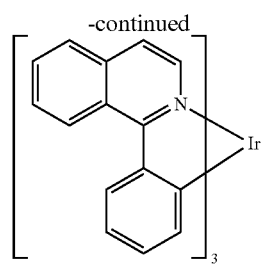
Ir(piq)₃
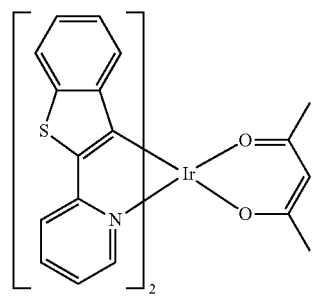
Btp₂Ir(acac)

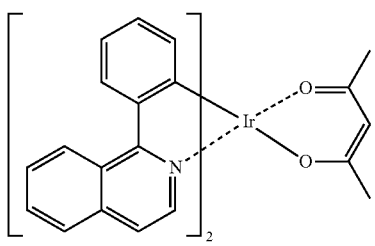
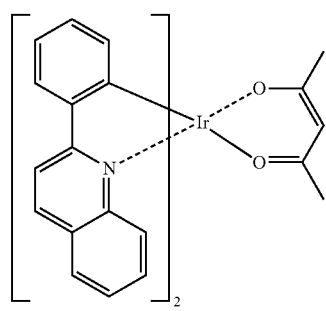
Ir(pq)₂(acac)
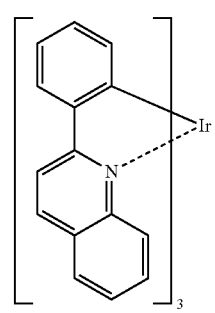
Ir(2-phq)₃
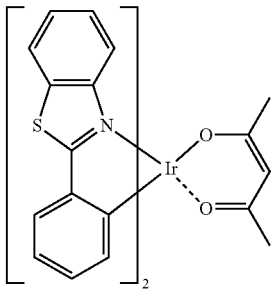
Ir(BT)₂(acac)
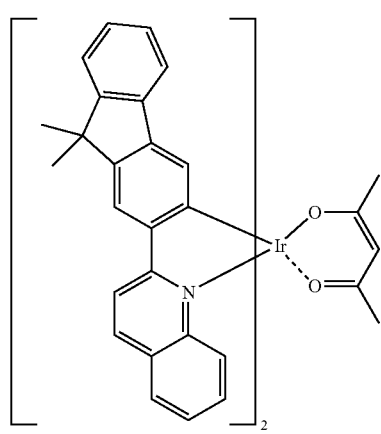
Ir(flq)₂(acac)
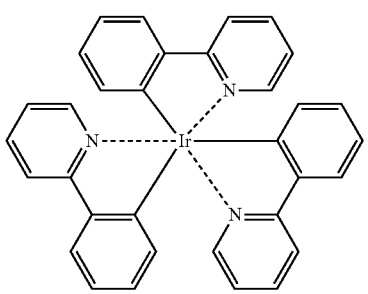
Ir(fliq)₂(acac)
DCM
DCJTB
Non-limiting examples of the green dopant may include compounds represented by the following formulae.
Ir(ppy)₃

-continued
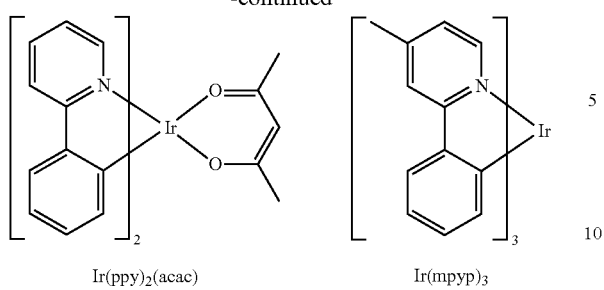
Ir(ppy)₂(acac)    Ir(mpyp)₃
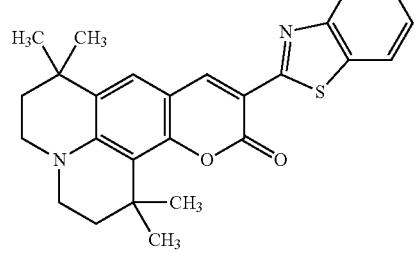
C545T
Non-limiting examples of the dopant that may be used in the EML may include Pt complexes represented by the following formulae D1 to D50.
D1
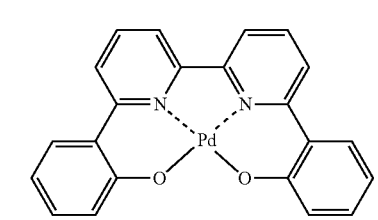
D2
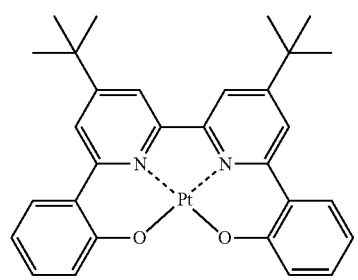
D3
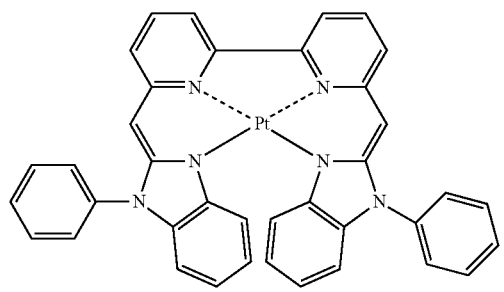
-continued
D4
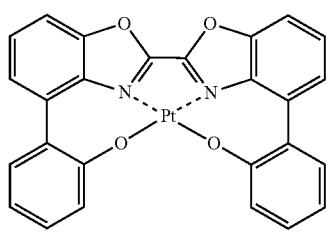
D5
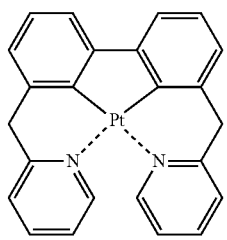
D6
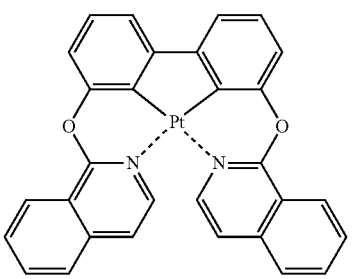
D7
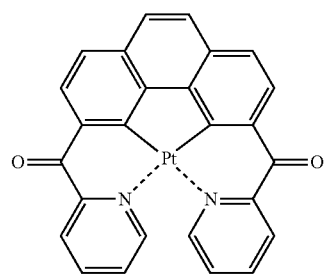
D8
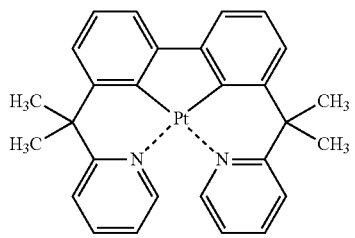
D9
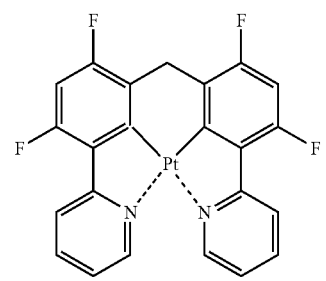

US 9,246,109 B2
63
-continued
D10
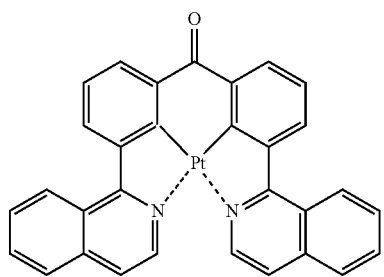
D11
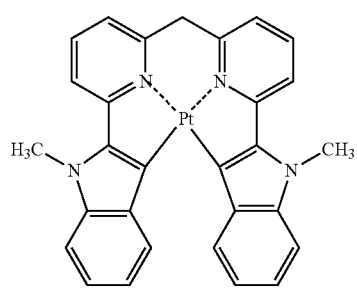
D12
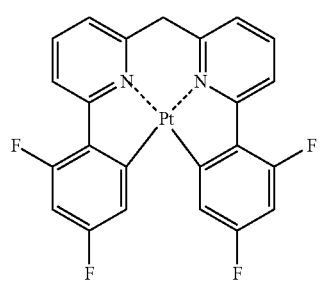
D13
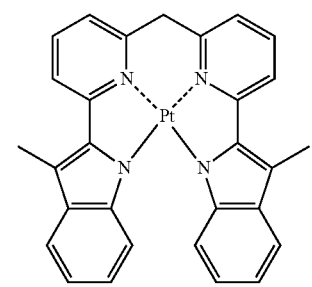
D14
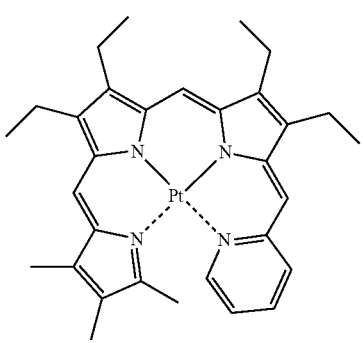
64
-continued
D15
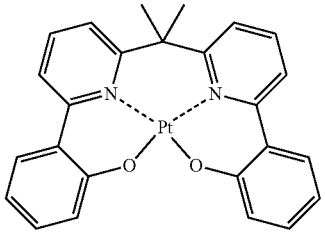
D16
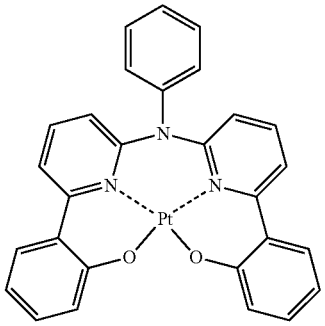
D17
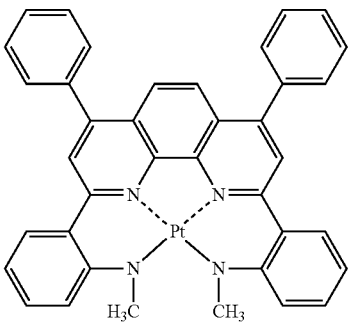
D18
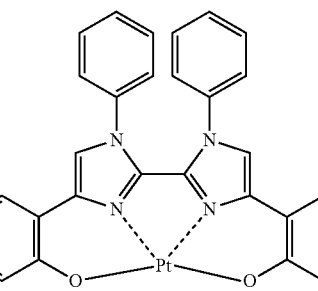
D19
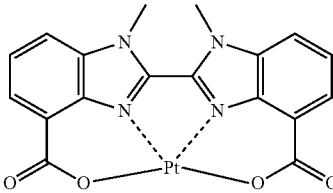
D20
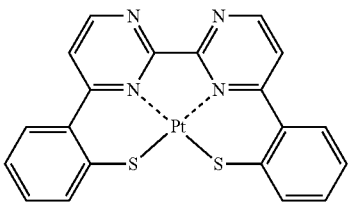

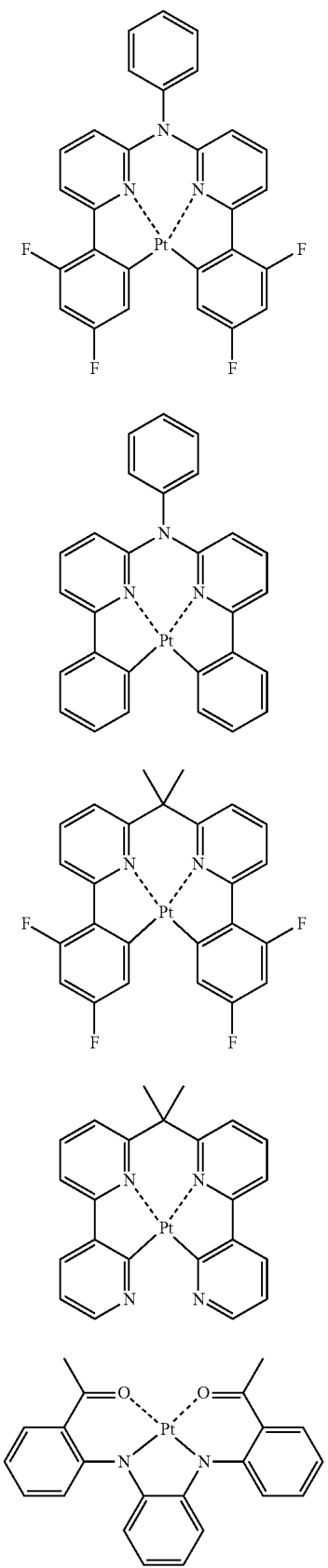
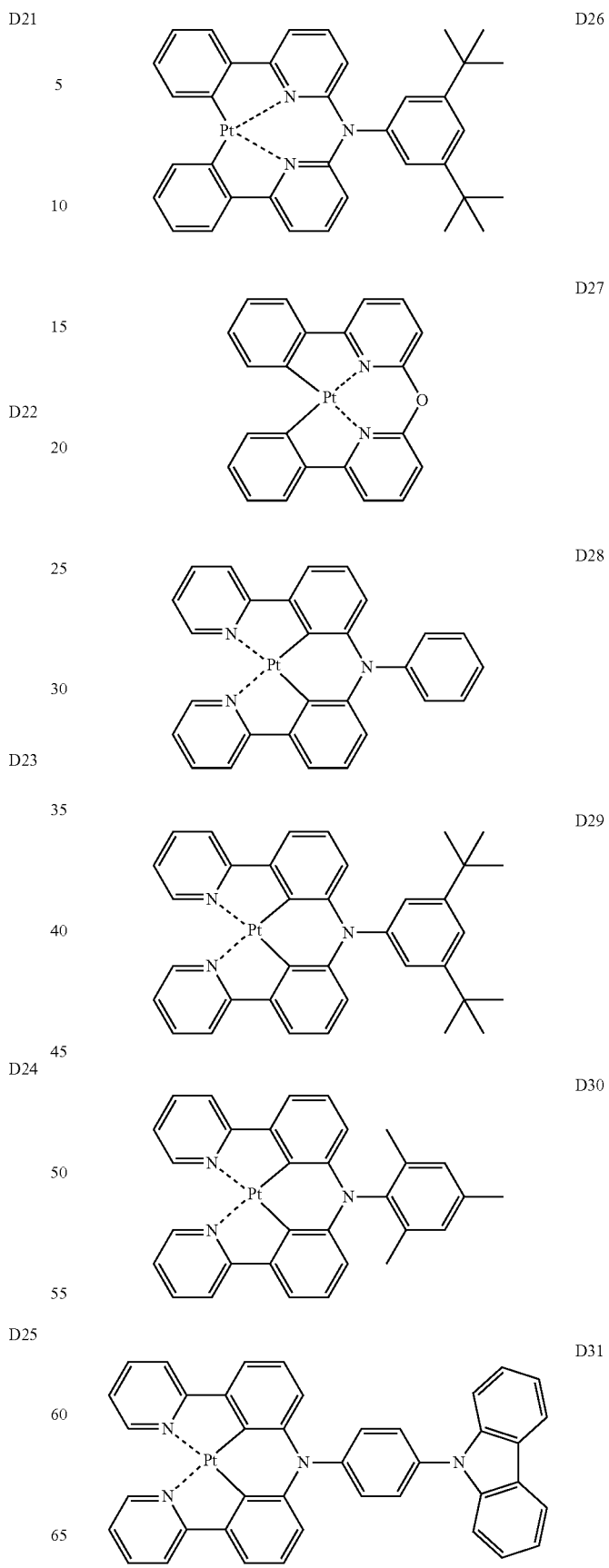

D32 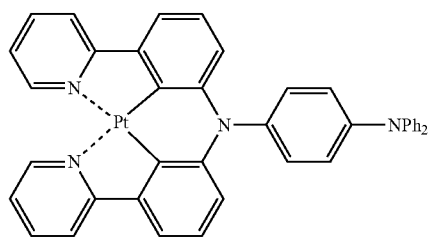
D33 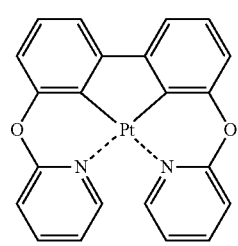
D34 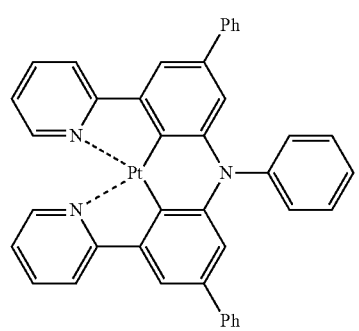
D35 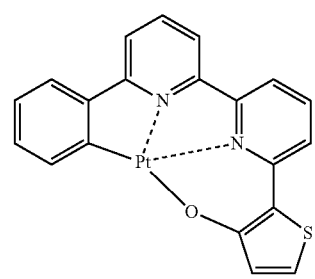
D36 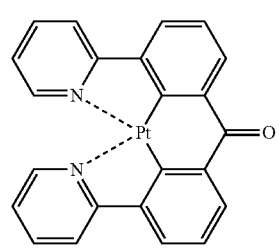
D37 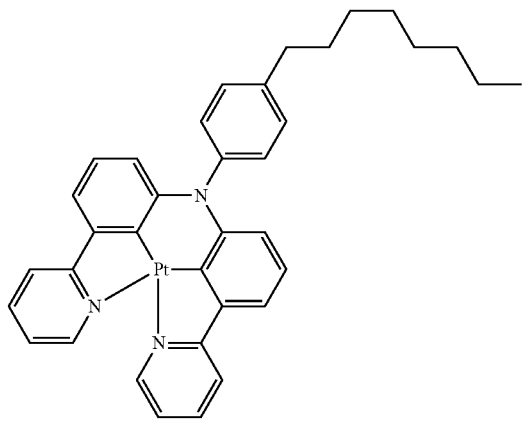
D38 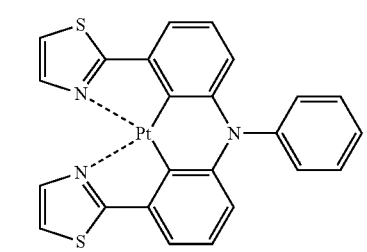
D39 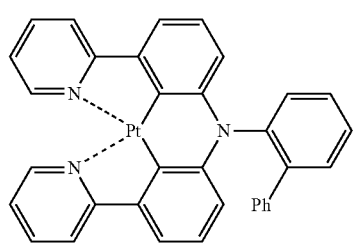
D40 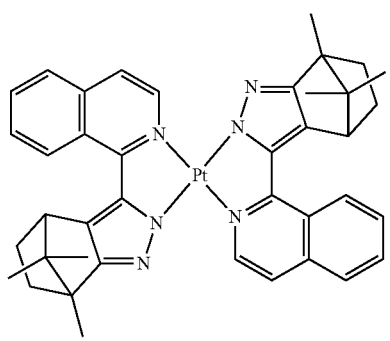
D41 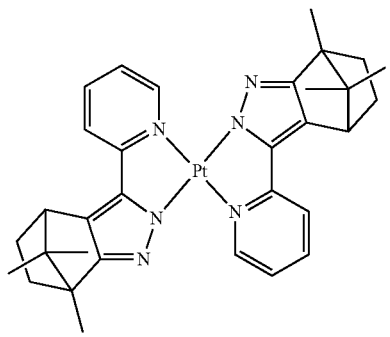

D42
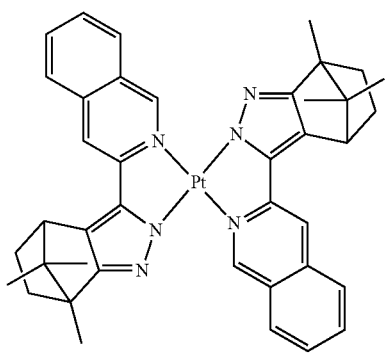
D43
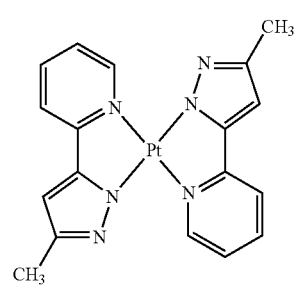
D44
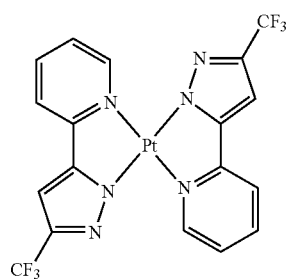
D45
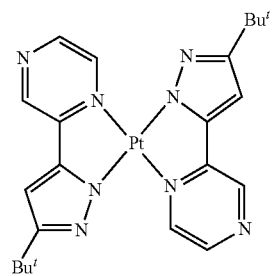
D46
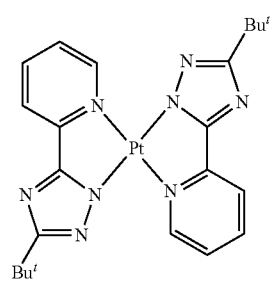
D47
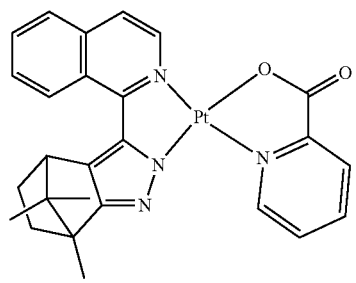
D48
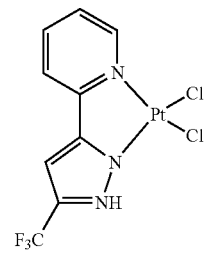
D49
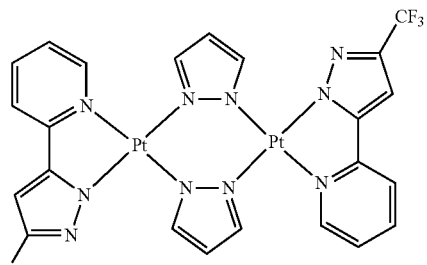
D50
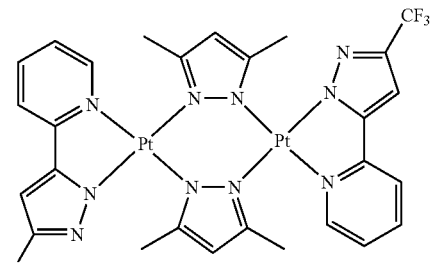
Non-limiting examples of the dopant that may be used in the EML may include Os complexes represented by the following formulae.
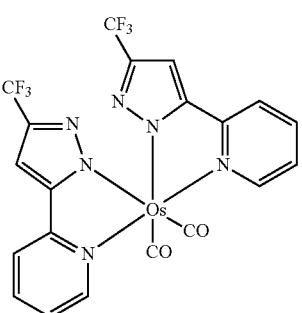
Os(fppz)$_2$(CO)$_2$

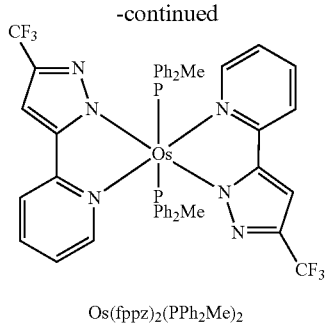

Os(fppz)₂(PPh₂Me)₂

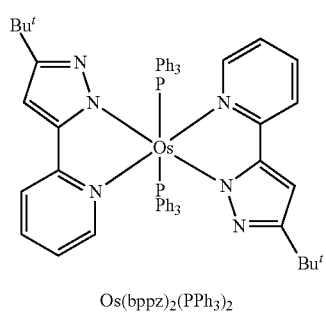

Os(bppz)₂(PPh₃)₂

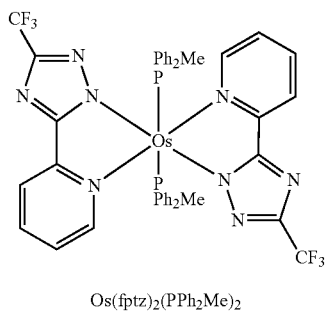

Os(fptz)₂(PPh₂Me)₂

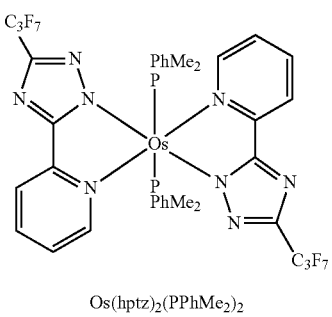

Os(hptz)₂(PPhMe₂)₂

When the EML includes both a host and a dopant, the amount of the dopant may be from about 0.01 to about 15 parts by weight based on 100 parts by weight of the host. However, the amount of the dopant is not limited to this range.

The thickness of the EML may be from about 100 Å to about 1,000 Å, and in some embodiments, from about 200 Å to about 600 Å. When the thickness of the EML is within these ranges, the EML may have good light emitting ability without a substantial increase in driving voltage.

Then, an ETL may be formed on the EML by vacuum deposition, spin coating, casting, or the like. When the ETL is formed using vacuum deposition or spin coating, the deposition and coating conditions may be similar to those for the formation of the HIL, though the deposition and coating conditions may vary according to a compound that is used to form the ETL. A material for forming the ETL may include the compound represented by Formula 1 above, or a suitable material that can stably transport electrons injected from an electron injecting electrode (cathode). Non-limiting examples of materials for forming the ETL may include a quinoline derivative, such as tris(8-quinolinorate)aluminum (Alq3), TAZ, BAlq, beryllium bis(benzoquinolin-10-olate (Bebq₂), 9,10-di(naphthalene-2-yl)anthracene (ADN), Compound 201, and Compound 202, but are not limited thereto.

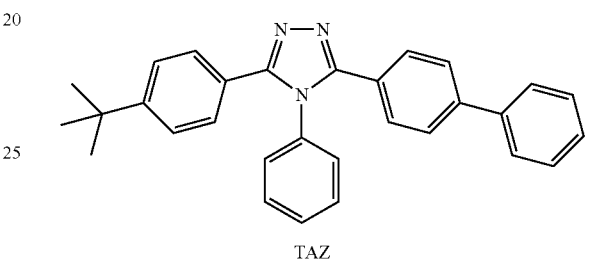

TAZ

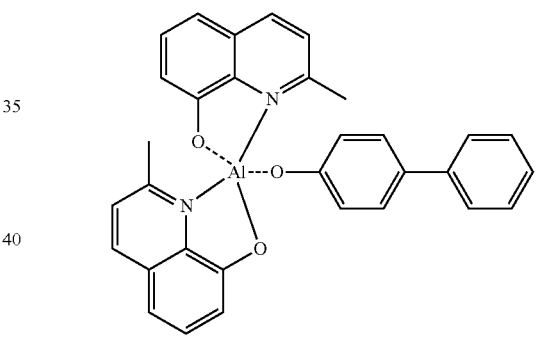

BAlq

<Compound 201>

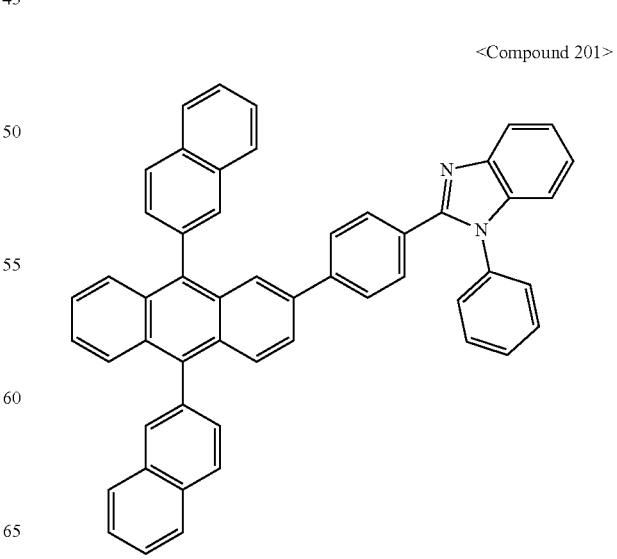

-continued

<Compound 202>

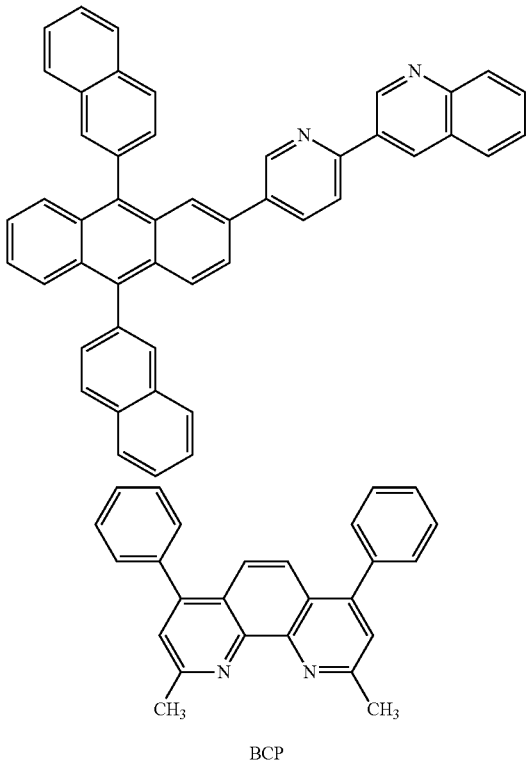
BCP

The thickness of the ETL may be from about 100 Å to about 1,000 Å, and in some embodiments, from about 150 Å to about 500 Å. When the thickness of the ETL is within these ranges, the ETL may have satisfactory electron transporting ability without a substantial increase in driving voltage.

In some embodiments the ETL may further include a metal-containing material, in addition to a suitable electron-transporting organic compound.

The metal-containing material may include a lithium (Li) complex. Non-limiting examples of the Li complex may include lithium quinolate (LiQ) and Compound 203 below:

<Compound 203>

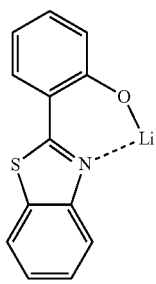

Then, an ETL, which facilitates injection of electrons from the cathode, may be formed on the ETL. A suitable electron-injecting material may be used to form the EIL.

Non-limiting examples of materials for forming the EIL may include LiF, NaCl, CsF, $Li_2O$, and BaO. The deposition and coating conditions for forming the EIL may be similar to those for the formation of the HIL, though the deposition and coating conditions may vary according to the material that is used to form the EIL.

The thickness of the EIL may be from about 1 Å to about 100 Å, and in some embodiments, from about 3 Å to about 90 Å. When the thickness of the EIL is within these ranges, the EIL may have satisfactory electron injection ability without a substantial increase in driving voltage.

Finally, the second electrode is disposed on the organic layer. The second electrode may be a cathode that is an electron injection electrode. A material for forming the second electrode may include a metal, an alloy, an electro-conductive compound, which have a low work function, or a mixture thereof. In this regard, the second electrode may be formed of lithium (Li), magnesium (Mg), aluminum (Al), aluminum (Al)-lithium (Li), calcium (Ca), magnesium (Mg)-indium (In), magnesium (Mg)-silver (Ag), or the like, and may be formed as a thin film type transmission electrode. In some embodiments, to manufacture a top-emission light-emitting device, the transmission electrode may be formed of indium tin oxide (ITO) or indium zinc oxide (IZO).

Although the organic light-emitting device of FIG. 1 is described above, the embodiments are not limited thereto.

When a phosphorescent dopant is used in the EML, a HBL may be formed between the HTL and the EML or between the H-functional layer and the EML by using vacuum deposition, spin coating, casting, Langmuir-Blodgett (LB) deposition, or the like, in order to prevent diffusion of triplet excitons or holes into the ETL. When the HBL is formed using vacuum deposition or spin coating, the conditions for deposition and coating may be similar to those for the formation of the HIL, although the conditions for deposition and coating may vary according to the material that is used to form the HBL. A suitable hole-blocking material may be used. Non-limiting examples of hole-blocking materials may include oxadiazole derivatives, triazole derivatives, and phenanthroline derivatives. For example, bathocuproine (BCP) represented by the following formula may be used as a material for forming the HBL.

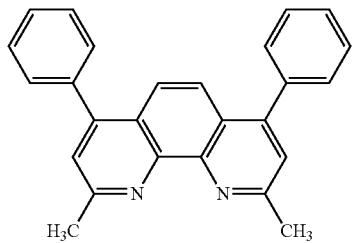
BCP

The thickness of the HBL may be from about 20 Å to about 1,000 Å, and in some embodiments, from about 30 Å to about 300 Å. When the thickness of the HBL is within these ranges, the HBL may have improved hole blocking ability without a substantial increase in driving voltage.

According to embodiments, the organic light-emitting device may be included in various types of flat panel display devices, such as in a passive matrix organic light-emitting display device or in an active matrix organic light-emitting display device. For example, when the organic light-emitting device is included in an active matrix organic light-emitting display device including a thin-film transistor, the first electrode on the substrate may function as a pixel electrode, electrically connected to a source electrode or a drain electrode of the thin-film transistor. Moreover, the organic light-emitting device may also be included in flat panel display devices having double-sided screens.

In some embodiments the organic layer of the organic light-emitting device may be formed of the compound represented by Formula 1 by using a deposition method or may be formed using a wet method of coating a solution of the compound represented by Formula 1.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

Synthesis Example 1

Synthesis of Compound 3

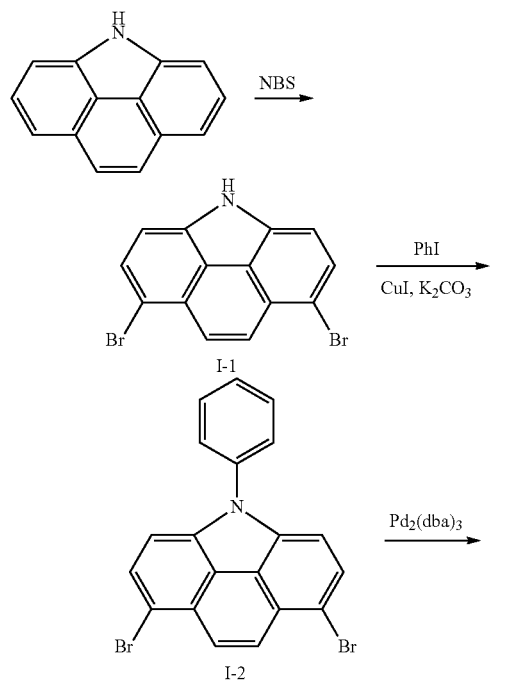

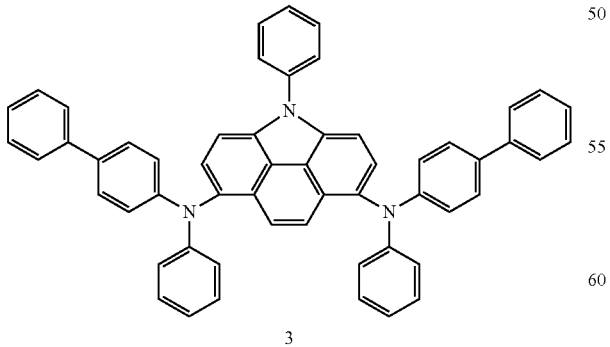

Synthesis of Intermediate I-1

1.91 g (10.0 mmol) 6H-benzo[def]carbazole was completely dissolved in 60 mL of carbon tetrachloride (CCl$_4$) 60 mL, followed by an addition of 3.56 g (20.0 mmol) of N-bromosuccinimide and stirring at about 80° C. for about 30 minutes. The reaction solution was cooled to room temperature, and stirred for about 30 minutes to precipitate crystals. The crystals were collected using a filter under reduced pressure, and then washed with methanol to obtain 1.71 g of Intermediate I-1 as white crystals (Yield 49%). This compound was identified using liquid chromatography-mass spectroscopy. $C_{14}H_7Br_2N$: M$^+$ 346.9

Synthesis of Intermediate I-2

10.0 g (28.7 mmol) of Intermediate I-1, 7.0 g (34.4 mmol) of iodobenzene, 0.5 g (2.87 mmol) of 1,10-phenanthroline, 1.1 g (5.74 mmol) of CuI, and 11.9 g (86.1 mmol) of K$_2$CO$_3$ were dissolved in 100 mL of dimethylformamide (DMF), and then stirred at about 80° C. for about 24 hours. The reaction solution was cooled to room temperature, and then extracted with 100 mL of water. The organic phase was collected and was dried using magnesium sulfate to evaporate the solvent. The residue was separated and purified using silica gel column chromatography to obtain 9.51 g of Intermediate I-2 (Yield 78%). This compound was identified using LC-MS. $C_{20}H_{11}Br_2N$: M$^+$ 422.9

Synthesis of Compound 3

4.2 g (10.0 mmol) of Intermediate I-2, 5.4 g (22.0 mmol) of 4-biphenyl-phenyl amine, 0.73 g (0.8 mmol) of Pd$_2$(dba)$_3$, 0.16 g (0.8 mmol) of PtBu$_3$, and 2.8 g (30.0 mmol) of KOtBu were dissolved in 60 mL of toluene, and then stirred at about 85° C. for about 4 hours. The reaction solution was cooled to room temperature, and then extracted three times with 50 mL of water and 50 mL of diethyl ether. The organic phase was collected and was dried using magnesium sulfate to evaporate the solvent. The residue was separated and purified using silica gel column chromatography to obtain 6.2 g of Compound 3 (Yield 82%). This compound was identified using mass spectroscopy/fast atom bombardment (MS/FAB) and 1H nuclear magnetic resonance (1H NMR). $C_{56}H_{39}N_3$ cal. 753.31, found 754.40.

$^1$H NMR (CDCl$_3$, 400 MHz) ☐ 7.64-7.61 (m, 4H), 7.55-7.49 (m, 8H), 7.44-7.38 (m, 7H), 7.33 (s, 1H), 7.31 (s, 1H), 7.06-7.01 (m, 4H), 6.72 (s, 1H), 6.69 (s, 1H), 6.65-6.61 (m, 2H), 6.53 (s, 2H), 6.46-6.43 (m, 4H), 6.20-6.16 (m, 4H)

Synthesis Example 2

Synthesis of Compound 37

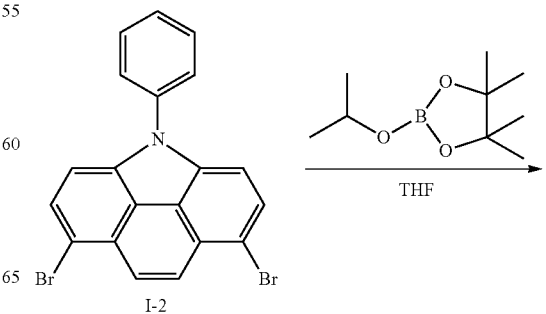

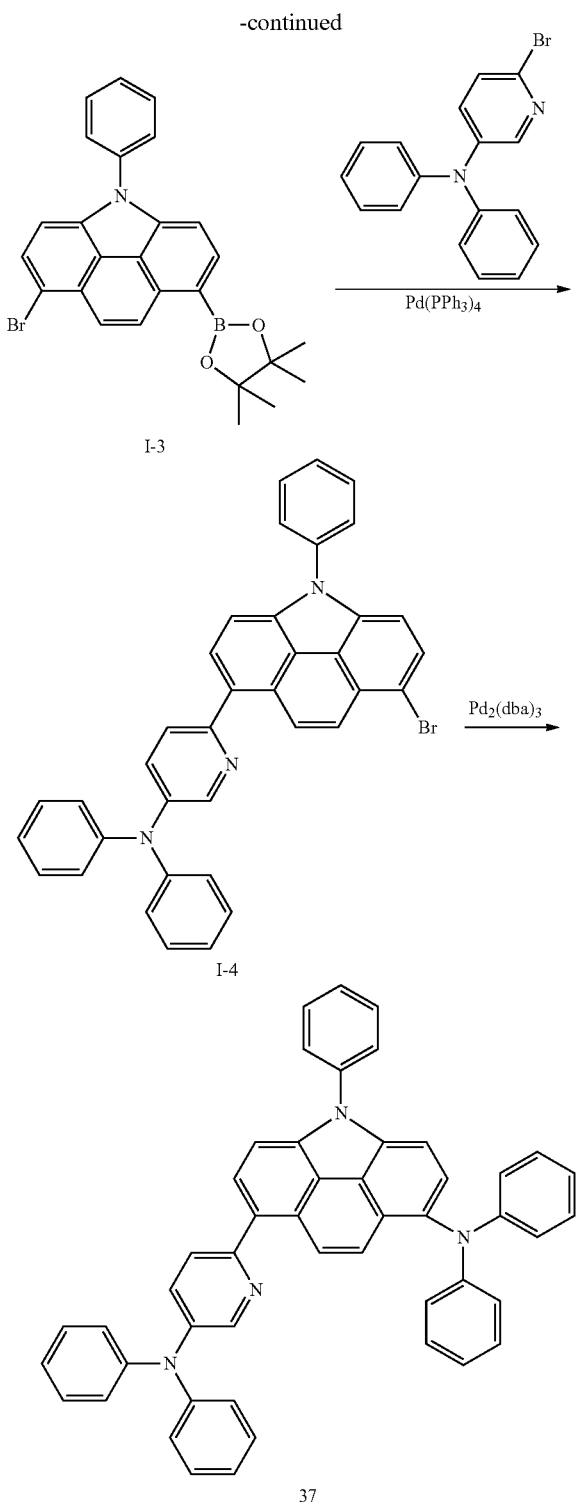

I-3

I-4

37

Synthesis of Intermediate I-3

10.0 g (23.6 mmol) of Intermediate I-2 was dissolved in 100 mL of THF, and then 10 mL (25.0 mmol) of n-BuLi (2.5M in Hexane) was slowly dropwise added thereto at about −78° C. to obtain a mixture, which was then stirred for about 1 hour at the same temperature. Afterward, 9.3 mL (50.0 mmol) 2-isoproxy-4,4,5,5,-tetramethyl-1,3,2-dioxaborolane was slowly dropwise added to the reaction solution, which was then stirred at about −78° C. for about 1 hour, and further at room temperature for 24 hours. After completion of the reaction, 50 mL of a 10% HCl aqueous solution, and 50 mL of $H_2O$ were added thereto, and then extracted three times with 80 mL of diethyl ether. The organic phase was collected and was dried using magnesium sulfate to evaporate the solvent. The residue was separated and purified using silica gel column chromatography to obtain 8.1 g of Intermediate I-3 (Yield 75%). This compound was identified using LC-MS. $C_{26}H_{23}BBrNO_2$: M+ 471.1

Synthesis of Intermediate I-4

4.72 g (10.0 mmol) of Intermediate I-3, 4.2 g (13.0 mmol) of 6-bromo-3-pyridine-diphenylamine, 0.58 g (0.5 mmol) of $Pd(PPh_3)_4$, and 2.1 g (15.0 mmol) of $K_2CO_3$ were dissolved in 40 mL of a mixed solvent of $THF/H_2O$ (2:1 by volume), and then stirred at about 80° C. for about 5 hours. After the reaction solution was cooled to room temperature, 40 mL of water was added to the reaction solution, which was then extracted three times with 50 mL of diethyl ether. The organic phase was collected and was dried using magnesium sulfate to evaporate the solvent. The residue was separated and purified using silica gel column chromatography to obtain 4.6 g of Intermediate I-4 (Yield 78%). This compound was identified using LC-MS. $C_{37}H_{24}BrN_3$: $M^+$ 589.1

Synthesis of Compound 37

2.9 g (5.0 mmol) of Intermediate I-4, 1.0 g (6.0 mmol) of N,N-diphenylamine, 0.09 g (0.1 mmol) of $Pd_2(dba)_3$, 0.01 g (0.1 mmol) of $PtBu_3$, and 1.0 g (10.0 mmol) of KOtBu were dissolved in 20 mL of toluene, and then stirred at about 85° C. for about 4 hours. The reaction was cooled to room temperature, and then extracted three times with 20 mL of water and 20 mL of diethyl ether. The organic phase was collected and was dried using magnesium sulfate to evaporate the solvent. The residue was separated and purified using silica gel column chromatography to obtain 2.7 g of Compound 37 (Yield 81%). This compound was identified using MS/FAS and 1H NMR. $C_{49}H_{34}N_4$ cal. 678.28, found 679.42.

$^1H$ NMR ($CDCl_3$, 400 MHz) ☐ 8.23-8.21 (m, 1H), 7.77 (s, 4H), 7.67-7.65 (ss, 1H), 7.57-7.51 (m, 6H), 7.44-7.41 (m, 2H), 7.34-7.32 (ss, 1H), 7.25-7.20 (m, 3H), 7.14-7.12 (ss, 1H), 7.05-7.01 (m, 4H), 6.95-6.86 (m, 2H), 6.79-6.76 (m, 2H), 6.68-6.59 (m, 6H), 6.51-6.49 (ss, 1H), 6.14-6.11 (m, 4H)

Synthesis Example 3

Synthesis of Compound 49

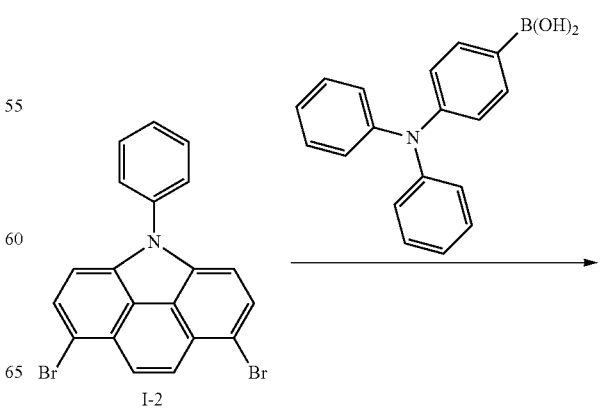

I-2

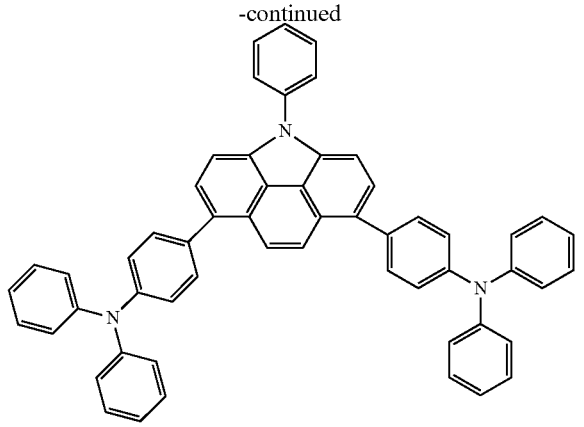

49

4.3 g (5.0 mmol) of Intermediate I-2, 3.2 g (11.0 mmol) of 4-(diphenylamino)phenylboronic acid, 0.58 g (0.5 mmol) of Pd(PPh$_3$)$_4$, and 2.1 g (15.0 mmol) of K$_2$CO$_3$ were dissolved in 10 mL of a mixed solvent of THF/H$_2$O (2:1 by volume), and then stirred at about 80° C. for about 5 hours. The reaction solution was cooled to room temperature, and then extracted three times with 30 mL or water and 30 mL of diethyl ether. The organic phase was collected and was dried using magnesium sulfate to evaporate the solvent. The residue was separated and purified using silica gel column chromatography to obtain 2.7 g of Compound 49 (Yield 69%). This compound was identified using MS/FAS and $^1$H NMR. C$_{56}$H$_{39}$N$_3$ cal. 753.31, found 754.33.

$^1$H NMR (CDCl$_3$, 400 MHz) ⎕ 7.80 (s, 1H), 7.78 (s, 1H), 7.61-7.49 (m, 8H), 7.40-7.38 (m, 1H), 7.34 (s, 1H), 7.31 (s, 1H), 7.08-7.03 (m, 10H), 6.97-6.93 (m, 4H), 6.67-6.63 (m, 4H), 6.67-6.62 (m, 4H), 6.16-6.13 (m, 8H)

Additional compounds were synthesized using appropriate intermediate materials according to the synthetic pathways and the methods described as above, and were identified using 1H NMR and MS/FAB. The results are shown in Table 1, below.

TABLE 1

| Com-pound | $^1$H NMR (CDCl$_3$, 400 MHz) | MS/FAB found | calc. |
|---|---|---|---|
| 2 | 8.04-8.01 (dd, 2H), 7.87-7.85 (dd, 2H), 7.79 (s, 2H), 7.55-7.36 (m, 11H), 7.27 (s, 1H), 7.25 (s, 1H), 7.19-7.15 (t, 2H), 7.05-7.01 (m, 4H), 6.77-6.75 (d, 2H), 6.69-6.67 (dd, 2H), 6.63-6.60 (m, 2H), 6.05-6.01 (m, 4H) | 702.33 | 701.28 |
| 3 | 7.64-7.61 (m, 4H), 7.55-7.49 (m, 8H), 7.44-7.38 (m, 7H), 7.33 (s, 1H), 7.31 (s, 1H), 7.06-7.01 (m, 4H), 6.72 (s, 1H), 6.69 (s, 1H), 6.65-6.61 (m, 2H), 6.53 (s, 2H), 6.46-6.43 (m, 4H), 6.20-6.16 (m, 4H) | 754.40 | 753.31 |
| 4 | 7.78-7.76 (m, 2H), 7.75-7.49 (m, 6H), 7.43-7.31 (m, 3H), 7.27 (s, .1H), 7.24 (s, 1H). 7.14-7.11 (m, 4H), 7.07-7.04 (m, 4H), 6.66-6.61 (m, 4H), 6.54 (s, 1H), 6.53-6.52 (d, 3H), 6.41-6.40 (d, 2H), 6.18-6.15 (m, 4H), 1.61 (s, 12H) | 834.51 | 833.38 |
| 5 | 8.22-8.20 (m, 2H), 7.55-7.49 (m, 12H), 7.44 (s, 1H), 7.42 (s, 1H), 7.37-7.23 (m, 13H), 7.07-7.02 (m, 4H), 6.82 (dd, 2H), 6.76 (s, 1H), 6.74 (s, 1H), 6.65-6.61 (m, 2H), 6.52 (s, 2H), 6.25-6.21 (m, 4H) | 932.44 | 931.37 |
| 7 | 7.84-7.82 (m, 2H), 7.74-7.71 (m, 4H), 7.55-7.49 (m, 7H), 7.44 (s, 1H), 7.42 (d, 1H), 7.40-7.35 (m, 2H), 7.27 (s, 1H), 7.24 (s, 2H), 7.07-7.02 (m, 4H), 6.87-6.84 (sd, 2H), 6.76 (s, 1H), 6.74 (s, 1H), 6.65-6.61 (m, 2H), 6.52 (s, 2H), 6.26-6.22 (m, 4H) | 782.33 | 781.27 |
| 8 | 7.78-7.76 (m, 2H), 7.63-7.61 (m, 4H), 7.55-7.49 (m, 10H), 7.45-7.30 (m, 9H), 7.27 (s, 1H), 7.24 (s, 1H), 7.14-7.09 (m, 4H), 6.74 (s, 1H), 6.72 (s, 1H), 6.68-6.66 (dd, 2H), 6.52 (s, 2H), 6.48-6.44 (m, 6H), 1.61 (s, 12H) | 986.46 | 985.44 |
| 11 | 8.04-8.01 (m, 2H), 7.87-7.85 (m, 2H), 7.79 (s, 2H), 7.55-7.33 (m, 11H), 7.27 (s, 1H), 7.25 (s, 1H), 7.19-7.15 (t, 2H), 6.77 (s, 1H), 6.75 (s, 1H), 6.69-6.67 (dd, 2H) | 712.37 | 711.35 |
| 15 | 7.82 (s, 2H), 7.72-7.69 (m, 4H), 7.65-7.63 (m, 6H), 7.59-7.49 (m, 14H), 7.44-7.33 (m, 5H), 7.06-7.01 (m, 6H), 6.80 (s, 1H), 6.78 (s, 1H), 6.62-6.58 (m, 2H), 6.11-6.07 (m, 4H) | 942.55 | 941.36 |
| 17 | 7.55-7.48 (m, 4H), 7.41-7.37 (m, 5H), 7.33 (s, 1H), 7.31 (s, 1H), 7.06-7.01 (m, 4H), 6.72 (s, 1H), 6.69 (s, 1H), 6.65-6.61 (m, 2H), 6.53-6.50 (m, 6H), 6.20-6.16 (m, 4H), 0.25-0.23 (s, 18H) | 746.42 | 745.33 |
| 19 | 7.64-7.60 (m, 6H), 7.52-7.46 (m, 8H), 7.43-7.36 (m, 13H), 7.27 (s, 1H), 7.24 (s, 1H), 6.93 (s, 1H), 6.91 (s, 1H), 6.74-6.70 (m, 4H), 6.52-6.49 (m, 6H) | 880.35 | 879.34 |
| 21 | 7.95-7.94 (m, 1H), 7.70-7.68 (ss, 1H), 7.47-7.43 (m, 4H), 7.40 (s, 1H), 7.34 (s, 1H), 7.32 (m, 3H), 7.28-7.26 (dd, 2H), 7.23-7.18 (m, 4H), 7.16-7.02 (m, 12H), 6.90-6.80 (m, 1H), 6.65-6.61 (m, 2H), 6.52-6.51 (m, 3H), 6.27-6.24 (m, 4H), 6.21-6.18 (m, 2H) | 892.40 | 891.34 |
| 23 | 7.78-7.76 (m, 1H), 7.64-7.60 (m, 4H), 7.52-7.49 (m, 7H), 7.43-7.33 (m, 9H), 7.27-7.21 (q, 2H), 7.11-7.07 (m, 2H), 7.05-7.02 (m, 2H), 6.93-6.91 (ss, 1H), 6.74-6.70 (m, 2H), 6.06-6.01 (m, 2H), 6.54-6.49 (m, 5H), 6.41-6.40 (dd, 1H), 6.18-6.15 (m, 2H), 1.61 (s, 6H) | 895.33 | 894.37 |
| 26 | 8.64-8.63 (m, 1H), 8.50-8.49 (m, 1H), 7.85-7.83 (m, 1H), 7.64-7.62 (m, 4H), 7.52-7.38 (m, 13H), 7.05-7.02 (m, 4H), 6.97 (s, 1H), 6.94 (s, 1H), 6.65-6.61 (m, 2H), 6.53 (s, 2H), 6.46-6.43 (m, 4H), 6.20-6.17 (m, 4H) | 755.56. | 754.31 |
| 28 | 8.78-8.75 (m, 4H), 7.76 (s, 1H), 7.74 (s, 1H), 7.67-7.65 (m, 4H), 7.46 (s, 1H), 7.44-7.38 (m, 3H), 7.06-7.01 (m, 8H), 6.89 (s, 2H), 6.65-6.61 (m, 4H), 6.14-6.11 (m, 8H) | 757.43 | 756.30 |
| 31 | 8.17-8.15 (m, 1H), 7.87-7.85 (m, 1H), 7.80-7.78 (ss, 1H), 7.59-7.38 (m, 10H), 7.34-7.32 (ss, 1H), 7.25-7.21 (t, 1H), 7.14-7.12 (ss, 1H), 7.05-7.03 (m, 6H), 6.97-6.94 (m, 2H), 6.89-6.86 (ss, 1H), 6.79-6.77 (ss, 1H), 6.74-6.72 (m, 1H), 6.65-6.61 (m, 3H), 6.54-6.48 (ss, 1H), 6.13-6.11 (m, 4H), 6.07-6.05 (m, 2H) | 728.35 | 727.30 |
| 35 | 8.12-8.10 (m, 2H), 7.94-7.92 (ss, 1H), 7.79-7.77 (ss, 1H), 7.64-7.61 (m, 2H), 7.55-7.49 (m, 6H), 7.43-7.36 (m, 8H), 7.31-7.25 (m, 3H), 7.15-7.13 (ss, 1H), 7.06-7.01 (m, 2H), 6.95-6.93 (ss, 1H), 6.72-6.69 (ss, 1H), 6.62-6.61 (m, 1H), 6.46-6.43 (m, 2H), 6.20-6.16 (m, 2H) | 676.45 | 675.27 |
| 37 | 8.43 (s, 1H), 8.28-8.26 (ss, 1H), 7.73-7.71 (ss, 1H), 7.68-7.66 (ss, 1H), 7.55-7.50 (m, 4H), 7.41-7.33 (m, 2H), 7.14-7.03 (m, 9H), 6.87-6.85 (ss, 1H), 6.83-6.81 (dd, 1H), 6.66-6.01 (m, 4H), 6.51-6.49 (ss, 1H), 6.33-6.31 (m, 4H), 6.13-6.11 (m, 4H) | 679.42 | 678.28 |
| 39 | 8.23-8.21 8.23-8.21 (m, 1H), 7.77 (s, 4H), 7.67-7.65 (ss, 1H), 7.57-7.51 (m, 6H), 7.44-7.41 (m, 2H), 7.34-7.32 (m, 2H), 7.25-7.20 (m, 3H), 7.14-7.12 (ss, 1H), 7.05-7.01 (m, 4H), 6.95-6.86 (m, 2H), 6.79-6.76 (m, 2H), 6.68-6.59 (m, 6H), 6.51-6.49 (ss, 1H), 6.14-6.11 (m, 4H) | 755.45 | 754.31 |
| 44 | 8.50 (d, 1H), 7392-7.90 (t, 2H), 7.61 (d, 1H), 7.55-7.49 (m, 5H), 7.43-7.36 (m, 1H), 7.29-7.27 (ss, 1H), 7.14-7.12 (ss, 1H), 7.08-6.98 (m, 9H), 6.90-6.87 (dd, 1H), 6.73-6.71 (ss, 1H), 6.66-6.61 (m, 4H), 6.51-6.49 (ss, 1H), 6.24-6.22 (m, 4H), 6.14-6.11 (m, 4H) | 768.44 | 767.29 |

TABLE 1-continued

| Compound | ¹H NMR (CDCl₃, 400 MHz) | MS/FAB found | MS/FAB calc. |
|---|---|---|---|
| 47 | 8.12-8.10 (m, 2H), 7.80-7.77 (dd, 2H), 7.61-7.49 (m, 7H), 7.44-7.35 (m, 6H), 7.31-7.25 (m, 3H), 7.13-7.11 (ss, 1H), 7.08-7.03 (m, 4H), 6.97-6.93 (m, 2H), 6.66-6.63 (m, 2H), 6.16-6.13 (m, 4H) | 676.43 | 675.27 |
| 49 | 7.80 (s, 1H), 7.78 (s, 1H), 7.61-7.49 (m, 8H), 7.40-7.38 (m, 1H), 7.34 (s, 1H), 7.31 (s, 1H), 7.08-7.03 (m, 10H), 6.97-6.93 (m, 4H), 6.67-6.63 (m, 4H), 6.67-6.62 (m, 4H), 6.16-6.13 (m, 8H) | 754.33 | 753.31 |
| 50 | 7.81 (s, 1H), 7.78-7.76 (m, 3H), 7.61-7.49 (m, 10H), 7.40-7.30 (m, 5H), 7.14-7.04 (m, 10H), 6.69-6.68 (ss, 1H), 6.66-6.63 (m, 3H), 6.42-6.38 (m, 6H), 6.24-6.20 (m, 4H), 1.61 (s, 12H) | 986.45 | 985.44 |
| 53 | 7.77 (s, 8H), 7.67-7.65 (ss, 2H), 7.55-7.48 (m, 4H), 7.46-7.43 (m, 5H), 7.34-7.31 (ss, 1H), 7.08-7.03 (m, 11H), 6.86-6.82 (m, 4H), 6.66-6.62 (m, 4H), 6.16-6.13 (m, 8H) | 906.52 | 905.38 |
| 54 | 7.81-7.78 (m, 2H), 7.63-7.58 (m, 6H), 7.53-7.47 (m, 4H), 7.39-7.31 (m, 3H), 7.32-7.30 (ss, 2H), 7.08-7.03 (m, 10H), 6.97-6.93 (m, 4H), 6.67-6.63 (m, 4H), 6.16-6.13 (m, 8H) | 782.69 | 781.35 |
| 55 | 7.80 s, 1H), (s, 1H), 7.61-7.48 (m, 8H), 7.40-7.36 (m, 5H), 7.34 (s, 1H), 7.31 (s, 1H), 7.09 (s, 2H), 7.06-7.03 (m, 4H), 6.96-6.93 (m, 4H), 6.76-6.72 (m, 4H), 6.66-6.62 (m, 2H), 6.23-6.21 (m, 4H) | 804.33 | 803.30 |
| 57 | 7.82 s, 1H), (s, 1H), 7.61-7.58 (m, 4H), 7.53-7.48 (m, 4H), 7.40-7.38 (m, 1H), 7.34 (s, 1H), 7.31 (s, 1H), 7.23-7.19 (t, 2H), 7.08-7.04 (m, 8H), 6.97-6.93 (m, 4H), 6.67-6.62 (m, 2H), 6.37 (m, 2H), 6.20-6.17 (m, 4H), 6.12-6.10 (m, 2H), 2.30 (m, 6H) | 782.88 | 781.35 |

Example 1

To manufacture an anode, a Corning 15 Ω/cm² (1200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone. The resulting glass substrate was loaded into a vacuum deposition device.

Then, Compound 3 was vacuum-deposited on the glass substrate to form a HIL having a thickness of about 600 Å. Then, 4,4'-bis[N-(1-naphthyl)-N-phenylamino]biphenyl (NPB), which is a hole transporting compound, was vacuum-deposited on the HIL to form a HTL having a thickness of about 300 Å.

A blue fluorescent host 9,10-di-naphthalene-2-yl-anthracene (DNA) and a blue fluorescent dopant, 4'-bis[2-(4-(N,N-diphenylamino)phenyl)vinyl]biphenyl 4,4-bis-(4-diphenylvinyl)biphenyl (DPAVBi), were co-deposited on the HTL in a weight ratio of 98:2 to form an EML having a thickness of about 300 Å.

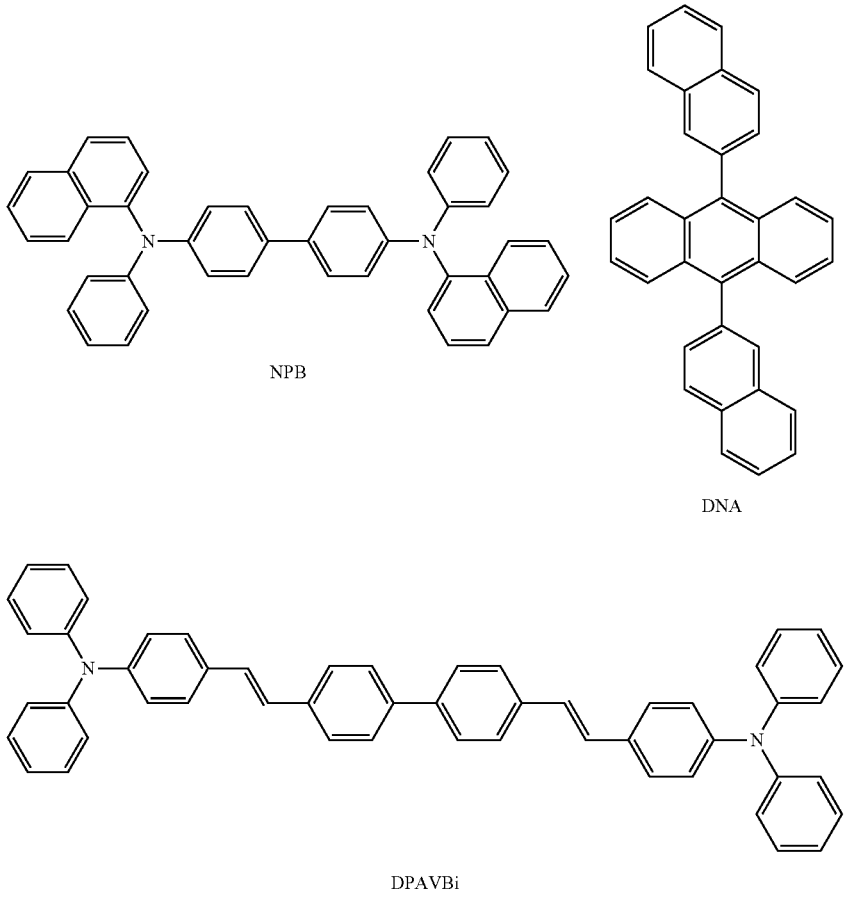

NPB

DNA

DPAVBi

Then, $Alq_3$ was deposited on the EML to form an ETL having a thickness of 300 Å, and then LiF, which is a halogenated alkali metal, was deposited on the ETL to form an EIL having a thickness of 10 Å. Then, Al was vacuum-deposited on the EIL to form a cathode having a thickness of 3,000 Å, thereby forming an LiF/Al electrode and completing the manufacture of an organic light-emitting device.

The organic light-emitting device had a driving voltage of about 5.33 V at a current density of 50 $mA/cm^2$, a luminosity of 2,770 $cd/m^2$, a luminescent efficiency of 5.54 cd/A, and a half life-span (hr @100 $mA/cm^2$) of about 317 hours.

Example 2

An organic light-emitting device was manufactured in the same manner as in Example 1, except that Compound 8 was used, instead of Compound 3, to form the HIL.

The organic light-emitting device had a driving voltage of about 5.21 V at a current density of 50 $mA/cm^2$, a luminosity of 2,830 $cd/m^2$, a luminescent efficiency of 5.66 cd/A, and a half life-span (hr @100 $mA/cm^2$) of about 364 hours.

Example 3

An organic light-emitting device was manufactured in the same manner as in Example 1, except that Compound 21 was used, instead of Compound 3, to form the HIL.

The organic light-emitting device had a driving voltage of about 5.19V at a current density of 50 $mA/cm^2$, a luminosity of 2,660 $cd/m^2$, a luminescent efficiency of 5.32 cd/A, and a half life-span (hr @100 $mA/cm^2$) of about 286 hours.

Example 4

An organic light-emitting device was manufactured in the same manner as in Example 1, except that Compound 37 was used, instead of Compound 3, to form the HIL.

The organic light-emitting device had a driving voltage of about 5.39V at a current density of 50 $mA/cm^2$, a luminosity of 2,690 $cd/m^2$, a luminescent efficiency of 5.38 cd/A, and a half life-span (hr @100 $mA/cm^2$) of about 276 hours.

Example 5

An organic light-emitting device was manufactured in the same manner as in Example 1, except that Compound 39 was used, instead of Compound 3, to form the HIL.

The organic light-emitting device had a driving voltage of about 5.28V at a current density of 50 $mA/cm^2$, a luminosity of 2,635 $cd/m^2$, a luminescent efficiency of 5.27 cd/A, and a half life-span (hr @100 $mA/cm^2$) of about 238 hours.

Example 6

An organic light-emitting device was manufactured in the same manner as in Example 1, except that Compound 47 was used, instead of Compound 3, to form the HIL.

The organic light-emitting device had a driving voltage of about 5.46V at a current density of 50 $mA/cm^2$, a luminosity of 2,680 $cd/m^2$, a luminescent efficiency of 5.36 cd/A, and a half life-span (hr @100 $mA/cm^2$) of about 324 hours.

Example 7

An organic light-emitting device was manufactured in the same manner as in Example 1, except that Compound 49 was used, instead of Compound 3, to form the HIL.

The organic light-emitting device had a driving voltage of about 5.17V at a current density of 50 $mA/cm^2$, a luminosity of 2,810 $cd/m^2$, a luminescent efficiency of 5.62 cd/A, and a half life-span (hr @100 $mA/cm^2$) of about 347 hours.

Example 8

An organic light-emitting device was manufactured in the same manner as in Example 1, except that Compound 53 was used, instead of Compound 3, to form the HIL.

The organic light-emitting device had a driving voltage of about 5.20V at a current density of 50 $mA/cm^2$, a luminosity of 2,795 $cd/m^2$, a luminescent efficiency of 5.59 cd/A, and a half life-span (hr @100 $mA/cm^2$) of about 311 hours.

Comparative Example 1

An organic light-emitting device was manufactured in the same manner as in Example, 1 except that 4,4',4"-tris(N-(2-naphthyl)-N-phenyl-amino)-triphenylamine(2-TNATA) was used, instead of Compound 3, to form the HIL.

The organic light-emitting device had a driving voltage of about 7.35V at a current density of 50 $mA/cm^2$, a luminosity of 2,065 $cd/m^2$, a luminescent efficiency of 4.13 cd/A, and a half life-span (hr @100 $mA/cm^2$) of about 145 hours.

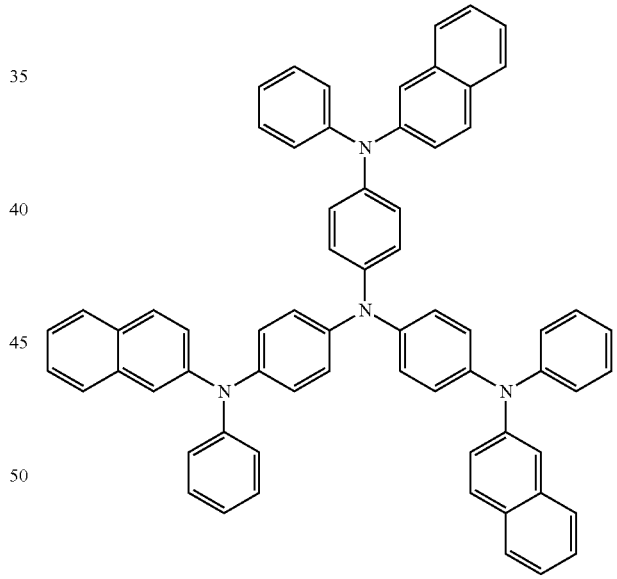

2-TNATA

The organic light-emitting devices manufactured using the compounds represented by Formula 1 according to embodiments as HIL materials had significantly lower driving voltages and improved I-V-L characteristics, as compared to those manufactured using 2-TNATA. In particular, the organic light-emitting devices according to the embodiments had markedly improved lifetimes. The characteristics of the organic light-emitting devices of Examples 1-8 and Comparative Example 1 are shown in Table 2 below.

TABLE 2

|  | HIL material | Driving voltage (V) | Current density (mA/cm$^2$) | Luminance (cd/m$^2$) | Efficiency (cd/A) | Emission color | Half-life span (hr @100 mA/cm$^2$) |
|---|---|---|---|---|---|---|---|
| Example 1 | Compound 3 | 5.33 | 50 | 2,770 | 5.54 | Blue | 317 hr |
| Example 2 | Compound 8 | 5.21 | 50 | 2,830 | 5.66 | Blue | 364 hr |
| Example 3 | Compound 21 | 5.19 | 50 | 2,660 | 5.32 | Blue | 286 hr |
| Example 4 | Compound 37 | 5.39 | 50 | 2,690 | 5.38 | Blue | 276 hr |
| Example 5 | Compound 39 | 5.28 | 50 | 2,635 | 5.27 | Blue | 238 hr |
| Example 6 | Compound 47 | 5.46 | 50 | 2,680 | 5.36 | Blue | 324 hr |
| Example 7 | Compound 49 | 5.17 | 50 | 2,810 | 5.62 | Blue | 347 hr |
| Example 8 | Compound 53 | 5.20 | 50 | 2,795 | 5.59 | Blue | 311 hr |
| Comparative Example 1 | 2-TNATA | 7.35 | 50 | 2,065 | 4.13 | Blue | 145 hr |

The condensed ring compound represented by Formula 1 above exhibits improved emission characteristics and charge transporting capability, and so, may be used as a hole injecting material or a hole transporting material that is suitable for any color fluorescent and phosphorescent devices, such as red, green, blue, and white fluorescent and phosphorescent devices. Therefore, organic light-emitting devices having high efficiency, low driving voltages, high luminance, and long lifetime may be manufactured using the compounds.

The embodiments provide a material having improved electrical stability, high charge-transfer or emission capability, a high glass transition temperature, and capable of preventing crystallization, relative to existing unimolecular materials.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A compound represented by Formula 1 below:

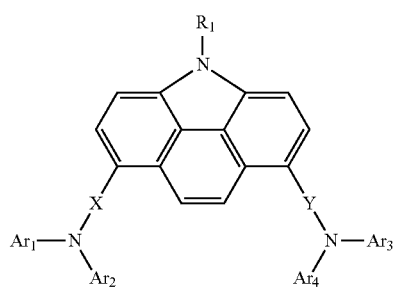

<Formula 1> wherein, in Formula 1, $R_1$ is a substituted or unsubstituted C1-C60 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C3-C60 cycloalkenyl group, a substituted or unsubstituted C5-C60 aryl group, a substituted or unsubstituted C2-C60 heteroaryl group, a substituted or unsubstituted C5-C60 aryloxy group, a substituted or unsubstituted C5-C60 arylthio group; or a substituted or unsubstituted C6-C60 condensed polycyclic group, $Ar_1$ to $Ar_4$ are each independently a substituted or unsubstituted C6-C60 aryl group, a substituted or unsubstituted C2-C60 heteroaryl group, or a substituted or unsubstituted C6-C60 condensed polycyclic group, X and Y are each independently a single bond, a substituted or unsubstituted C6-C60 arylene group, a substituted or unsubstituted C2-C60 heteroarylene group, a substituted or unsubstituted C6-C60 condensed polycyclic group, or a divalent linking group formed by linking at least two of the arylene group, the heteroarylene group, and the condensed polycyclic groups.

2. The compound of claim 1, wherein, in Formula 1:

$Ar_1$, $Ar_2$, or X are each independently linked to one another to form a ring, or $Ar_3$, $Ar_4$, or Y are each independently linked to one another to form a ring.

3. The compound of claim 1, wherein, in Formula 1, $R_1$ is a group represented by one of Formulae 2a-2d, below:

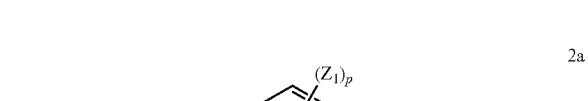

2a

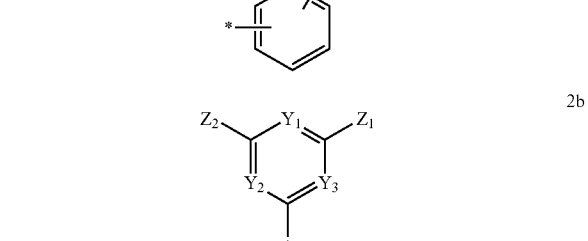

2b

2c

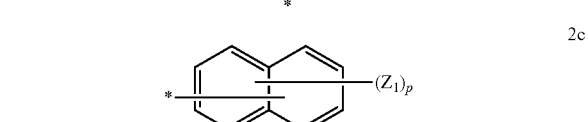

2d

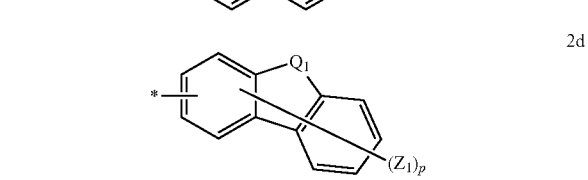

wherein, in Formulae 2a-2d, $Y_1$, $Y_2$, and $Y_3$ are each independently C, or N;

$Q_1$ is a linking group represented by —C($R_{30}$)($R_{31}$)—, or —N($R_{32}$)—;

$Z_1$, $Z_2$, $R_{30}$, $R_{31}$, and $R_{32}$ are each independently a hydrogen atom, a deuterium atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, —Si($R_{40}$)$_3$, a halogen group, a cyano group, a nitro group, a hydroxy group, or a carboxy group;

$R_{40}$ is a substituted or unsubstituted C1-C20 alkyl group, a substituted or unsubstituted C5-C20 aryl group, a substituted or unsubstituted C3-C20 heteroaryl group, or a substituted or unsubstituted C6-C20 condensed polycyclic group;

p is an integer from 1 to 7; and

* indicates a binding site to a nitrogen atom.

4. The compound of claim 1, wherein, in Formula 1, $Ar_1$ to $Ar_4$ are each independently a group represented by one of Formulae 3a to 3d, below:

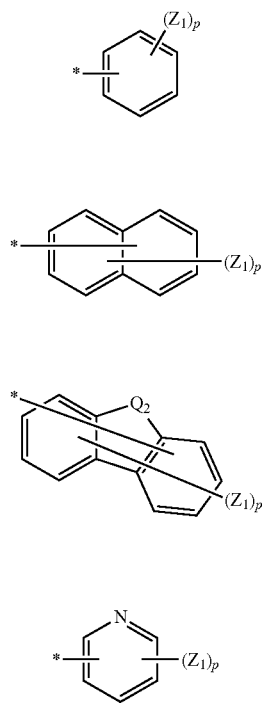

wherein, in Formulae 3a to 3d, $Q_2$ is a linking group represented by —C($R_{30}$)($R_{31}$)—, —N($R_{32}$)—, —S—, or —O—;

$Z_1$, $R_{30}$, $R_{31}$, and $R_{32}$ are each independently, a hydrogen atom, a deuterium atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, —Si($R_{40}$)$_3$, a halogen group, a cyano group, a nitro group, a hydroxy group, or a carboxy group;

$R_{40}$ is a substituted or unsubstituted C1-C20 alkyl group, a substituted or unsubstituted C5-C20 aryl group, a substituted or unsubstituted C3-C20 heteroaryl group, or a substituted or unsubstituted C6-C20 condensed polycyclic group;

p is an integer from 1 to 7; and

* indicates a binding site to a nitrogen atom.

5. The compound of claim 1, wherein, in Formula 1, X and Y are each independently a group represented by one of Formulae 4a to 4f, below:

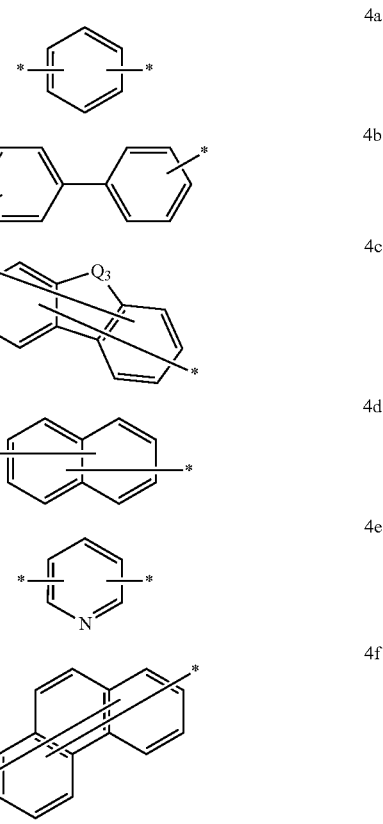

wherein, in Formulae 4a to 4f, $Q_3$ is a linking group represented by —C($R_{30}$)($R_{31}$)—, —N($R_{32}$)—, or —O—;

$R_{30}$, $R_{31}$, and $R_{32}$ are each independently a hydrogen atom, a deuterium atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen group, a cyano group, a nitro group, a hydroxy group, or a carboxy group;

$R_{30}$ and $R_{31}$ are separate or are linked to each other to form a ring; and

* indicates a binding site to a nitrogen atom or a carbon atom.

6. The compound of claim 1, wherein the compound represented by Formula 1 is one of the following compounds:

89 90
3
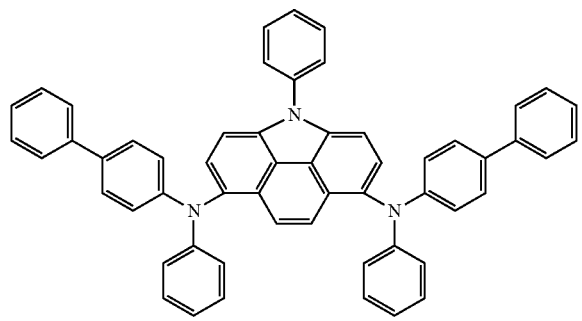
8
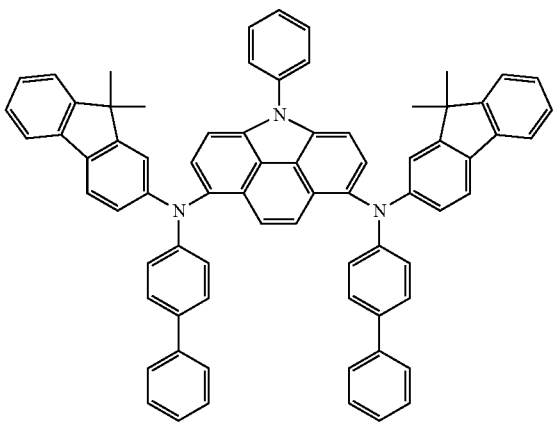
21
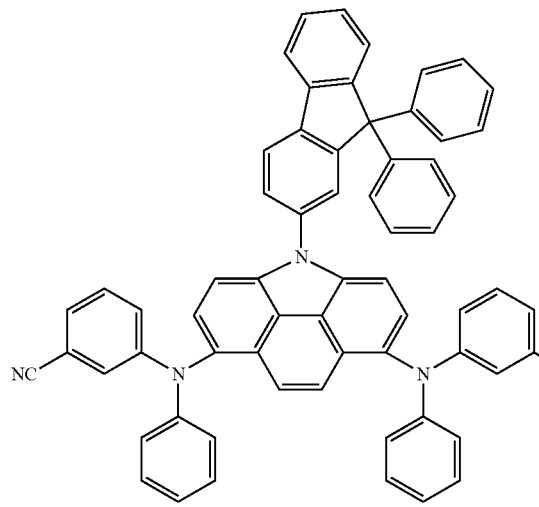
37
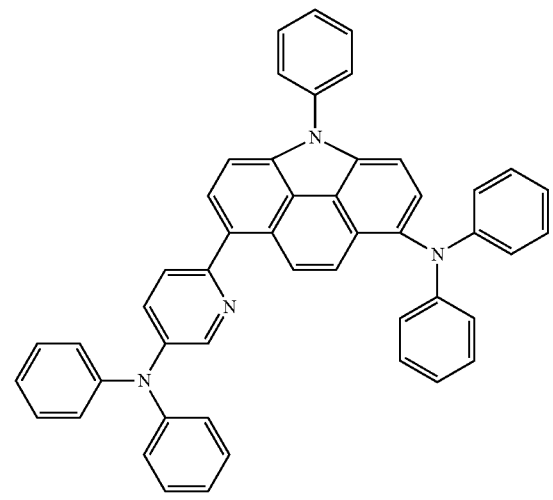
39
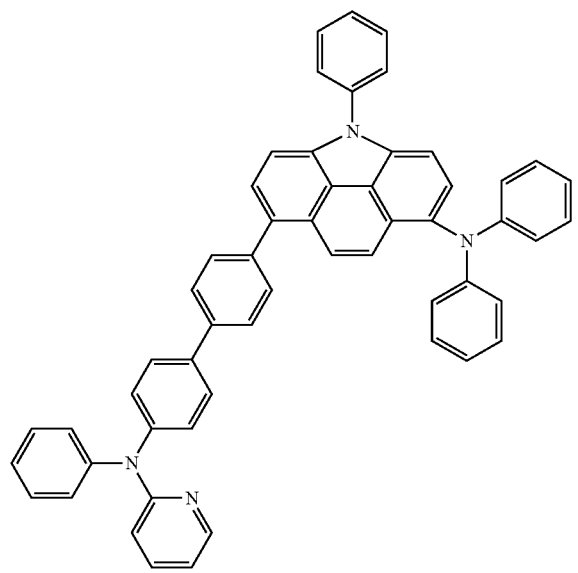
47
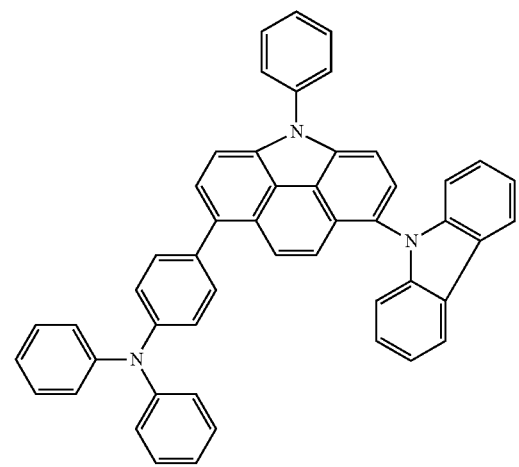

-continued

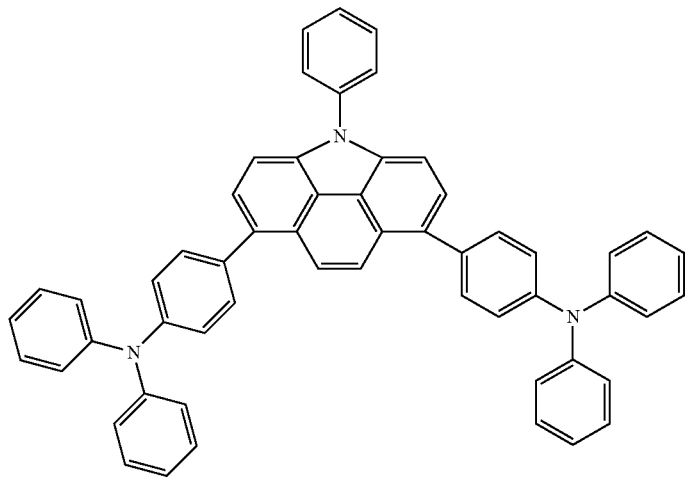
49

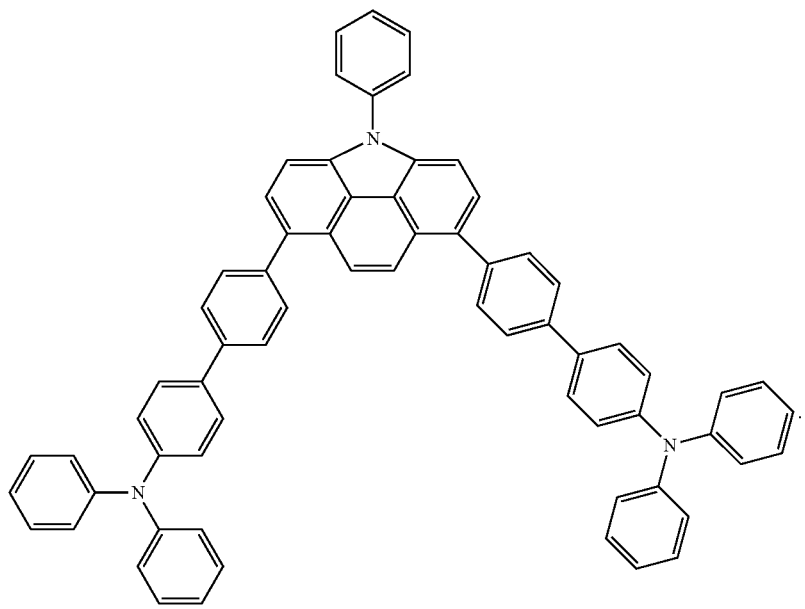
53

7. An organic light-emitting device, comprising:
a first electrode;
a second electrode; and
an organic layer between the first electrode and the second electrode, wherein the organic layer includes the compound of claim 1.

8. The organic light-emitting device of claim 7, wherein:
the organic layer includes an emission layer,
the compound represented by Formula 1 is a host or a dopant, and
the device is a fluorescent or phosphorescent device.

9. The organic light-emitting device of claim 7, wherein the organic layer is a hole injection layer, a hole transport layer, or a functional layer having both hole injection and hole transport capabilities.

10. The organic light-emitting device of claim 7, wherein:
the organic layer includes at least one of an emission layer, an electron injection layer, an electron transport layer, a functional layer having both electron injection and transport capabilities, a hole injection layer, a hole transport layer, or a functional layer having both hole injection and transport capabilities;
at least one of the hole injection layer, the hole transport layer, and the functional layer having both hole injection and hole transport capabilities further includes the compound represented by Formula 1; and
the emission layer includes an anthracene-based compound, an arylamine-based compound, or a styryl-based compound.

11. The organic light-emitting device of claim 7, wherein:
the organic layer includes at least one of an emission layer, an electron injection layer, an electron transport layer, a functional layer having both electron injection and transport capabilities, a hole injection layer, a hole transport layer, or a functional layer having both hole injection and transport capabilities;
at least one of the hole injection layer, the hole transport layer, and the functional layer having both hole injection and hole transport capabilities further includes the compound represented by Formula 1; and
the emission layer includes red, green, blue, and white emission layers, at least one of the red, green, blue, or white emission layers including a phosphorescent compound.

12. The organic light-emitting device of claim 11, wherein at least one of the hole injection layer, the hole transport layer, or the functional layer having both hole injection and hole transport capabilities further includes a charge-generating material.

13. The organic light-emitting device of claim 12, wherein the charge-generating material is a p-dopant.

14. The organic light-emitting device of claim 13, wherein the p-dopant is a quinine derivative, a metal oxide, or a cyano group-containing compound.

15. The organic light-emitting device of claim 7, wherein the organic layer includes an electron transport layer, the electron transport layer further including a metal complex.

16. The organic light-emitting device of claim 15, wherein the metal complex is a Li complex.

17. The organic light-emitting device of claim 15, wherein the metal complex is lithium quinolate (LiQ).

18. The organic light-emitting device of claim 15, wherein the metal complex is Compound 203 below

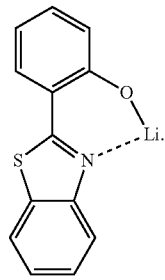

<Compound 203>

19. The organic light-emitting device of claim 7, wherein the organic layer is formed from the compound represented by Formula 1 using a wet process.

20. A flat panel display device comprising the organic light-emitting device of claim 7, wherein the first electrode of the organic light-emitting device is electrically connected to a source electrode or a drain electrode of a thin-film transistor.

* * * * *